US010025479B2

(12) United States Patent
Zhao et al.

(10) Patent No.: US 10,025,479 B2
(45) Date of Patent: Jul. 17, 2018

(54) ADVANCED MEDICAL IMAGE PROCESSING WIZARD

(71) Applicants: Tiecheng Zhao, Concord, MA (US); Akio Iwase, Brisbane, CA (US); Nobuyuki Kihara, Tokyo (JP)

(72) Inventors: Tiecheng Zhao, Concord, MA (US); Akio Iwase, Brisbane, CA (US); Nobuyuki Kihara, Tokyo (JP)

(73) Assignee: TERARECON, INC., Foster City, CA (US)

( * ) Notice: Subject to any disclaimer, the term of this patent is extended or adjusted under 35 U.S.C. 154(b) by 252 days.

(21) Appl. No.: 14/495,701

(22) Filed: Sep. 24, 2014

(65) Prior Publication Data

US 2015/0089365 A1    Mar. 26, 2015

Related U.S. Application Data

(60) Provisional application No. 61/882,162, filed on Sep. 25, 2013.

(51) Int. Cl.
*G06F 3/0484* (2013.01)
*G06F 19/00* (2018.01)
*A61B 34/10* (2016.01)

(52) U.S. Cl.
CPC .......... *G06F 3/04847* (2013.01); *A61B 34/10* (2016.02); *G06F 19/321* (2013.01)

(58) Field of Classification Search
CPC ................................................ G06F 3/04847
(Continued)

(56) References Cited

U.S. PATENT DOCUMENTS

| 4,803,639 A | * | 2/1989 | Steele | G01N 23/18 |
| | | | | 378/4 |
| 5,270,530 A | * | 12/1993 | Godlewski | G06F 19/321 |
| | | | | 250/208.1 |

(Continued)

FOREIGN PATENT DOCUMENTS

| JP | 2012-247880 | 12/2012 |
| JP | 2013-527503 | 6/2013 |
| WO | WO 2010/124850 | 11/2010 |

OTHER PUBLICATIONS

Elmar Kotter et al., "Technologies for image distribution in hospitals," European Radiology, Springer, Berlin, Germany, vol. 16, No. 6, Mar. 10, 2006.

(Continued)

*Primary Examiner* — Reza Nabi
*Assistant Examiner* — Daniel Rodriguez

(57) ABSTRACT

An automatic medical image processing system includes a series of operation stages, each automating specifying the image processing parameters for processing medical images. In response to an image processing indicator, a first medical image is automatically identified, including determining a first image operation and image processing parameters, without user intervention. The first image operation is performed on the first medical image based on the image processing parameters. A second medical image is generated and transmitted to the client device to be presented therein. The client device displays a message prompting the user whether the user is satisfied with the second medical image. In response to a user input from the client device indicating that the user is unsatisfied with the second medical image, one or more remedial options are presented to allow the user selecting a remedial action to reprocess the first medical image.

21 Claims, 31 Drawing Sheets

(58) Field of Classification Search
USPC .......................................................... 715/708
See application file for complete search history.

(56) References Cited

U.S. PATENT DOCUMENTS

| | | | |
|---|---|---|---|
| 5,384,862 A * | 1/1995 | Echerer | G06T 5/009 |
| | | | 382/132 |
| 5,431,161 A * | 7/1995 | Ryals | A61B 5/0275 |
| | | | 600/425 |
| 5,452,416 A | 9/1995 | Hilton et al. | |
| 5,767,854 A * | 6/1998 | Anwar | G06F 3/0481 |
| | | | 345/419 |
| 5,962,205 A * | 10/1999 | Arakawa | G03C 7/3029 |
| | | | 430/503 |
| 6,249,315 B1 * | 6/2001 | Holm | H04N 1/4072 |
| | | | 348/251 |
| 6,370,277 B1 * | 4/2002 | Borrey | H04N 1/00241 |
| | | | 382/254 |
| 6,538,831 B1 * | 3/2003 | Ikeda | A61B 6/00 |
| | | | 360/32 |
| 6,614,873 B1 | 9/2003 | Taylor et al. | |
| 6,871,340 B1 * | 3/2005 | Gillis | G06F 9/453 |
| | | | 717/100 |
| 7,107,547 B2 * | 9/2006 | Cule | G06Q 50/22 |
| | | | 715/810 |
| 7,127,097 B2 * | 10/2006 | Nagatsuka | G06T 5/009 |
| | | | 382/132 |
| 7,171,612 B2 * | 1/2007 | Toda | G06F 19/321 |
| | | | 715/201 |
| 7,180,624 B2 | 2/2007 | Tipirneni | |
| 7,324,673 B1 * | 1/2008 | Yamanaka | G06T 5/009 |
| | | | 358/520 |
| 7,522,175 B2 * | 4/2009 | Morita | G06F 3/1208 |
| | | | 345/619 |
| 7,564,579 B2 | 7/2009 | Tipirneni | |
| 7,583,861 B2 | 9/2009 | Hanna et al. | |
| 7,660,413 B2 | 2/2010 | Partovi et al. | |
| 7,660,488 B2 | 2/2010 | Reicher et al. | |
| 7,716,072 B1 | 5/2010 | Green et al. | |
| 7,725,359 B1 * | 5/2010 | Katzfey | G06Q 30/0603 |
| | | | 705/26.1 |
| 7,756,724 B2 | 7/2010 | Gropper et al. | |
| 7,787,672 B2 | 8/2010 | Reicher et al. | |
| 7,860,287 B2 | 12/2010 | Zahlmann et al. | |
| 7,936,908 B2 | 5/2011 | Brackett | |
| 7,953,614 B1 | 5/2011 | Reicher et al. | |
| 7,970,625 B2 | 6/2011 | Reicher et al. | |
| 8,059,297 B2 | 11/2011 | Tipirneni | |
| 8,065,166 B2 | 11/2011 | Maresh et al. | |
| 8,072,189 B2 | 12/2011 | Gering et al. | |
| 8,094,901 B1 | 1/2012 | Reicher et al. | |
| 8,229,194 B2 * | 7/2012 | Grunkin | G06F 19/321 |
| | | | 382/128 |
| 8,370,293 B2 | 2/2013 | Iwase et al. | |
| 8,488,916 B2 * | 7/2013 | Terman | G09B 5/08 |
| | | | 382/187 |
| 8,543,415 B2 * | 9/2013 | Venon | G06F 19/321 |
| | | | 705/2 |
| 8,644,973 B2 * | 2/2014 | Bake | A61F 2/30756 |
| | | | 606/88 |
| 8,682,049 B2 | 3/2014 | Zhao et al. | |
| 8,731,961 B2 | 5/2014 | Hanina et al. | |
| 9,408,016 B2 * | 8/2016 | Terry | H04W 4/008 |
| 2002/0183607 A1 * | 12/2002 | Bauch | G06T 19/00 |
| | | | 600/407 |
| 2003/0081255 A1 * | 5/2003 | Shimizu | H04N 1/46 |
| | | | 358/2.1 |
| 2003/0174216 A1 * | 9/2003 | Iguchi | H04N 1/4074 |
| | | | 348/223.1 |
| 2004/0071038 A1 * | 4/2004 | Sterritt | G06F 17/30274 |
| | | | 365/232 |
| 2004/0073092 A1 * | 4/2004 | Miles | G06Q 10/10 |
| | | | 600/300 |

| | | | |
|---|---|---|---|
| 2004/0078238 A1 | 4/2004 | Thomas et al. | |
| 2004/0111299 A1 * | 6/2004 | Onishi | G06F 19/321 |
| | | | 705/3 |
| 2004/0186746 A1 * | 9/2004 | Angst | G06F 21/6245 |
| | | | 705/3 |
| 2004/0220767 A1 * | 11/2004 | Tanaka | G06T 7/80 |
| | | | 702/127 |
| 2004/0240624 A1 | 12/2004 | Shiibashi et al. | |
| 2004/0257608 A1 | 12/2004 | Tipirneni | |
| 2004/0264756 A1 * | 12/2004 | Spahn | G06T 5/00 |
| | | | 382/132 |
| 2005/0021377 A1 | 1/2005 | Dobbs et al. | |
| 2005/0033151 A1 * | 2/2005 | Wu | G01R 33/50 |
| | | | 600/410 |
| 2005/0148849 A1 | 7/2005 | Heere et al. | |
| 2005/0267351 A1 | 12/2005 | Humphrey et al. | |
| 2005/0273205 A1 * | 12/2005 | Nickerson | A01G 25/16 |
| | | | 700/284 |
| 2006/0018549 A1 * | 1/2006 | Liang | G06K 9/00 |
| | | | 382/190 |
| 2006/0031093 A1 | 2/2006 | Serrano et al. | |
| 2006/0074983 A1 * | 4/2006 | Jones | G16H 10/65 |
| 2006/0093207 A1 | 5/2006 | Reicher et al. | |
| 2006/0115135 A1 * | 6/2006 | Dehmeshki | G06F 19/321 |
| | | | 382/128 |
| 2006/0133563 A1 * | 6/2006 | Hopkins | A61B 6/4035 |
| | | | 378/5 |
| 2006/0190999 A1 | 8/2006 | Chen et al. | |
| 2006/0204055 A1 * | 9/2006 | Steinberg | H04N 5/23212 |
| | | | 382/118 |
| 2006/0229911 A1 | 10/2006 | Gropper et al. | |
| 2006/0230072 A1 | 10/2006 | Partovi et al. | |
| 2006/0259505 A1 * | 11/2006 | Nodate | G16H 50/20 |
| 2006/0274928 A1 * | 12/2006 | Collins | A61B 6/00 |
| | | | 382/132 |
| 2006/0279754 A1 * | 12/2006 | Minakuti | H04N 1/6086 |
| | | | 358/1.9 |
| 2007/0005798 A1 | 1/2007 | Gropper et al. | |
| 2007/0019850 A1 * | 1/2007 | Knoplioch | G06K 9/342 |
| | | | 382/131 |
| 2007/0027715 A1 | 2/2007 | Gropper et al. | |
| 2007/0046966 A1 * | 3/2007 | Mussack | G06T 1/20 |
| | | | 358/1.13 |
| 2007/0075135 A1 | 4/2007 | Dettinger et al. | |
| 2007/0076929 A1 * | 4/2007 | Gentles | G06F 19/321 |
| | | | 382/128 |
| 2007/0078306 A1 * | 4/2007 | Allison | A61N 5/103 |
| | | | 600/300 |
| 2007/0083396 A1 * | 4/2007 | Kanada | G06F 19/321 |
| | | | 705/3 |
| 2007/0192140 A1 | 8/2007 | Gropper | |
| 2007/0237380 A1 * | 10/2007 | Iwase | A61B 6/032 |
| | | | 382/131 |
| 2007/0237415 A1 * | 10/2007 | Cao | H04N 1/3871 |
| | | | 382/254 |
| 2007/0255095 A1 * | 11/2007 | Gilreath | A61B 1/0005 |
| | | | 600/102 |
| 2007/0274449 A1 * | 11/2007 | Camus | A61B 6/4441 |
| | | | 378/98.12 |
| 2008/0025583 A1 | 1/2008 | Jabri et al. | |
| 2008/0059244 A1 * | 3/2008 | Fujita | G06F 19/321 |
| | | | 705/3 |
| 2008/0121168 A1 * | 5/2008 | Ryznar | G05B 19/41805 |
| | | | 116/201 |
| 2008/0152086 A1 * | 6/2008 | Hall | A61B 6/502 |
| | | | 378/98.2 |
| 2008/0242968 A1 * | 10/2008 | Claus | A61B 6/032 |
| | | | 600/407 |
| 2009/0006129 A1 * | 1/2009 | Thukral | G06F 19/3437 |
| | | | 705/2 |
| 2009/0041329 A1 * | 2/2009 | Nordell | G06F 19/321 |
| | | | 382/134 |
| 2009/0080747 A1 * | 3/2009 | Lu | G06T 7/0012 |
| | | | 382/131 |
| 2009/0103789 A1 | 4/2009 | Danner et al. | |
| 2009/0168965 A1 * | 7/2009 | Okuzawa | G03B 42/02 |
| | | | 378/98.5 |

(56) References Cited

U.S. PATENT DOCUMENTS

| | | | |
|---|---|---|---|
| 2009/0169073 A1* | 7/2009 | Areste | G06F 19/321 382/128 |
| 2009/0210487 A1 | 8/2009 | Westerhoff et al. | |
| 2009/0281839 A1 | 11/2009 | Lynn et al. | |
| 2009/0287271 A1* | 11/2009 | Blum | A61N 1/37247 607/45 |
| 2009/0290773 A1* | 11/2009 | Holt | G06F 19/321 382/131 |
| 2010/0021026 A1* | 1/2010 | Collins | G06K 9/00 382/128 |
| 2010/0049740 A1* | 2/2010 | Iwase | G06F 19/321 705/7.27 |
| 2010/0066822 A1* | 3/2010 | Steinberg | G06K 9/00208 348/77 |
| 2010/0086182 A1* | 4/2010 | Luo | G06T 5/00 382/128 |
| 2010/0122336 A1 | 5/2010 | Hunt et al. | |
| 2010/0135554 A1 | 6/2010 | Kohlmann et al. | |
| 2010/0146044 A1 | 6/2010 | Holmes et al. | |
| 2010/0183210 A1* | 7/2010 | Van Uitert | G06K 9/46 382/131 |
| 2010/0214536 A1* | 8/2010 | Kishida | A61B 3/1241 351/206 |
| 2010/0260393 A1* | 10/2010 | Truyen | G06F 19/321 382/128 |
| 2010/0329522 A1* | 12/2010 | Otsuka | G06K 9/2027 382/128 |
| 2010/0331047 A1* | 12/2010 | Bilcu | G06T 5/50 455/557 |
| 2011/0029914 A1* | 2/2011 | Whitby | G06T 11/60 715/781 |
| 2011/0110568 A1 | 5/2011 | Vesper et al. | |
| 2011/0153351 A1 | 6/2011 | Vesper et al. | |
| 2011/0166890 A1 | 7/2011 | Menschik et al. | |
| 2011/0191767 A1 | 8/2011 | Pinsky et al. | |
| 2011/0246231 A1* | 10/2011 | Sie | G06Q 10/10 705/3 |
| 2011/0251488 A1* | 10/2011 | Gritzky | A61B 8/00 600/443 |
| 2011/0263980 A1* | 10/2011 | Mills | G06F 19/321 600/439 |
| 2011/0274322 A1* | 11/2011 | Kern | A61B 3/0025 382/128 |
| 2011/0286683 A1* | 11/2011 | Hori | G06T 5/00 382/276 |
| 2011/0293152 A1* | 12/2011 | Choi | A61B 8/585 382/128 |
| 2012/0002853 A1 | 1/2012 | Omernick et al. | |
| 2012/0029939 A1* | 2/2012 | Danielson | G06Q 50/22 705/3 |
| 2012/0035954 A1 | 2/2012 | Yeskel | |
| 2012/0041786 A1 | 2/2012 | Yu | |
| 2012/0066238 A1* | 3/2012 | Fadem | A61B 5/0478 707/758 |
| 2012/0093383 A1* | 4/2012 | Claus | A61B 6/032 382/131 |
| 2012/0163684 A1 | 6/2012 | Natanzon et al. | |
| 2012/0173317 A1 | 7/2012 | Kelley | |
| 2012/0194540 A1 | 8/2012 | Reicher et al. | |
| 2012/0218290 A1* | 8/2012 | Waschbuesch | G09G 5/377 345/619 |
| 2012/0299818 A1* | 11/2012 | Li | G06F 3/0484 345/156 |
| 2012/0300997 A1* | 11/2012 | Li | G06F 19/321 382/128 |
| 2013/0024208 A1 | 1/2013 | Vining | |
| 2013/0039552 A1* | 2/2013 | Becker | G06F 19/321 382/128 |
| 2013/0072781 A1* | 3/2013 | Omernick | G06F 19/321 600/410 |
| 2013/0108126 A1* | 5/2013 | Leighow | G16H 30/20 382/128 |
| 2013/0131512 A1* | 5/2013 | Kim | A61B 8/465 600/440 |
| 2013/0251219 A1* | 9/2013 | Mehta | G06T 7/0012 382/128 |
| 2013/0310726 A1* | 11/2013 | Miller | A61M 1/288 604/5.04 |
| 2014/0038152 A1* | 2/2014 | Micieli | G06F 19/3418 434/267 |
| 2014/0140591 A1* | 5/2014 | Arazi | G06F 19/321 382/128 |
| 2014/0143643 A1* | 5/2014 | Ayed | G06F 19/321 715/202 |
| 2014/0143716 A1* | 5/2014 | Buelow | G06F 3/04845 715/788 |
| 2014/0152800 A1* | 6/2014 | Fomitchov | G01N 21/6458 348/79 |
| 2014/0201670 A1* | 7/2014 | Mallya | G06F 3/0481 715/771 |
| 2014/0304005 A1* | 10/2014 | Hughes | G06F 19/322 705/3 |
| 2014/0369578 A1* | 12/2014 | Itai | A61B 6/032 382/128 |
| 2015/0011208 A1* | 1/2015 | Terry | H04W 4/008 455/435.1 |
| 2015/0016700 A1* | 1/2015 | Drozdzal | G16H 40/63 382/128 |
| 2015/0038846 A1* | 2/2015 | Abe | A61B 8/06 600/443 |
| 2015/0086133 A1* | 3/2015 | Grady | G06F 17/30268 382/278 |
| 2015/0138329 A1* | 5/2015 | Braun | A61B 5/6861 348/71 |
| 2015/0153990 A1* | 6/2015 | Rust | G01S 7/003 345/2.2 |
| 2015/0161790 A1* | 6/2015 | Takahashi | A61B 5/0245 600/424 |
| 2015/0173847 A1* | 6/2015 | Hayashi | A61B 6/032 600/431 |
| 2015/0302581 A1* | 10/2015 | Dursteler | G06T 11/00 382/128 |
| 2015/0356756 A1* | 12/2015 | Okamoto | A61B 6/032 382/131 |
| 2016/0070436 A1* | 3/2016 | Thomas | A61B 5/055 715/771 |
| 2016/0078174 A1* | 3/2016 | Chung | G06Q 50/24 705/3 |

OTHER PUBLICATIONS

Munch, H. et al. "The integration of medical images with the electronic patient record and their web-based distribution," Academic Radiology, Reston, VA, US, vol. 11, No. 6, Jun. 1, 2004.

Ruth E. Dayhoff et al., "Providing complete multimedia patient data to consulting radiologists, other specialists, and the referring clinician," Journal of Digital Imaging; The Journal of the Society for Computer Applications in Radiology, Springer-Verlag, NE, vol. 11, No. 1, Aug. 1, 1998.

Steve G. Langer "Architecture of an image capable, web-based, electronic medical record," Journal of Digital Imaging; The Journal of the Society for Computer Applications in Radiology, Springer-Verlag, NE, vol. 13, No. 2, Feb. 1, 2000.

"IHE Cardiology Technical Framework Supplement: Image-Enabled Office (IEO) Integration Profile," IHE Cardiology Technical Committee (2009-2010); IHE International, Inc., Jul. 30, 2010, 47 pages.

PCT/US2014/057478, International Search Report and Written Opinion, dated Jan. 27, 2015, 13 pages.

* cited by examiner

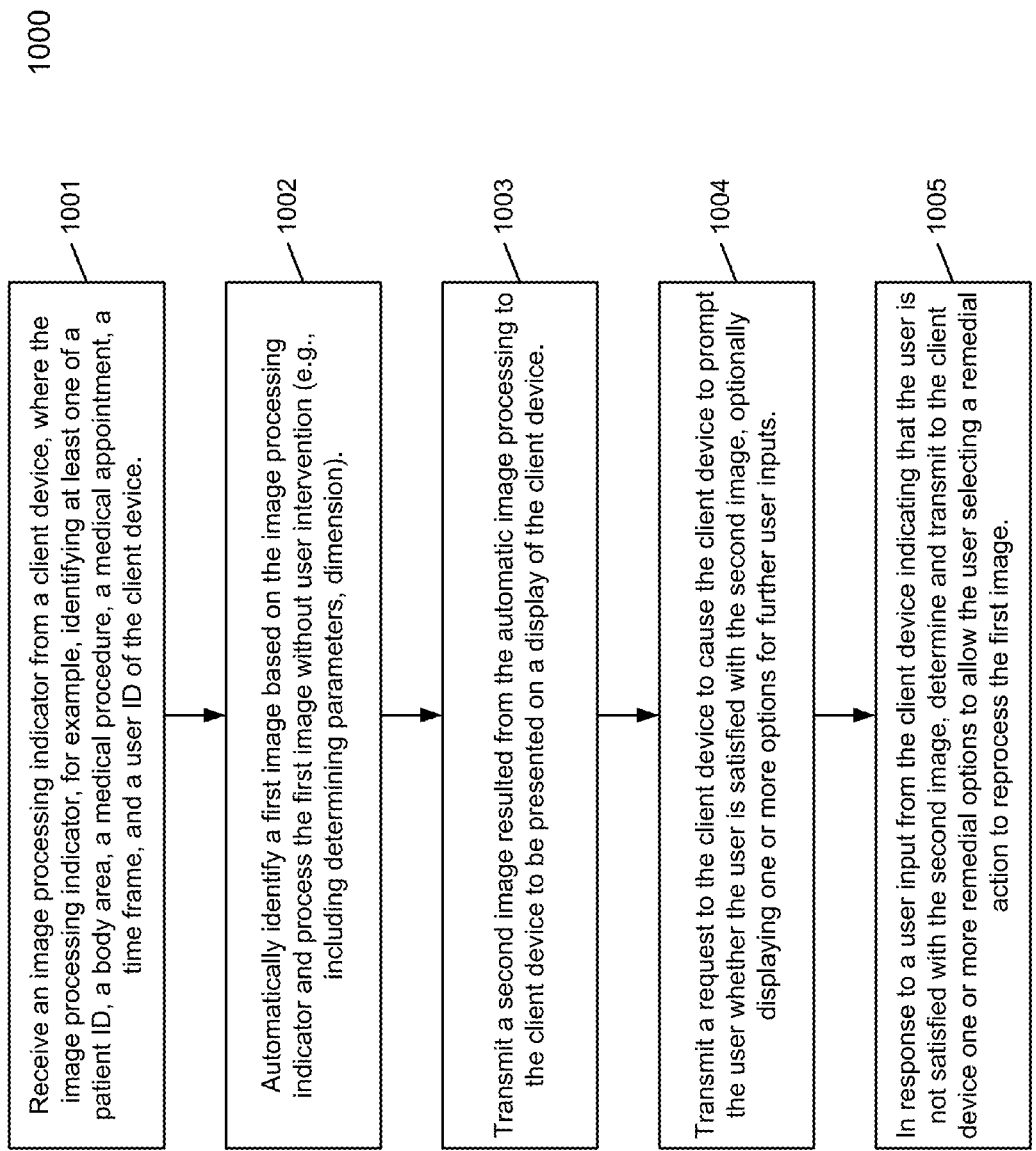

ADVANCED MEDICAL IMAGE PROCESSING WIZARD

RELATED APPLICATIONS

This application claims the benefit of U.S. Provisional Application No. 61/882,162, filed Sep. 25, 2013, which is incorporated by reference herein in its entirety.

FIELD OF THE INVENTION

Embodiments of the present invention relate generally to medical image processing systems. More particularly, embodiments of the invention relate to medical image processing wizard.

BACKGROUND

A computerized axial tomography scan (commonly known as a CAT scan or a CT scan) is an x-ray procedure, which combines many x-ray images with the aid of a computer to generate cross-sectional views of the internal organs and structures of the body. In each of these views, the body image is seen as an x-ray "slice" of the body. Typically, parallel slices are taken at different levels of the body, i.e., at different axial (z-axis) positions. This recorded image is called a tomogram, and "computerized axial tomography" refers to the recorded tomogram "sections" at different axial levels of the body. In multislice CT, a two-dimensional (2D) array of detector elements replaces the linear array of detectors used in conventional CT scanners. The 2D detector array permits the CT scanner to simultaneously obtain tomographic data at different slice locations and greatly increases the speed of CT image acquisition. Multislice CT facilitates a wide range of clinical applications, including three-dimensional (3D) imaging, with a capability for scanning large longitudinal volumes with high z-axis resolution.

Magnetic resonance imaging (MRI) is another method of obtaining images of the interior of objects, especially the human body. More specifically, MRI is a non-invasive, non-x-ray diagnostic technique employing radio-frequency waves and intense magnetic fields to excite molecules in the object under evaluation. Like a CAT scan, MRI provides computer-generated image "slices" of the body's internal tissues and organs. As with CAT scans, MRI facilitates a wide range of clinical applications, including 3D imaging, and provides large amounts of data by scanning large volumes with high resolution.

These image data are typically analyzed using complex software systems called advanced medical image processing systems. Advanced medical image processing software is currently complex and unapproachable to all but the experienced and trained user. However, as medical image processing software becomes more integrated with medicine and the electronic health record, it is becoming increasingly important for other users, such as other physicians and even non-physicians and patients, to be at least versant on these software systems.

As advanced medical imaging software becomes more sophisticated and common, simplifying the use of such software packages becomes more important and more challenging. Traditionally, Radiologists have been the primary user of sophisticated medical imaging software, and have undergone extensive training to be proficient on these software platforms. Radiologists may spend a significant portion of their time using such software packages and become experienced users.

Because of the software's complexity, it is virtually impossible for a lay person to figure out how to use advanced medical image processing software. Also, it is very difficult for an untrained physician to do the same. Attempts to do so by the inadequately trained may result in misinterpretation of image data and even medical mistakes such as misdiagnoses.

There is a need for a simple way for a minimally trained or untrained user to use advanced medical imaging software effectively.

BRIEF DESCRIPTION OF THE DRAWINGS

Embodiments of the invention are illustrated by way of example and not limitation in the figures of the accompanying drawings in which like references indicate similar elements.

FIG. 10 is a flow diagram illustrating a process performed by an automatic image processing system according to one embodiment of the invention.

DETAILED DESCRIPTION

Figure 1:
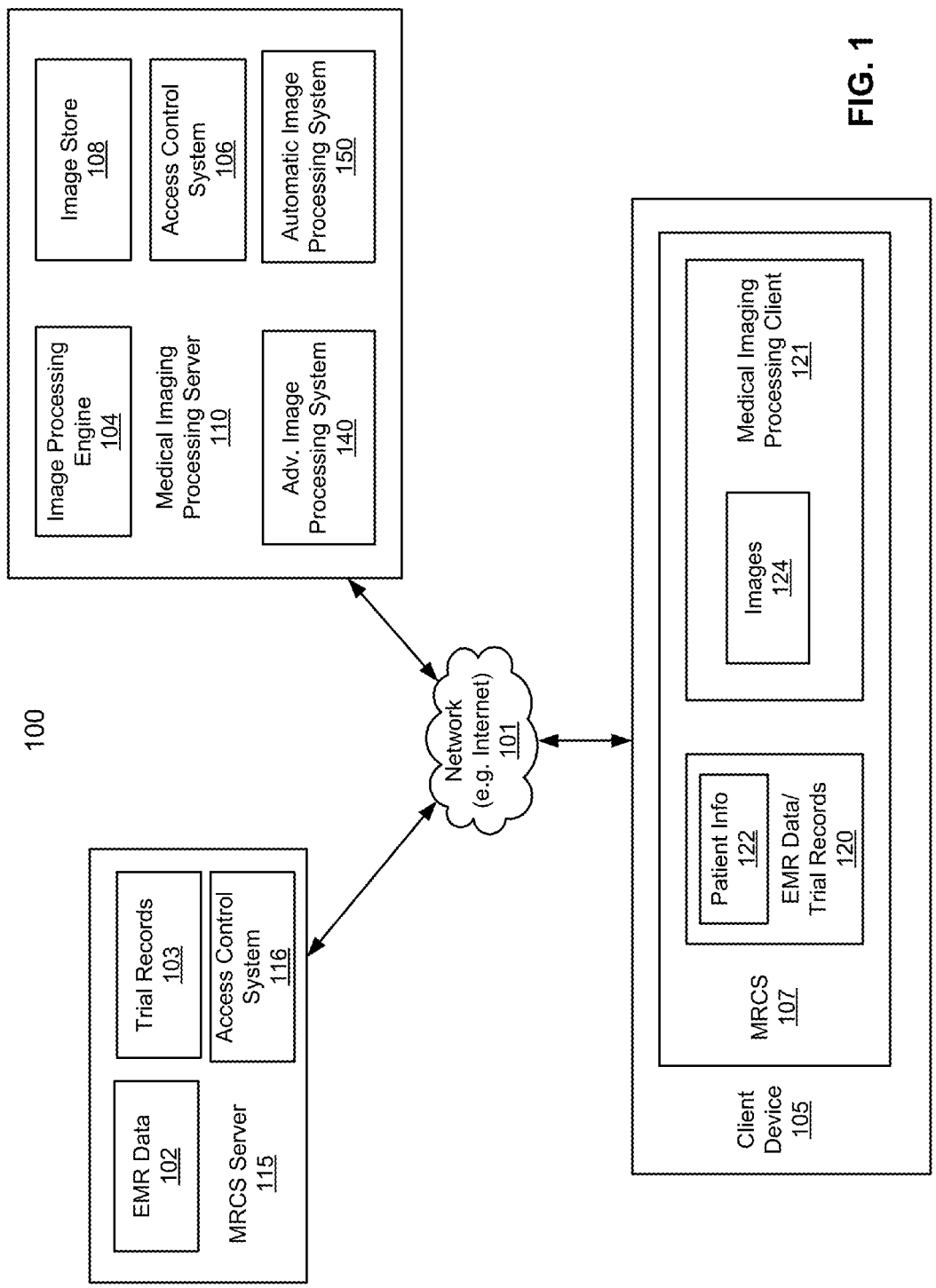
FIG. 1 is a block diagram illustrating integrated medical record and/or clinical software and advanced imaging processing system according to one embodiment.

Various embodiments and aspects of the inventions will be described with reference to details discussed below, and the accompanying drawings will illustrate the various embodiments. The following description and drawings are illustrative of the invention and are not to be construed as limiting the invention. Numerous specific details are described to provide a thorough understanding of various embodiments of the present invention. However, in certain instances, well-known or conventional details are not described in order to provide a concise discussion of embodiments of the present inventions.

Reference in the specification to "one embodiment" or "an embodiment" means that a particular feature, structure, or characteristic described in conjunction with the embodiment can be included in at least one embodiment of the invention. The appearances of the phrase "in one embodiment" in various places in the specification do not necessarily all refer to the same embodiment.

According to some embodiments, a software/hardware system is provided which simplifies or automates the use of an advanced medical image processing system. In one embodiment, in addition to an advanced image processing system, an automatic image processing system (also referred to as a simplified image processing system) is provided. This automatic image processing system may be layered on top of, or integrated with, an existing or new advanced medical image processing software system to simplify or automate the use of the medical image processing system, which may be implemented in software, hardware, or a combination of both. The automatic image processing system may be implemented in a form of an image processing wizard. The wizard guides a user through an advanced image processing process. The wizard automates as many steps as possible, for example, using preferences, assumptions, and/or a set of rules, to process image data, such that the user does not have to know the details of how to operate the advanced image processing tools. The wizard also gives the user an opportunity to confirm or change the results that were created automatically or otherwise. The wizard may consist of the presentation of intuitive user interfaces as well as easy to answer questions which help guide the user through the image processing process.

According to one embodiment, image processing software includes an automatic image processing system that provides a user friendly interactive graphical user interface. The automatic image processing system allows a user to interact with the image processing software based on a set of easily understandable processing stages to perform certain major or common or popular image processing operations on an image, without having to fully understand specific steps and/or image processing parameters for processing the image. The automatic image processing system may interact with the user through a series of questions and receive user inputs as a part of answers from the user to determine the user's intent. Based on the user interaction with the automatic image processing system, as well as metadata associated with image data, such as patient ID, medical procedure, body part, medical condition or other data/tags, one or more image processing operations may be determined and either recommended to the user or processed automatically. If recommended to the user, the user can select one or more of the recommended image processing operations for processing the image. One or more image processing parameters associated with the selected image processing operations are automatically determined by the underlying logic of the image processing software without user intervention and without having the user providing the same parameters. The image processing software may be hosted by an image processing server (which may include a Web server). A user can access the image processing software from a client device over a network (e.g., Internet). For example, the user can access the image processing software using a Web browser or alternatively, using a client application running at the client device.

Based on the image processing parameters, according to one embodiment, one or more image processing commands are generated and transmitted from the automatic image processing system to an image processing engine for image processing. The image processing engine may be communicatively coupled to the automatic image processing system, locally integrated within the image processing server or remotely via a set of APIs over a network. In response to receiving the image processing commends, the image processing engine processes the image based on the image processing parameters and generates a new or updated image. The new image may represent a different view of the same medical data associated with the original image. The new image is then transmitted from the image processing engine back to the automatic image processing system, which in turn transmits the new image to the client device to be presented to the user. In one embodiment, the automatic image processing system causes the client device to prompt the user whether the user is satisfied with the new image. If the user is unsatisfied with the new image, the automatic image processing system may communicate with the client device to interact with the user for more user inputs concerning the new image and further adjust the image processing parameters and the image processing operations may be iteratively performed. As a result, a user does not have to fully understanding how to utilize the advanced image processing system, although the advanced image processing system may also be available for advanced users. It is understood that a "view" or "image view" or "image" may contain information in addition to images, including quantitative data, identifying marks, measurements, outlines, mapping, layers such as color layers, etc. This additional data may be contained in image metadata. Also, "image" may mean one or more images, for example, it could represent an image series from a CT scan.

In one embodiment, image processing client software (e.g., thin client software) may be integrated with medical record and/or clinical trial (MRCS) client software, where the integrated MRCS client software may be able to access both a medical record server and the image processing software hosted by an image processing server to process medical images that are associated with a medical record of a particular patient. The automatic image processing system allows a user to select and process a medical image that is associated with a medical record of a patient, such as, for example, an image associated with a body part, a medical procedure, a medical appointment with doctors, and/or a medical condition of a patient, etc.

FIG. 1 is a block diagram illustrating integrated MRCS and advanced imaging processing system according to one embodiment. Referring to FIG. 1, according to one embodiment, system 100 includes a client 105 communicatively coupled to a medical imaging processing server 110 and MRCS server 115 over a network 101, wired and/or wirelessly. Network 101 may be a local area network (LAN), a metropolitan area network (MAN), a wide area network (WAN) such as the Internet or an intranet, a private cloud network, a public cloud network, or a combination thereof. Although FIG. 1 illustrates a single client 105 communicatively coupled to the imaging processing server 110 and medical data server 115, it will be appreciated that multiple such clients may be communicatively coupled to the medical imaging processing server 110 and/or MRCS server 115.

MRCS server 115, in one embodiment, may be a data server that resides physically in a different location from the medical imaging processing server 110 and the client 105. In another embodiment, the MRCS server 115 may be in the same geographic location as the medical imaging processing server 110 and/or client 105. MRCS server 115 may be operated by the same or different organization from client 105 and/or imaging processing server 110. In one embodiment, the MRCS server 115 includes data storage to store medical records of patients such as EMRs or EHRs 102.

MRCS server 115 may also store clinical trial records 103 of anonymous patients. MRCS server 115 further includes access control system 116 for providing access to EMR Data 102 and trial records 103. Different users having different roles may be allowed to access different data. For example, a doctor may be allowed to access EMR data 102, while a medical student or professor may be allowed to access only the trial records 103. For the purpose of illustration, MRCS server 115 may represent a MRS server, a CTS server, or a combination of both and MRCS sever 115 may be implemented in a single server or a cluster of servers. Also note that MRCS server 115 may represent two separate serves: 1) a MRS server having EMR data 102 stored therein; and 2) a CTS server having trial records 103 stored therein.

Medical imaging processing server 110 includes image processing engine 104 which is configured to provide medical image processing services to client 105 over a network. In one embodiment, the medical imaging processing server 110 also includes an image store 108 to store medical data such as digital imaging and communications in medicine (DICOM) compatible data or other image data, including JPEG, TIFF, video, EKG, laboratory images, reports, text, PDF, sound, and other files. The image store 108 may also incorporate encryption capabilities, where the medical data can be stored and transmitted in an encrypted form. The image store 108 may include multiple databases, and may be implemented with relational database management systems (RDBMS), e.g., Oracle™ database or Microsoft® SQL Server, etc.

In one embodiment, the medical imaging processing server 110 includes an access control system 106 to control access, by the client 105, of resources (e.g., image processing tools) and/or medical data stored in image store. Client 105 may or may not access certain portions or types of resources and/or medical data stored in image store depending upon its access privilege. The access privileges may be determined or configured based on a set of role-based rules or policies. For example, client 105 may be configured with certain roles that only permit access to some of the tools provided by the medical imaging processing server 110. In other instances, client 105 may be configured with certain roles that limit its access to some patient information. For example, certain users (e.g., doctors, medical students) of client 105 may have different access privileges to access different medical information stored in image store 108 or different imaging rendering resources provided by imaging processing server 110.

Client device 105 is a client which may include integrated medical software 107 as described herein. In one embodiment, the integrated software 107 integrates image(s) and/or image processing functionality 121 with medical record software (MRS) and/or clinical trial software (CTS) 107, which herein are collectively referred to as medical record and/or clinical software (MRCS). For example, imaging processing function may be implemented as a medical imaging processing client 121 communicatively coupled to image processing server 110 over network 101. Imaging processing client 121 may be linked to medical software 107 or embedded within medical software 107. MRCS client 107 and Medical Imaging Processing client may also be completely separate, i.e. non-integrated.

MRS is patient-centric software that focuses on medical records of the individual patients. Patient-centric means here that the software's primary purpose is to record and view data relating to the individual patient. This type of software may be referred to as electronic medical record (EMR) software, electronic health record (EHR) software, personal health record (PHR) software and other names. Information maintained by the MRS typically includes: patient ID, demographic, info—age, weight, height, Blood Pressure (BP), etc., lab orders and results, test orders and results, medical history, appointment history, appointments scheduled, exam history, prescriptions/medications, symptoms/diagnoses, and insurance/reimbursement info.

CTS includes software for both retrospective and prospective clinical studies. This type of software may be referred to as a Clinical Trial Management System. CTS may also include software for research. CTS is trial-centric which means the primary purpose of the software is to collect and view aggregate data for multiple patients or participants. Although data is collected at the individual patient/participant level, this data is usually viewed "blindly". This means that the viewer and/or analyzer of the data generally do not know the identity of the individual patients/participants. However, data can be viewed at the individual patient/participant level where necessary. This is particularly important where images are involved. CTS typically includes: patient ID, concomitant medications, adverse events, randomization info, data collection, informed consent, aggregated data, and status of study.

In one embodiment, the MRCS 107 of the integrated medical software executed within the client 105 displays medical information 122 of a patient, including, e.g., the medical treatment history of a patient, which may be part of a medical record and/or trial record 120 of the patient. Such records 120 may be downloaded from medical data server 115 in response to a user request. In the case where the integrated medical software integrates MRS, the patient's full identity it typically displayed as part of the medical information. On the other hand, in the case of an integrated CTS, the patient is typically anonymous as discussed above, and the identity of the patient is typically not revealed as part of the displayed medical information.

In one embodiment, image(s) and/or image processing function 121 is integrated with the MRCS. Integration can take the form of the image(s) and/or image processing tools showing up in the same window as the MRCS. Integration can also take the form of a window containing the image(s) and/or image processing tools opening up in a separate window from the MRCS window. It should be noted, however, that in either form of integration, the medical information of the patient and image(s) are displayed within the integrated medical software, without requiring the user of the integrated software to separately obtain the images via another software program.

In one embodiment, when the advanced image processing system is utilized, a set of graphical representation representing a set of image processing tools may be presented in an advanced image processing graphical user interface to allow a user to specify one or more of the image processing tools to process a particular one of images 124. When the automatic image processing system is utilized, the underlying processing logic of automatic image processing system 150 is configured to automatically determine and select one or more image processing tools to process the image, for example, without user intervention or user knowledge of which of the image processing tools to be utilized. The graphical representations (e.g., icons) for image processing tools that are provided by the remote imaging processing server 110 are displayed to the user of the integrated medical software executed on the client 105. In such an embodiment, the available image processing tools are displayed in the integrated medical software as a set of icons or some other graphical representations, which when activated by a user, allow an image to be manipulated by remote imaging processing server 110. In one embodiment the image processing software is integrated with the MRCS program and also opens up "in context". "In context" means that the image processing software opens up to show the appropriate image(s) and/or tools for the current user and/or patient and/or affliction. The availability of imaging tools to a particular user depends on the access privileges of that particular user (e.g., doctors vs. medical students). Alternatively, the availability of imaging tools may be determined based on a particular body part of a patient, which may be identified by certain tags such as DICOM tags.

For example, one doctor may prefer that the cardiovascular images for his patients open up in a 3D view, with vessel centerline tools available, yet the abdominal images for his patients open up in a coronal view with the flythrough, or virtual colonoscopy, tools available. He may prefer to have the other views and tools hidden from view. In another example, another doctor may prefer that the images for her patients open up showing the most recent views and tools that she used for that patient. In another example, the default view for cardiovascular cases may be set to show a particular view and tools, but the user may be able to change the default so that his/her preferences override the default views and tools.

In all of the above examples, ideally only the images that relate to the patient being evaluated at that time are able to be viewed. In addition, the user/physician does not need to search to find the images relating to the patient, the images 124 are automatically associated with the correct patient, for example, based on the corresponding patient ID. To do this, the identity of the patient needs to be associated with the patient's images. This can be done by using tags, such as a common identifier, such as an ID number, metadata associated with one or more of the images, mining patient data, body part analysis, or other ways. Also, the appropriate tools need to be shown and inappropriate tools hidden. The tags are discussed in more details below.

For example, an image or image series can be analyzed to determine whether it is a head, abdomen, or other body part, based on the anatomy. A skull has a characteristic shape, as do other parts of the anatomy. A catalog of reference images may be used to help identify specific body parts. Based on this analysis, the appropriate views and/or tools can be made visible to the user, and inappropriate views and/or tools can be hidden. For example, if the image series is of a head/skull, the image series may be shown in a certain view, such as an axial view, and tools associated with the brain visible. In addition, if certain key words, such as "tumor" or "stroke", are found in the MRCS record, specific tools may be shown, such as tools that detect a tumor or evaluate brain perfusion. It is also possible that a patient ID can be determined from the anatomy in an image based on shape, disease, tags etc. For example, an image of a dental area can be matched with dental records to identify a patient from medical images. Or, an identifying tag can be included in the medical image—such as a tag with the patient ID number placed on or near the table of a CT scanner, or on the patient himself. In another embodiment, the user of the software is able to customize how the image processing software is presented in context. For example, Doctor Y, a cardiologist, may prefer to have the images open up in a 3D model view, and have cardiology tool A and cardiology tool B visible to him. In this example, other views may be hidden (for example, the axial, sagittal, and coronal views) and other tools are hidden (for example, tools relating to the colon or the brain).

According to one embodiment, image processing server 110 includes advance image processing system 140 to allow users of different types to access the imaging tools represented by tool icons for processing images 124, which utilize processing resources (e.g., image processing engine 104) provided by medical image processing server 110 over network 101. Image processing server 110 also includes automatic image processing system 150 to allow users of different types to access the functionality of imaging tools without having to deal with the tools directly. The functionality of the tools is provided by medical image processing server 110 over network 101. Automatic image processing system 150 may be layered on top of, or integrated with, an existing or new advanced medical image processing software system (e.g., advanced image processing system 140) to simplify or automate the use of the medical image processing resources (e.g., image processing engine 104), which may be implemented in software, hardware, or a combination of both.

According to one embodiment, both advanced image processing system 140 and automatic image process system 150 may access the image processing functions (e.g., libraries, routines, tools, etc.) of image processing engine 104 via a set of application programming interfaces (APIs) or communication protocols (if image processing engine 104 is a remote system over a network). When advanced image processing system 140 is utilized, according to one embodiment, an advanced graphical user interface may be presented, for example, similar to the graphical user interface as shown in FIG. 8H, to allow the user to specify detailed image processing parameters for processing a specific image selected by the user. The underlying processing logic of advanced image processing system 140 (e.g., advanced image processing module 303 of FIG. 3) processes the user inputs received from the advanced graphical user interface and formulates one or more image processing commands with a set of image processing parameters that are generated based on the user inputs. The processing logic of advanced image processing system 140 then sends the commands, for example, via the APIs, to image processing engine 104 to process the image.

When automatic image processing system 150 is utilized, according to one embodiment, a simplified graphical user interface (e.g., wizard) is presented at a client device of the user to walk the user through a series of simple steps or interactive questions without requiring the user to specify the detailed operational image processing parameters. The underlying processing logic (e.g., automatic image processing module 304 of FIG. 3) is configured to automatically determine the detailed image processing parameters based on the user interaction with the simplified graphical user interface. A set of image processing commands is generated and sent to image processing engine 104 for processing the image. Alternatively, the underlying processing logic of automatic image processing system 150 determines the parameters and passes the parameters to the advanced image processing system 140, just as the advanced image processing system would have received from a user via its corresponding graphical user interface. The advanced image processing system 140 in turn communicates with image processing engine 104 on behalf of automatic image processing system 150.

The automatic image processing system 150 may be implemented in a form of an image processing wizard. The wizard guides a user through the advanced image processing process. The wizard automates as many steps as possible, for example, using preferences, assumptions, and a set of rules, to process image data, such that the user does not have to know the details of how to operate the advanced image processing tools. The wizard also gives the user an opportunity to confirm or change the results that were created automatically or otherwise. The wizard may consist of the presentation of intuitive user interfaces as well as easy to answer questions which help guide the user through the image processing process.

According to one embodiment, automatic image processing system 150 provides a user friendly interactive graphical user interface. The automatic image processing system 150 allows a user to access the underlying processing resources of image processing server 110 based on a set of easily understandable processing stages to perform certain major or common or popular image processing operations on an image, without having to fully understand specific steps and/or image processing parameters or tools for processing the image. The automatic image processing system 150, through a user friendly graphical user interface (GUI), may interact with the user through a series of questions and receive user inputs as a part of answers from the user to determine the user's intent. Based on the user interaction with the automatic image processing system 150, one or more image processing operations may be determined and recommended to the user via automatic image processing system 150. The user can select one or more of the recommended image processing operations for processing the image, or alternatively, image processing operations may be performed automatically by the automatic image processing system 150. Based on a user selection of one or more of the image processing indicators, one or more image processing parameters associated with the selected image processing operations are automatically determined without user intervention and without having the user providing the same parameters.

Based on the image processing parameters received by the automatic image processing system 150, according to one embodiment, one or more image processing commands are generated and transmitted from the automatic image processing system 150 to image processing engine 104 for image processing. In response to the image processing commends, image processing engine 104 of image processing server 110 processes the image based on the image processing parameters and generates a new or updated image. The new image may represent a different view of the same medical data associated with the original image. The new image is then transmitted from the image processing server 110 back to automatic image processing system 150, which in turn transmits the new image to client device 105 to be presented to the user. The automatic image processing system 150 also causes client 105 to prompt the user whether the user is satisfied with the new image. If the user is unsatisfied with the new image, automatic image processing system 150 may interact with the user for more user inputs concerning the new image and further adjust the image processing parameters and the image processing operations may be iteratively performed. As a result, a user does not have to fully understanding how to utilize the advanced image processing system, although the advanced image processing system may also be available for advanced users.

Figure 2:
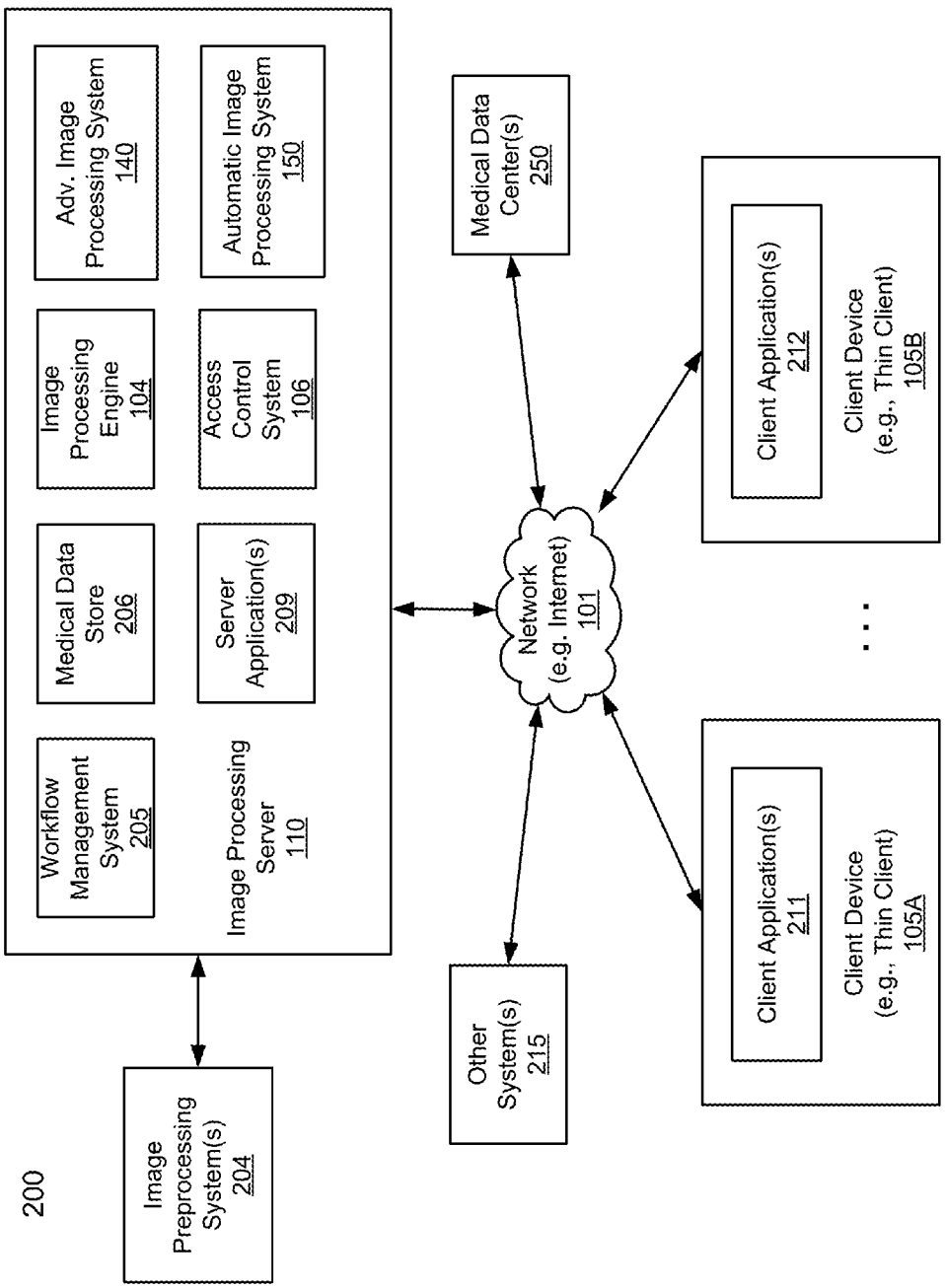
FIG. 2 is a block diagram illustrating an image processing system according to another embodiment of the invention.

FIG. 2 is a block diagram illustrating an image processing system according to another embodiment of the invention. In this embodiment, image processing clients may be implemented as standalone clients accessing an image processing server over the cloud (e.g., Internet). Referring to FIG. 2, system 200 includes image processing server 110 communicatively coupled to one or more clients 105A-105B over network 101, which may be a LAN, MAN, WAN, or a combination thereof. Server 110 is configured to provide cloud-based image processing services to clients 105A-105B based on a variety of usage licensing models. Each of clients 105A-105B includes a client application such as client applications 211-212 to communicate with server 110, respectively, to access resources provided by server 110. Client applications 211-212 may be thin client applications or browser applications. Server application 209 may be implemented as a virtual server or instance of the server application 110, one for each client.

According to one embodiment, server 110 includes, but is not limited to, workflow management system 205, medical data store 206, image processing system 104, and access control system 106. Medical data store 206 may be implemented as part of database 110 of FIGS. 1A and 1B. Medical data store 206 is utilized to store medical images and image data received from a medical data center (e.g., PACS systems, not shown) or other image storage systems 215 (e.g., CD-ROMs, or hard drives) and processed by image processing system 104 and/or image preprocessing systems 204. Image processing system 104 includes a variety of medical imaging processing tools or applications that can be invoked and utilized by clients 105A-105B via their respective client applications 211-212, respectively, according to a variety of licensing terms or agreements. It is possible that in some medical institutes that the image storage system 215 and an image capturing device may be combined.

In response to image data received from a medical data center or from image capturing devices (not shown) or from another image source, such as a CD or computer desktop, according to one embodiment, image preprocessing system 204 may be configured to automatically perform certain preprocesses of the image data and store the preprocessed image data in medical data store 206. For example, upon receipt of an image data from PACS or directly from medical image capturing devices, image preprocessing system 204 may automatically perform certain operations, such as bone removal, centerline extraction, sphere finding, registration, parametric map calculation, reformatting, time-density analysis, segmentation of structures, and auto-3D operations, and other operations, some of which are listed later herein. Image preprocessing system 204 may be implemented as a separate server or alternatively, it may be integrated with server 110. Furthermore, image preprocessing system 204 may perform image data preprocesses for multiple cloud servers such as server 110.

In one embodiment, a client/server image data processing architecture is installed on system 200. The architecture includes client partition (e.g., client applications 105A-105B) and server partition (e.g., server applications 209). The server partition of system 200 runs on the server 110, and communicates with its client partition installed on clients 105A-105B, respectively. In one embodiment, server 110 is distributed and running on multiple servers. In another embodiment, the system is a Web-enabled application operating on one or more servers. Any computer or device with Web-browsing application installed may access and utilize the resources of the system without any, or with minimal, additional hardware and/or software requirements.

In one embodiment, server 110 may operate as a data server for medical image data received from medical image capturing devices. The received medical image data is then stored into medical data store 206. In one embodiment, for example, when client 105A requests for unprocessed medical image data, server application 110 retrieves the data from the medical data store 206 and renders the retrieved data on behalf of client 105A.

Image preprocessing system 204 may further generate workflow information to be used by workflow management system 205. Workflow management system 205 may be a separate server or integrated with server 110. Workflow management system 205 performs multiple functions according to some embodiments of the invention. For example, workflow management system 205 performs a data server function in acquiring and storing medical image data received from the medical image capturing devices. It may also act as a graphic engine or invoke image processing system 207 in processing the medical image data to generate 2D or 3D medical image views.

In one embodiment, workflow management system 205 invokes image processing system 104 having a graphics engine to perform 2D and 3D image generating. When a client (e.g., clients 105A-105B) requests for certain medical image views, workflow management system 205 retrieves medical image data stored in medical data store 206, and renders 2D or 3D medical image views from the medical image data. The end results for medical image views are sent to the client.

In one embodiment, a user makes adjustments to the medical image views received from server 110, and these user adjustment requests are sent back to the workflow management system 205. Workflow management system 205 then performs additional graphic processing based on the user requests, and the newly generated, updated medical image views are returned to the client.

As described above, when implemented as a cloud based application, system 200 includes a client-side partition and a server-side partition. Functionalities of system 200 are distributed to the client-side or server-side partitions. When a substantial amount of functionalities are distributed to the client-side partition, system 200 may be referred to as a "thick client" application. Alternatively, when a limited amount of functionalities are distributed to the client-side partition, while the majority of functionalities are performed by the server-side partition, system 200 may be referred to as a "thin client" application. In another embodiment, functionalities of system 200 may be redundantly distributed both in client-side and server-side partitions. Functionalities may include processing and data. Server 110 may be implemented as a web server. The web server may be a third-party web server (e.g., Apache™ HTTP Server, Microsoft® Internet Information Server and/or Services, etc.) The client applications 211-212 may be a web browser.

In one embodiment, workflow management system 205 manages the creation, update and deletion of workflow templates. It also performs workflow scene creation when receiving user requests to apply a workflow template to medical image data. A workflow is defined to capture the repetitive pattern of activities in the process of generating medical image views for diagnosis. A workflow arranges these activities into a process flow according to the order of performing each activity. Each of the activities in the workflow has a clear definition of its functions, the resource required in performing the activity, and the inputs received and outputs generated by the activity. Each activity in a workflow is referred to as a workflow stage, or a workflow element. With requirements and responsibilities clearly defined, a workflow stage of a workflow is designed to perform one specific task in the process of accomplishing the goal defined in the workflow. For many medical image studies, the patterns of activities to produce medical image views for diagnosis are usually repetitive and clearly defined. Therefore, it is advantageous to utilize workflows to model and document real life medical image processing practices, ensuring the image processing being properly performed under the defined procedural rules of the workflow. The results of the workflow stages can be saved for later review or use.

In one embodiment, a workflow for a specific medical image study is modeled by a workflow template. A workflow template is a template with a predefined set of workflow stages forming a logical workflow. The order of processing an activity is modeled by the order established among the predefined set of workflow stages. In one embodiment, workflow stages in a workflow template are ordered sequentially, with lower order stages being performed before the higher order stages. In another embodiment, dependency relationships are maintained among the workflow stages. Under such arrangement, a workflow stage cannot be performed before the workflow stages it is depending on being performed first. In a further embodiment, advanced workflow management allows one workflow stage depending on multiple workflow stages, or multiple workflow stages depending on one workflow stage, etc.

The image processing operations receive medical image data collected by the medical imaging devices as inputs, process the medical image data, and generate metadata as outputs. Metadata, also known as metadata elements, broadly refers to parameters and/or instructions for describing, processing, and/or managing the medical image data. For instance, metadata generated by the image processing operations of a workflow stage includes image processing parameters that can be applied to medical image data to generate medical image views for diagnostic purpose. Further, various automatic and manual manipulations of the medical image views can also be captured as metadata. Thus, metadata allows the returning of the system to the state it was in when the metadata was saved.

After a user validates the results generated from processing a workflow stage predefined in the workflow template, workflow management system 205 creates a new scene and stores the new scene to the workflow scene. Workflow management system 205 also allows the updating and saving of scenes during user adjustments of the medical image views generated from the scenes. Further detailed information concerning workflow management system 205 can be found in co-pending U.S. patent application Ser. No. 12/196,099, entitled "Workflow Template Management for Medical Image Data Processing," filed Aug. 21, 2008, now U.S. Pat. No. 8,370,293, which is incorporated by reference herein in its entirety.

Referring back to FIG. 2, according to one embodiment, image processing server 110 includes advanced image processing system 140 and automatic image processing system 150. Automatic image processing system 150 may be layered on top of, or integrated with, an existing or new advanced medical image processing software system (e.g., advanced image processing system 140) to simplify or automate the use of the medical image processing system, which may be implemented in software, hardware, or a combination of both. The automatic image processing system 150 may be implemented in a form of an image processing wizard, as described above.

According to one embodiment, automatic image processing system 150 provides a user friendly interactive graphical user interface. The automatic image processing system 150 allows a user to interact with the image processing software hosted by image processing server 110 based on a set of easily understandable processing stages to perform certain major or common or popular image processing operations on an image or images, without having to fully understand specific steps and/or image processing parameters for processing the image. The automatic image processing system 150 may interact with the user through a series of questions and receive user inputs as a part of answers from the user to determine the user's intent. Based on the user interaction with the automatic image processing system 150, one or more image processing operations may be determined and recommended to the user via automatic image processing system 150. Alternatively, automatic image processing system 150 may automatically perform the image processing without user intervention. The user can select one or more of the recommended image processing operations for processing the image. Based on a user selection of one or more of the image processing indicators, one or more image processing parameters associated with the selected image processing indicators are automatically determined without user intervention and without having the user providing the same parameters.

Based on the image processing parameters received by automatic image processing system 150, according to one embodiment, one or more image processing commands are generated and transmitted from automatic image processing system 150 to image processing engine 104. In response to the image processing commends, image processing engine 104 of image processing server 110 processes the image based on the image processing parameters and generates a new or updated image. The new image may represent a different view of the same medical data associated with the original image. The new image is then transmitted from the image processing engine 104 back to the automatic image processing system 150, which in turns transmits the new image to a client device to be presented to the user. The user is prompted whether the user is satisfied with the new image. If the user is unsatisfied with the new image, the system may interact with the user for more user inputs concerning the new image and further adjust the image processing parameters and the image processing operations may be iteratively performed. As a result, a user does not have to fully understanding how to utilize the advanced image processing system, although the advanced image processing system may also be available for advanced users.

Figure 3:
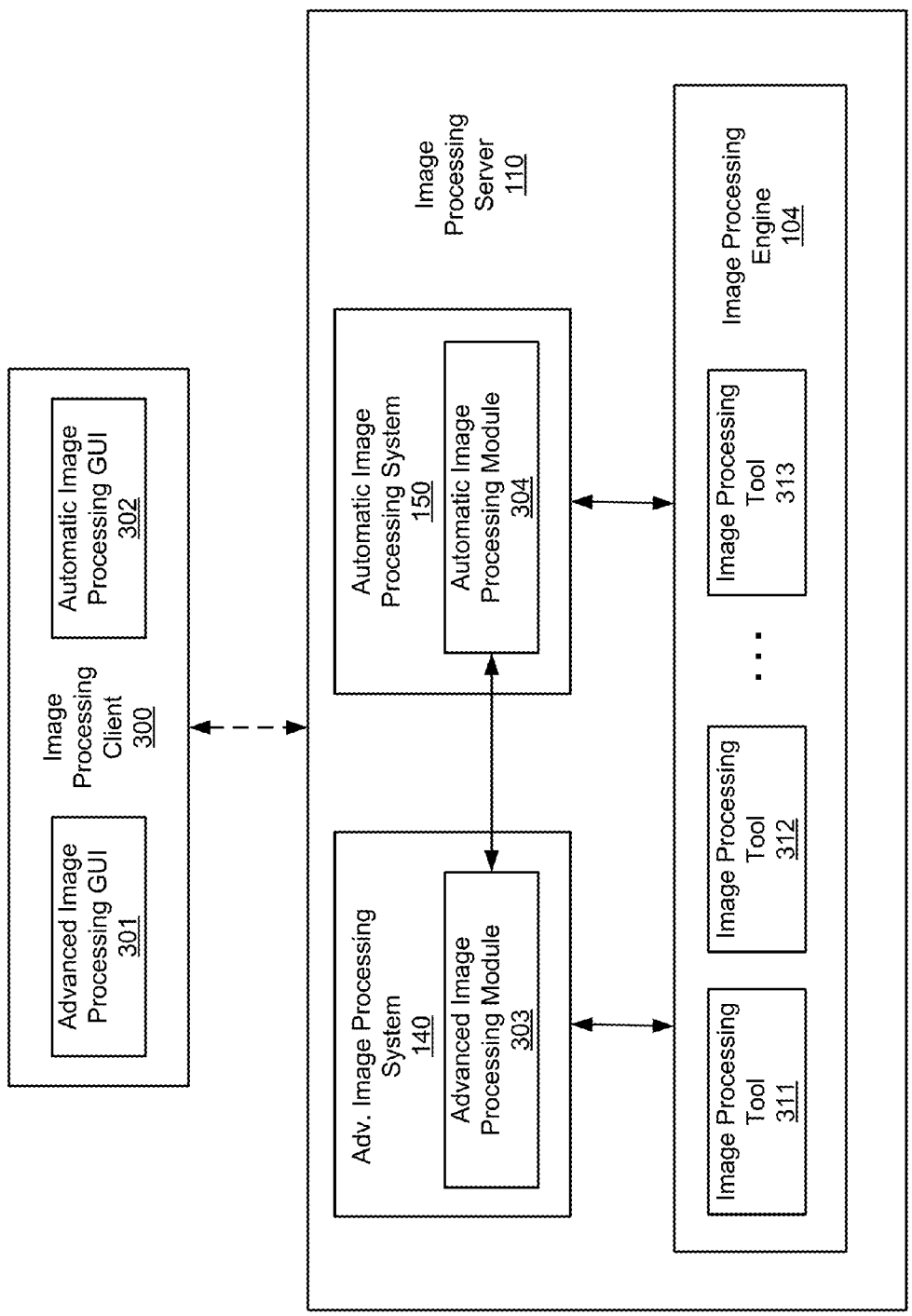
FIG. 3 is a block diagram illustrating an example of an image processing software application according to one embodiment of the invention.

FIG. 3 is a block diagram illustrating an example of an image processing client application according to one embodiment of the invention. Image processing client 300 may be implemented as a part of image client 121 in FIG. 1 and/or client applications 211-212 of FIG. 2. Referring to FIG. 3, image processing client 300 is communicatively coupled to image processing server 110 over a network. In one embodiment, Image processing server 110 includes advanced image processing system 140 and automatic image processing system 150 coupled to image processing logic 310, which may be implemented in software, hardware, or a combination of both.

Advanced image processing system 140 includes functionalities similar to those described in the above incorporated-by-reference U.S. patent application. Advanced image processing system 140 presents advanced image processing graphical user interface (GUI) 301 at client 300 and includes corresponding advanced image processing module, logic, or processor 303. Advanced image processing GUI 301 is used to present detailed processing interface to allow an advanced or experience user to specifically specify detailed parameters for processing a medical image. GUI 301 may include multiple input fields or controls to receive specific image processing parameters. For example, the user may use tools to take manual measurements, identify anatomy, segment anatomy etc. More tool functions will be described in details further below herein. The image processing indicators provided by a user are received via GUI 301 and processed by advanced image processing module 303. The image processing indicators may be determined based on the user interactions with advanced image processing GUI 301. For example, when a user clicks an item or tag displayed by GUI 301, the click event or action of the specific item or tag is transmitted from client 300 to server 110, and analyzed and interpreted by advanced image processing module 303 based on the underlying information associated with the item or tag to determine an image process operation associated with that particular item or tag. Advanced image processing module 303 then generates one or more image processing commands. The image processing commands are then transmitted to image processing engine 104 for processing medical images, using image processing tools or functions 311-313. An example of advanced image processing GUI 301 may be similar to the one as shown in FIG. 8H, from which a user can manually specify more input parameters.

Similarly, according to one embodiment, automatic image processing system 150 presents automatic image processing GUI 302 at client 300. GUI 302 provides a simple or automated user interface to interact with a user, for example, via a wizard, to guide the user to "walk" through a series of the major steps of image processing operations without requiring the user to know or provide detailed information of the processing operations. For example, GUI 302 may prompt the user with a series of questions and based on the answers received from the user, image processing module 304 analyzes the user interaction to determine the user intent. Based on the analysis, image processing module, logic, or processor 304 determines a list of one or more image processing operations. The image processing operations may be those that are more common or popular amongst the users based on the similar user interactions. Alternatively, the image processing operations may be determined based on a set of rules that is formulated based on the prior interactions or user preferences of the user.

In addition, processing module 304 determines a set of image processing parameters based on the image processing operations. The image processing commands and parameters are determined by processing module 304 automatically without user interventions, including selecting a proper image processing tool or tools. The image processing parameters or tools are not exposed or visible to the user and the user does not have to fully understand the parameters. However, if the user wishes to set those parameters or use the tools specifically tailored to his/her needs, the user may want to utilize advanced image processing GUI 301 of advanced image processing system 140. According to one embodiment, the commands and parameters are then provided to image processing engine 104 for processing the images.

The commands may further include other information, such as, for example, a patient ID, a body part ID, if an image is associated with a medical procedure or appointment, a procedure ID or appointment ID, etc. For example, from automatic image processing GUI 302, a user may choose a procedure from within a list of procedures which a patient has undergone. For example, a patient may have a virtual colonoscopy, an EKG and an eye exam listed as procedures he has undergone. The user may choose the virtual colonoscopy. In doing so, automatic image processing GUI 302 of client 300 transfers information to automatic image processing module 304 such as the patient ID, the colon, colonoscopy, date of the procedure or other pertinent information. The automatic image processing module 304 then uses this information to identify the associated image series, as well as the image processing tools associated with the image series. The server 110 also processes the image series and presents the results to the user via automatic image processing GUI 302. The results may include several images including different views, any polyps identified, the size of the polyps, etc.

According to one embodiment, both advanced image processing system 140 and automatic image process system 150 may access the image processing functions (e.g., libraries, routines, tools, etc.) of image processing engine 104 via a set of application programming interfaces (APIs) or communication protocols (if image processing engine 104 is a remote system over a network). When advanced image processing system 140 is utilized, according to one embodiment, advanced image processing GUI 301 may be presented, for example, similar to the graphical user interface as shown in FIG. 8H, to allow the user to specify detailed image processing parameters for processing a specific image selected by the user. The advanced image processing module 303 of advanced image processing system 140 processes the user inputs received from the advanced graphical user interface 301 and formulates one or more image processing commands with a set of image processing parameters that are generated based on the user inputs. The advanced image processing module 303 of advanced image processing system 140 then sends the commands, for example, via the APIs, to image processing engine 104 to process the image. Image processing engine 104 may be implemented using dedicated graphics or image processing hardware, such as graphics processing units (GPUs).

When automatic image processing system 150 is utilized, according to one embodiment, a simplified graphical user interface (e.g., wizard) 302 is presented at client device 300 of the user to walk the user through a series of simple steps or interactive questions without requiring the user to specify the detailed operational image processing parameters. The automatic image processing module 304 is to automatically determine the detailed image processing parameters based on the user interaction with the simplified graphical user interface 302. The user interaction may be captured and received by GUI 302 and transmitted to server 110, for example, as part of image processing indicators. A set of image processing commands is generated based on the user interaction or image processing indicators and sent to image processing engine 104 for processing the image. Alternatively, the automatic image processing module 304 of automatic image processing system 150 determines the parameters and passes the parameters to the advanced image processing system 140, just as the advanced image processing system would have received from a user via its corresponding graphical user interface 301. The advanced image processing module 303 in turn communicates with image processing engine 104 on behalf of automatic image processing system 150. Note that some or all of the components as shown in FIG. 3 may be implemented in software, hardware, or a combination thereof.

According to one embodiment, an example of image processing operations may be a flythrough procedure for identifying and measuring a polyp in an image. Typically, when a user uses the advanced image processing system 140, the corresponding advanced image processing GUI 140 provides more fields and buttons, such as image processing tools similar to those as shown in FIG. 8H, to allow the user to specify the parameters and tools to be used to process an image. As a result, the user has to be an advanced user who is familiar with the software and/or tools. For example, a user may have to select, amongst others, the tool of "pick polyp" to identify a polyp from an image, location, and/or size or shape of a polyp. Based on the selection, a polyp identifier, as well as its location within the image may then be transmitted to an image processing engine to measure the size of the selected polyp, etc.

When automatic image processing system 150 is utilized, a user does not have to specify at least some of the parameters and/or tools as required when using advanced image processing system 140. Once the user identifies a patient (possibly by being logged into their EMR account) and either identifies a body area (abdomen) or procedure (flythrough), according to one embodiment, automatic image processing system 150 generates the flythrough results automatically, including initial identification of polyps. The user may then provide feedback on the number and location and size of the polyps which have been automatically detected, located, and measured. In one embodiment, the user is given a chance to review whether the automatic image processing system has accurately performed the intended operations. For example, when an image processing operation associated with a flythrough of polyps, when displaying the results, the automatic image processing system prompts the user whether the polyps have been correctly identified (e.g., number of polyps), as well as their locations and sizes, etc. A set of simple choices or questionnaires may be presented to the user for further user inputs. Based on the further user inputs, the automatic image processing system can reprocess the image according to the further user inputs. It is possible if the user clicks on the abdomen, there may be more than one imaging procedure associated with the abdomen and the user may need to identify flythrough as the result he/she wants to see. In one embodiment, automatic image processing system 150 invokes image processing engine 104 to automatically determine a location of polyps, number of polyps, size and volume of polyps, and possible change in polyps amongst multiple images.

Image processing engine 104 can differentiate between different tissue types and densities. It also knows generally where certain anatomy is based, for example, on landmarks or shape atlases etc. For example, image processing engine 104 includes certain graphics logic or functions (e.g., image processing algorithms or routines) to process (e.g., comparing, filtering, transforming) the pixel values to detect an edge or area of a particular shape, perform a pattern recognition of the detected shape or area to identify a particular type of body part or organ (e.g., heart, polyp), and measure the size of the shape or area, etc. Once it segments (draw outlines) and identify shapes, it can take measurements and perform a predetermined algorithm, etc. It is programmed to show certain types of views depending on what it finds. For example, it would show the colon flythrough if polyps were found, or dimensions of heart vessels if stenosis were found, or various tumor slices if tumors were found. The user choosing a body area and/or procedure helps the system narrow down its analysis.

Another example of image processing operations is stenosis measurement (e.g., in a heart vessel). Again, when advanced image processing system 140 is utilized, a user has to select the proper tool for stenosis measurement, as well as, the location or size of the measurement to be performed. When automatic image processing system 150 is utilized, the user only has to identify the heart, and/or "stenosis" information to receive the results. In response, the backend system, such as image processing engine 104, is automatically able to locate the blood vessels, measure them, locate a narrowing, and perform an algorithm or calculation on what percentage the narrowing is. The user can adjust these measurements if he/she wants to, for example, moving the outline of the vessel so that it is more accurate. The system can automatically determine vessel segmentation (outline) for all vessels, vessel diameters, diameter narrowing, percent diameter narrowing, possible change in stenosis amongst multiple images.

Another example of image processing operations is related to tumor volume measurement. For example, for a brain tumor, a user can click on the head, and depending on what imaging procedures have been done on the brain, the automatic image processing system automatically generates the brain tumor results (if this is the only procedure), or asks the user to choose which procedure he/she wants (for example, there may be an aneurism scan also). The system can automatically find the location of the tumor, draw the volume outline (segment the tumor) and provide the volume of the tumor.

Figure 4:
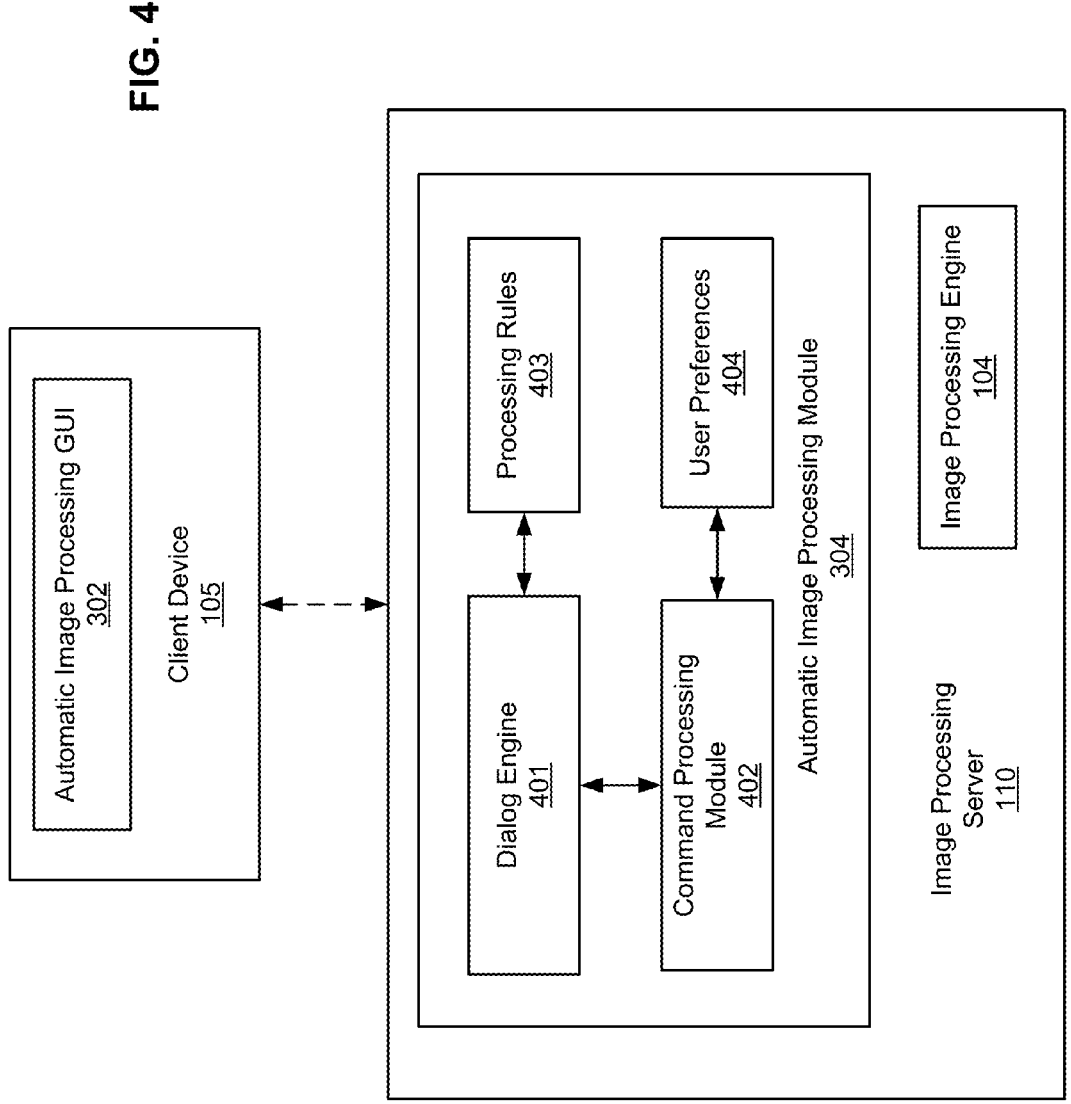
FIG. 4 is a block diagram illustrating an example of an automatic image processing module according to one embodiment of the invention.

FIG. 4 is a block diagram illustrating an example of an automatic image processing module according to one embodiment of the invention. Referring to FIG. 4, automatic image processing module 304 includes dialog engine 401 and command processing module 402. These modules may be implemented in software, hardware, or a combination thereof. In one embodiment, dialog engine 401 communicates via GUI 302 with a user in a dialog format by presenting a series of questions based on a set of processing rules 403. The answers received from the user may be analyzed by dialog engine 401 or another analysis module (not shown) to determine a set of image processing operations. The image processing operations may be determined based on body part, procedure, appointment, condition etc. A user intent is then determined based on the answers received from the user. The user intent may be interpreted based on user preferences 404 or prior user interactions in addition to data such as body part, procedure, appointment, condition etc.

According to one embodiment, GUI 302 presents various user selectable tags, which may be associated with body areas, medical procedures, medical appointments, and/or medical conditions, for example, as shown in FIGS. 7A-7D. Each of the tags displayed may be associated with or interpreted as an image processing indicator that indicates a specific type or types of image processing operation or operations. In response to a user selection of one or more image processing indicators, a set of image processing parameters may be automatically determined, without user intervention, by command processing module 402. The parameters are then utilized by image processing server 110, for example, via image processing logic 310. For example, when automatic image processing system 150 is invoked by a user, dialog engine 401 may prompt the user for what the user wants to do. The user can select the images based on body parts, medical procedures, medical appointments, and medical conditions of a patient. Based on the user selection, dialog engine 401 can present further questions concerning the image processing operations that may be needed or recommended, etc. to walk the user through an automatic processing timeline, without having the user deep dive and get overwhelmed by the image processing details.

Figure 5:
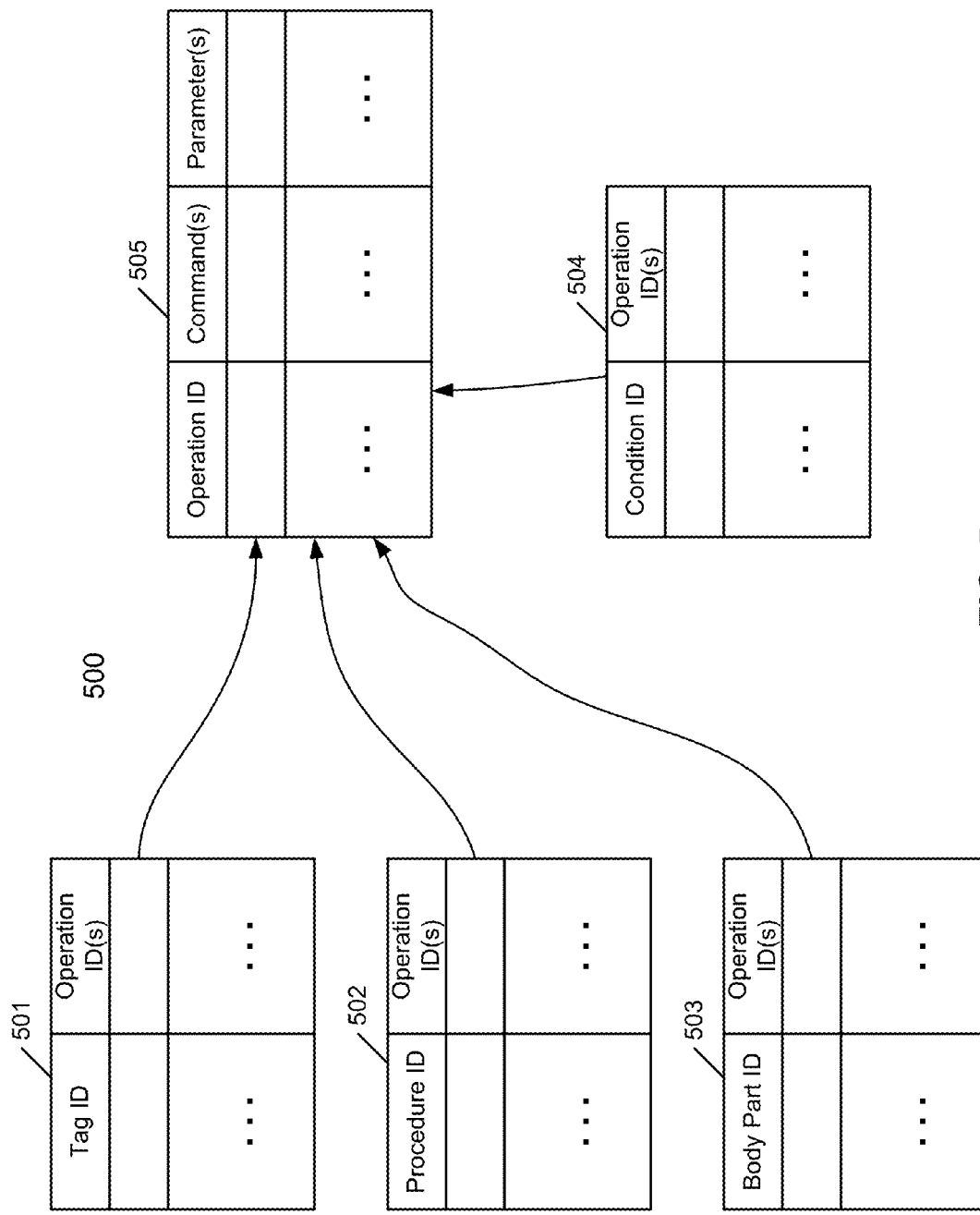
FIG. 5 is a block diagram illustrating an example of processing rules of an automatic image processing system according to one embodiment of the invention.

FIG. 5 is a block diagram illustrating an example of processing rules of an automatic image processing system according to one embodiment of the invention. Referring to FIG. 5, rules 500 may be implemented as a part of processing rules 403 stored in a persistent storage device (e.g., hard drive) and/or loaded into a system memory accessible by automatic image processing module 304 at server 110 of FIG. 4. In this example, rules 500 include tables or data structures 501-505 to determine a set of one or more image processing operations based on a variety of categories of information, which may be represented by image processing indicators received from a client device, where may be determined based on user interactions with respect to content presented in a graphical user interface displayed at the client device. An image processing indicator may represent a patient ID, a body area ID, a medical procedure ID, a medical appointment ID, a medical condition ID, or a combination of any of these IDs. For example, the image processing operations may be determined based on tags via data structure 501, medical procedures via data structure 502, body parts via data structure 503, and medical conditions via data structure 504. Once the image processing operations are determined, the associated image processing commands and their respective parameters can be identified via data structure 505. The information stored in data structures 501-505 may be implemented in a database and user configurable, for example, by an administrator, via a configuration interface of server 110. Such information may be stored in and retrievable from server 110 via a set of application programming interfaces (APIs) or communication protocols over a network. Similarly, any user preferences or prior interaction may also be recorded in the server 110.

Figure 6:
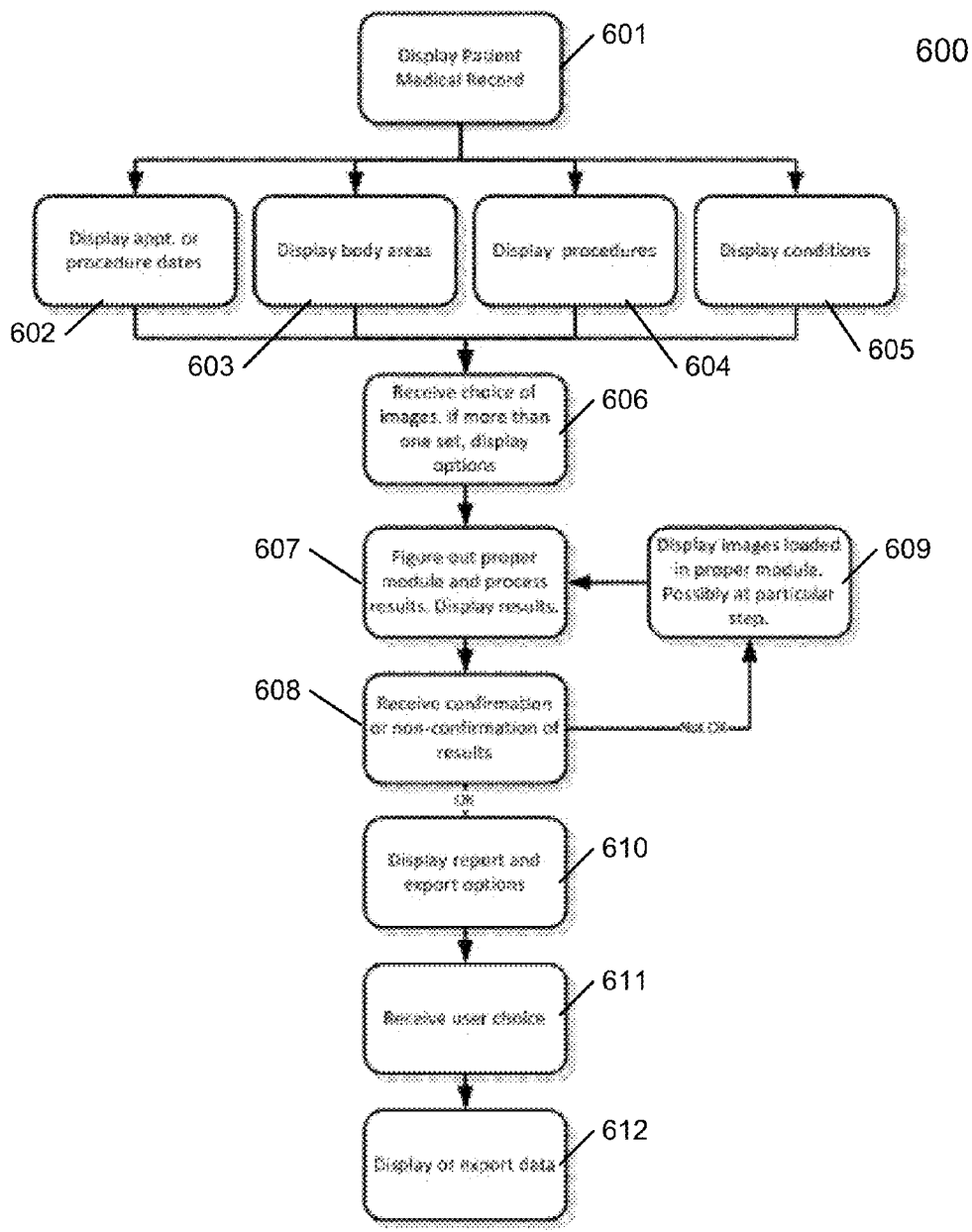
FIG. 6 is a flow diagram illustrating a processing flow of an automatic image processing system according to one embodiment of the invention.

FIG. 6 is a flow diagram illustrating a processing flow of an automatic image processing system according to one embodiment of the invention. Referring to FIG. 6, at block 601, a medical record of a patient is displayed, where the medical record may be obtained from a MRCS server. The medical record may be obtained by a dedicated module, such as a data integration engine, of image processing server 110 that is communicatively coupled to the MRCS server, where the data integration engine communicates with various information sources to retrieve and to integrate various types of medical and/or image information. Dependent upon what the user wants, the medical record can be displayed in a form of medical appointments in block 602, body areas in block 603, medical procedures in block 604, and medical conditions in block 604, or in any other appropriate manner. At block 606, a user selection is received. Image processing operations are determined and performed by an image processing server at block 607. The processing results are presented to the user at block 608 and if the user is unsatisfied with the results, the image processes can be iteratively performed via block 609. At block 610, certain export options can be presented to the user for selection at block 611, and the data can be displayed or exported at block 612.

FIGS. 7A-7D are screenshots illustrating examples of graphical user interface of an automatic image processing system according certain embodiments of the invention. GUIs as shown in FIGS. 7A-7D may be generated by server 110 and received and presented by client 105 of FIG. 3. User interactions with the GUIs are captured and transmitted from the client device to image processing server 110. The user interactions are then interpreted or analyzed by image processing server 110 and in response to the user interaction, image processing server 110 performs proper actions, such as, image processing operations, information retrieval operations, and data processing and/or integration operations, and returns processing results back to the client. The processing results are presented and/or integrated with the existing information at a display device of the client.

Figure 7A:
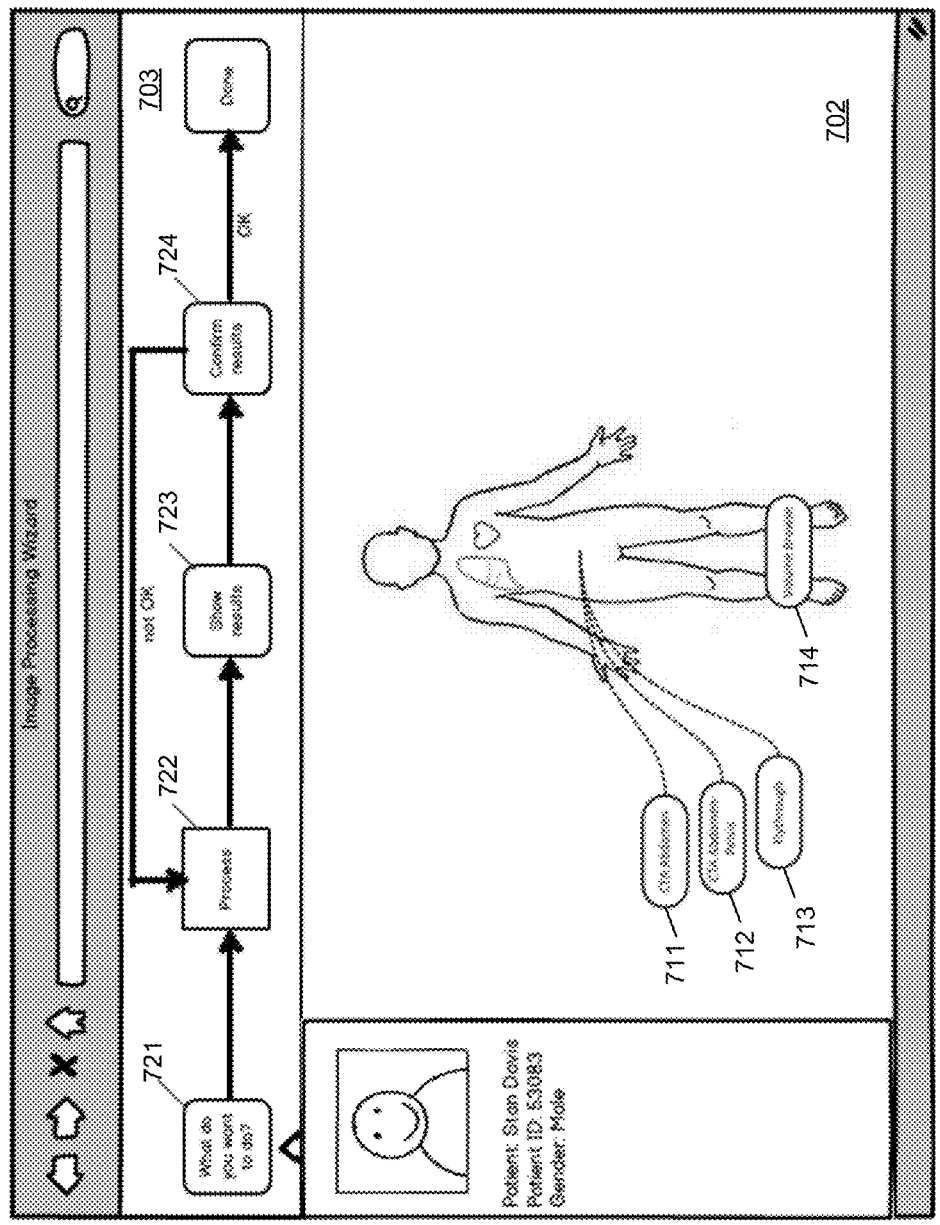
FIGS. 7A-7D are screenshots illustrating examples of graphical user interface of an automatic image processing system according certain embodiments of the invention.

Referring to FIG. 7A, the GUI includes a first display area 701 to display patient identifying information, a second display area 702 to display detailed information about the patient, and a third display area 703 to display an image processing timeline. The GUI shows one way to access imaging data that is associated with a particular patient. In this example, a user can access medical data via body areas. A representation of a human body 710 is shown with selectable tags 711-714, such as CTA Abdomen tag 711 and Flythrough tag 713, where imaging procedures have been performed on this patient. In this example, this patient has had imaging procedures associated with the abdomen/Pelvis, but not with other areas of the body, such as the brain. If imaging data were available for the brain, a tag would show up in a location associated with the brain area. The medical record information such as patient information may be obtained by server 110, where server 110 may be integrated with a medical record server or communicatively coupled to the medical record server.

These image tags 711-714 are selectable, which when selected will bring the user to another screen which will provide more information and/or questions about the particular body part/procedure selected. For example, when a user selects or clicks one of the tags or items, a signal representing the selected tag or item is transmitted from the client to image processing server 110. In response to the signal (e.g., image processing indicator), image processing server 110 performs proper actions, which may include an image processing operation and/or information retrieval operation. The results of the actions are then transmitted from image processing server 110 back to the client and presented to the user via the GUI interface. Across the top of the GUI is timeline 703, or process line, or workflow, of the image data viewing/processing process. Timeline 703 includes multiple graphical representations 721-724 representing different processing stages within the timeline. In this example, the user is currently at the "what do you want to do?" stage 721. At this stage, the user chooses what type of image data he/she wants to view/process. The timeline 703 shows that subsequent steps will include processing image stage 722, showing result stage 723, determining whether the results are acceptable or unacceptable stage 724, and finishing the process at the end.

Figure 7B:
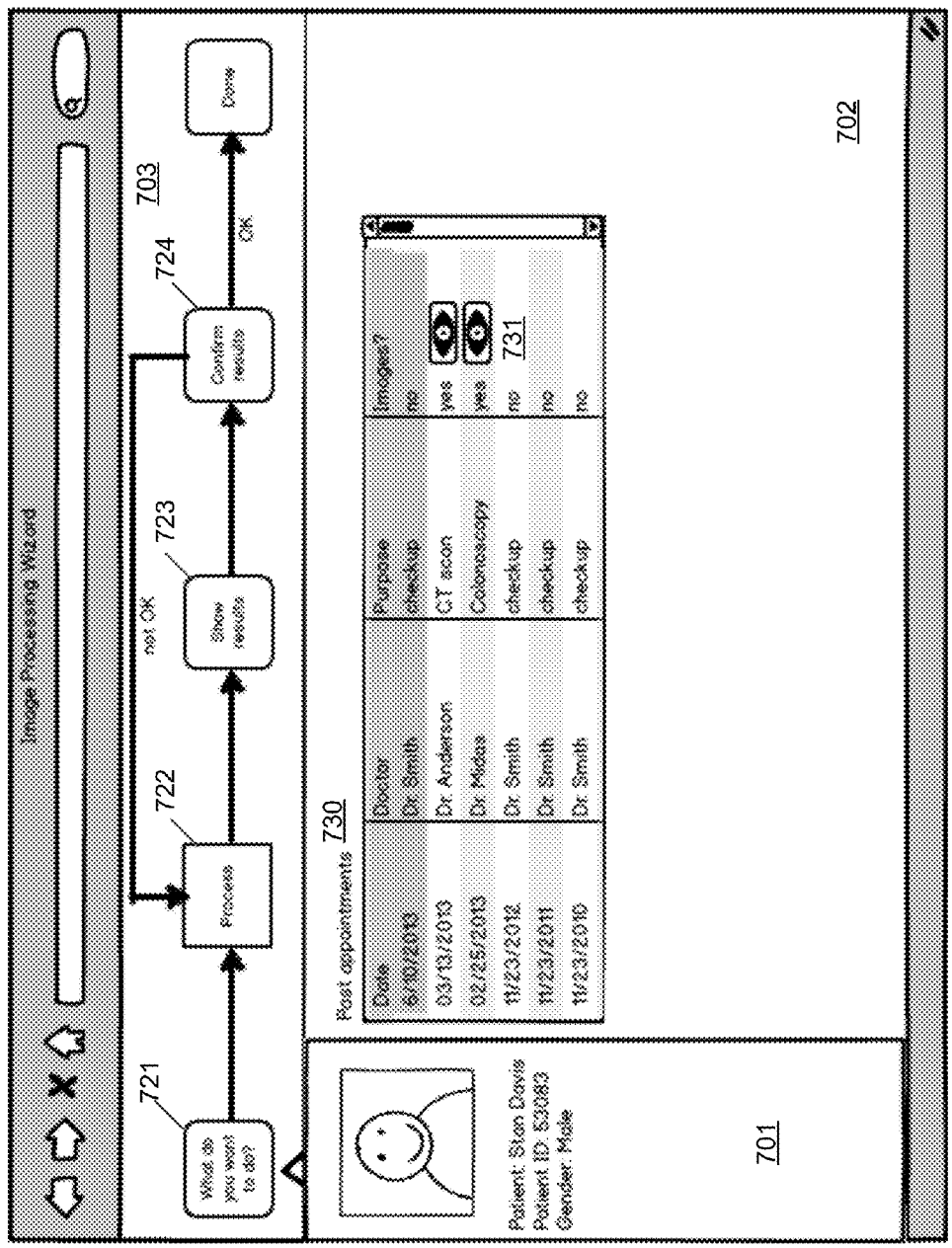

Referring now to FIG. 7B, this GUI shows another way to access imaging data that is associated with a particular patient. The method of accessing image data shown in FIG. 7B is by appointment history. For example, a user may log into image processing server 110 and elect to view images based on medical appointment history, for example, by clicking a corresponding link or button (not shown). A list of past appointments 730 is shown, along with a link to image data if any image data is associated with the appointment. In this example, the patient has had a CT scan and a Colonoscopy, both of which have associated image data which is represented by a graphical representation 731, in this example, an "eye" icon. Other appointments, such as routine checkups, in this example, do not have associated image data. The graphical representation 731 in this example are selectable and will bring the user to another screen which will provide more information and/or questions about the particular image data associated with the appointment.

Figure 7C:
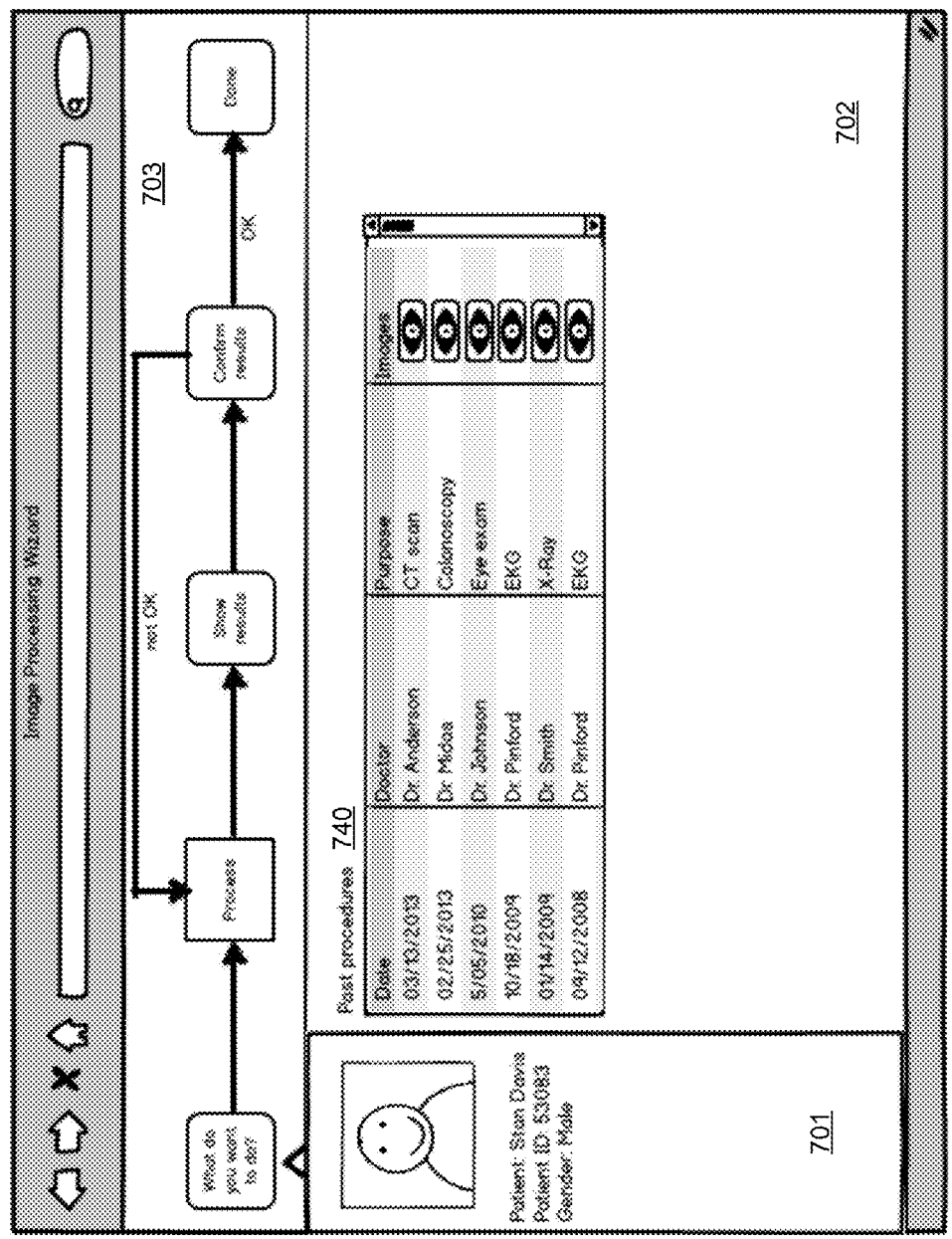

Referring now to FIG. 7C, this GUI shows another way to access imaging data that is associated with a particular patient. The method of accessing image data shown in FIG. 7C is by procedure history 740. A list of past procedures is shown, along with a link to image data if any image data is associated with the procedure. In this example, the patient has had a CT scan and a Colonoscopy in addition to other procedures. These procedures have associated image data which is represented by a graphical representation such as an "eye" icon. The "eye" icons in this example are clickable and will bring the user to another screen which will provide more information and/or questions about the particular image data associated with the procedures.

Figure 7D:
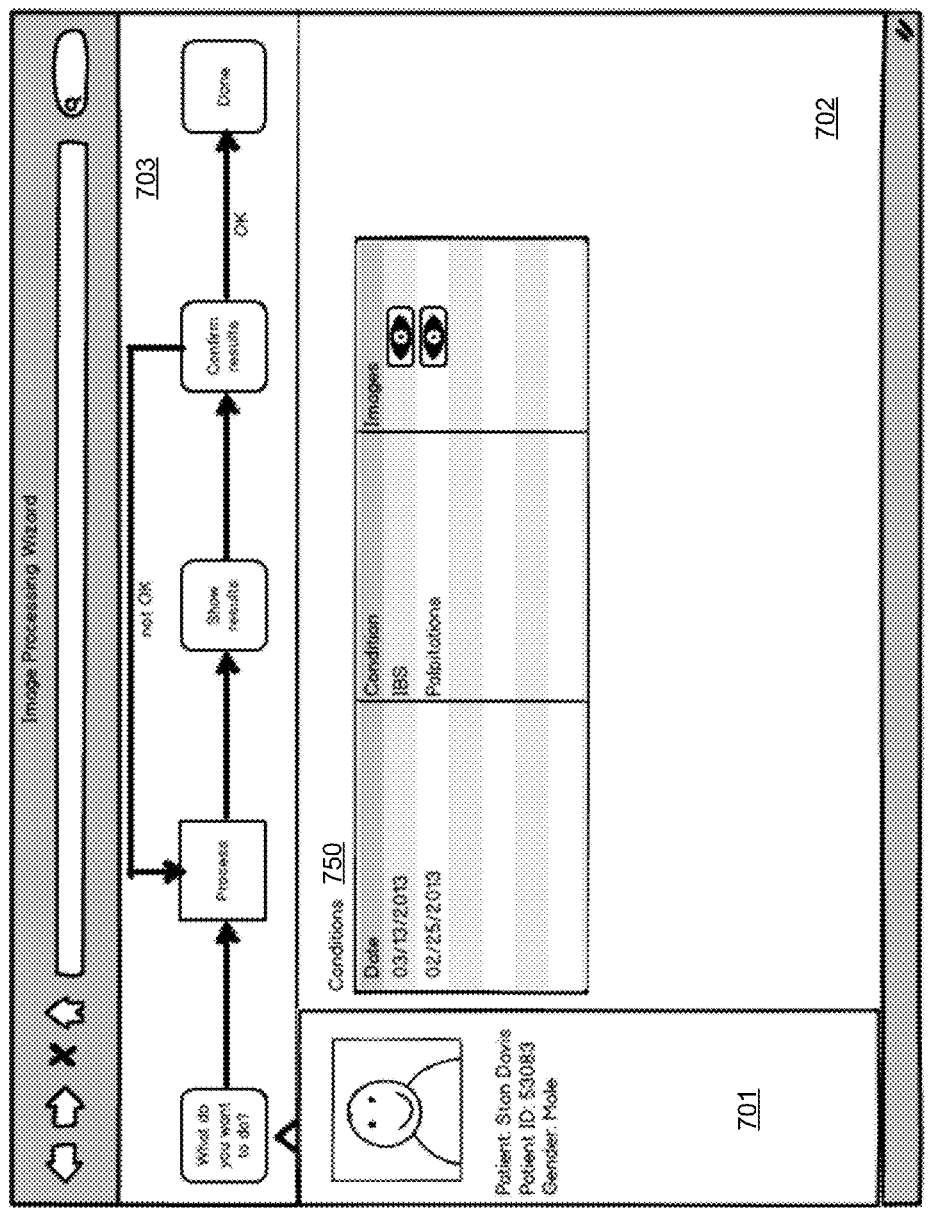

Referring now to FIG. 7D, this GUI shows another way to access imaging data that is associated with a particular patient. The method of accessing image data shown in this Figure is by conditions. A list of conditions associated with this patient is shown, along with a link to image data if any image data is associated with the condition. In this example, the patient has been diagnosed with IBS and Palpitations. Both of these conditions have associated image data which is represented by a graphical representation or link such as an "eye" icon. The "eye" icons in this example are clickable and will bring the user to another screen which will provide more information and/or questions about the particular image data associated with the condition.

As shown in FIGS. 7A-7D, a user can utilize an automatic image processing GUI of the automatic image processing system (e.g., system 150) to start with the information of a medical record of a patient. When a medical record is presented, the automatic image processing module 304 is to determine whether there are images associated with the medical information of the medical record. If so, automatic image processing module 304 causes the corresponding automatic image processing GUI to display a graphical representation at the client device indicating that one or more images are available for that particular medical record data (e.g., body area, procedure, condition, appointment).

A user can access the associated medical images by activating (e.g., clicking) the corresponding links or graphical representations. After the user activates on the link to image data (in this example, clicking on an "eye" icon), the user may be brought directly to image processing result stage 723, or may be asked more questions. For example, if there is more than one sets of images associated with the body part, appointment, procedure, and/or condition etc., the user may be asked to choose which set of images he/she wants to analyze. Also, there may be other questions relating to settings, parameters, processing preferences etc. for example, the user, after clicking on images associated with a colonoscopy, may be asked what type of views he/she prefers. The user may be given the option to have the system "remember" his/her preferences so he/she doesn't have to answer the question every time he/she wants to analyze similar image sets. For example, the system may present a checkbox which states "always use this setting for this type of image" or similar. Such user preferences may be transmitted back to the image processing server and stored therein. The user preferences can be retrieved when the same user subsequently logs into the image processing server.

According to one embodiment, the interaction, i.e., dialog, between the system and the user may be handled by dialog engine 401 of FIG. 4. Based on the user interactions, the user behaviors are analyzed to determine the proper actions to be taken. For example, based on the particular body area, body part, medical procedure, and/or medical condition, certain image processing operations may be identified that can be performed on the associated images. The image processing operations may be recommended to the user. Alternatively, such image processing operations may be automatically performed without user intervention or knowledge. In this embodiment, an analysis module (not shown) analyzes the user interactions provided by the dialog engine and determines one or more image processing operations (e.g., measurements). The underlying command processing module 402 generates the proper image processing commands and transmits the commands to image processing engine 104 for image processing. When the image processing results are received from image processing engine 104, the results are then transmitted back to client 105 and presented via the automatic image processing GUI 302 as part of show result stage 724.

FIGS. 8A-8K are screenshots illustrating examples of graphical user interface of an automatic image processing wizard according certain embodiments of the invention. GUIs as shown in FIGS. 8A-8K may be generated by automatic image processing system 150 and received and presented by automatic image processing GUI 302 of FIG. 3. User interactions with the GUIs are captured and transmitted from the client device to image processing server 110. The user interactions are then interpreted by image processing server 110 and in response to the user interaction, image processing server 110 performs proper actions, such as, image processing operations, information retrieval operations, and data processing and/or integration operations, and returns processing results back to the client. The processing results are presented and/or integrated with the existing information at a display device of the client.

Figure 8A:
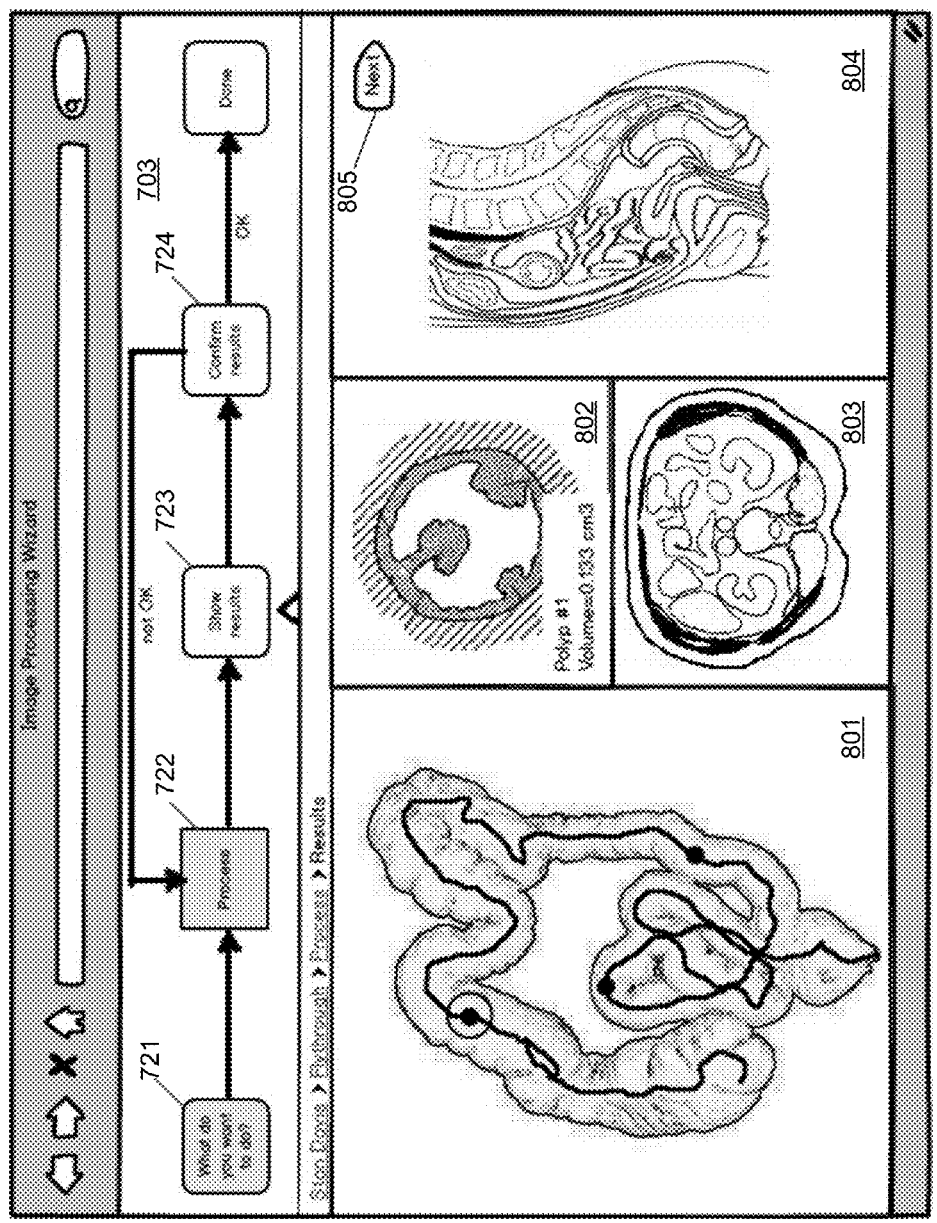
FIGS. 8A-8K are screenshots illustrating examples of graphical user interface of an automatic image processing system according certain embodiments of the invention.

FIG. 8A shows an example of a results screen that is part of show result stage 823, indicated as a current processing stage. In this example, the user has clicked on an image data link associated with the abdomen, and more specifically, a colonoscopy flythrough, of the patient. The image data link may be presented in any of GUIs as shown in FIGS. 7A-7D. A signal representing the user action (e.g., clicking the image data link) is transmitted from the client to the image processing server 110. For example, the signal may include an identifier identifying a corresponding body part (e.g., abdomen) and/or a medical procedure (e.g., colonoscopy flythrough). The image processing server processes the signal, performs proper operations, and generates results. The results are then transmitted from image processing server 110 back to the client to be presented to the user. In this example, the results show three identified polyps in display area 801, along with several different views of the intestines and polyps, and quantitative data for the polyps, such as volume, in display areas 802-804. In this example, the image processing results were performed automatically, without user intervention, by the image data processor at the image processing server 110. The user may have the ability to set user preferences or settings that are applied to the automatic image processing.

If the user highlights one of the polyps in display area 801, he/she can see the location in the anatomy where the polyp was found from different perspectives, as well as quantitative data, in display areas 802-804. In this way, the results can be fully analyzed and reviewed. Note that the timeline 703 on the top of the screen shows where in the process the user is. Since this is the results screen, the timeline shows that the processing has already taken place and the user is now viewing the results of the image processing at stage 723. When the user is finished reviewing the results, he may click on the "next" button 805 to go to the next step, confirm result stage 824.

Figure 8B:
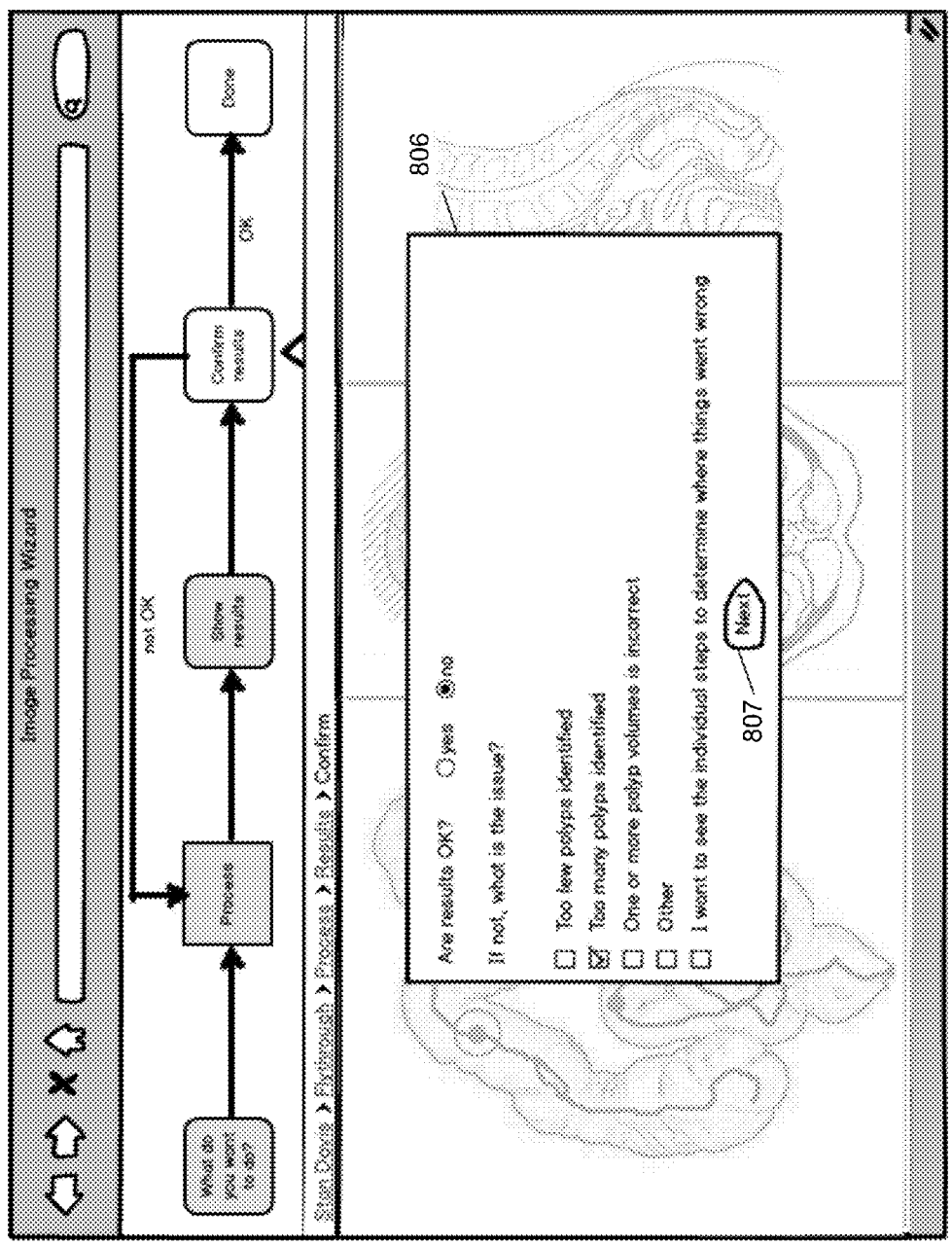
Figure 8C:
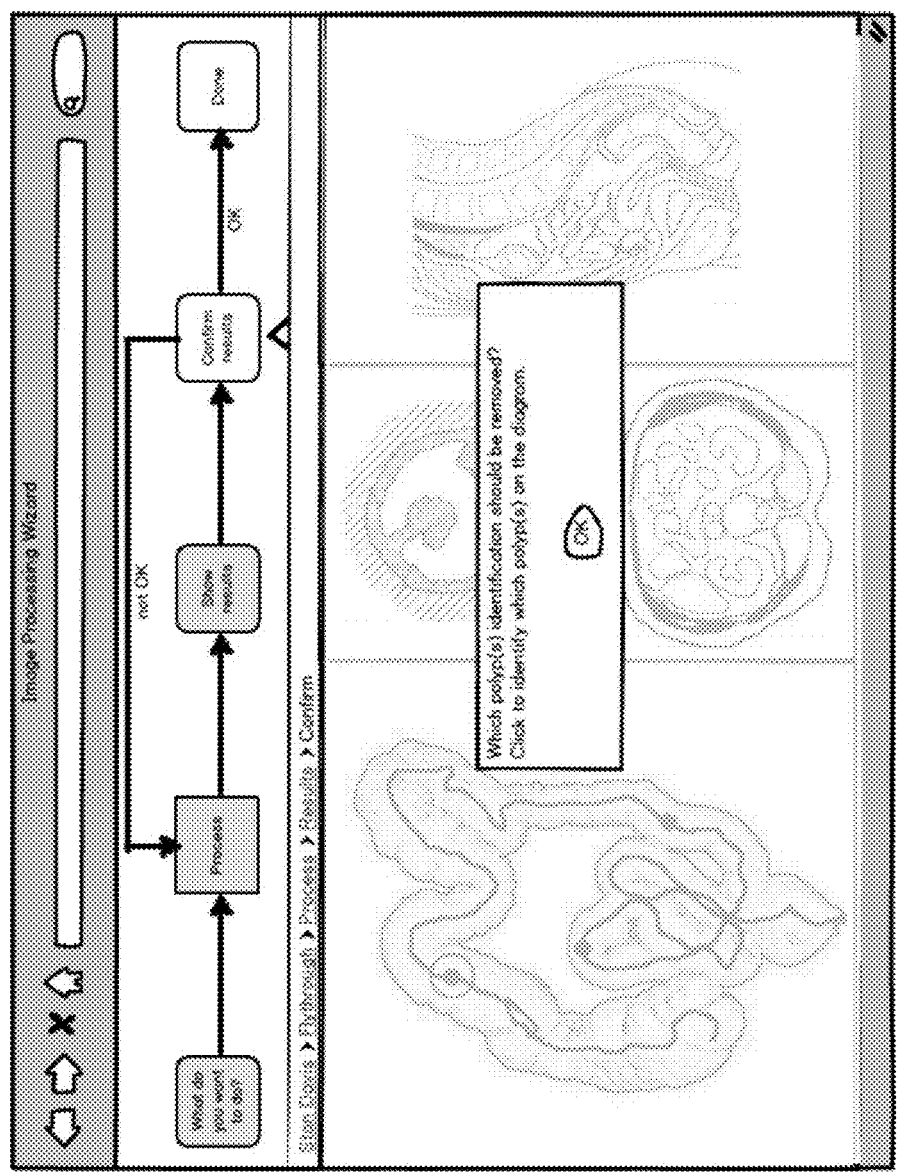

FIG. 8B shows an example of a wizard pop-up window 806 which helps the user either confirm the image data processing results, or improve the results, which is a part of confirm stage 724 in response to an activation of next button 805. The wizard pop window 806 is generated by the image processing server 110 and received at a client to prompt the user to confirm whether the image processing results are correct or accurate. In this example, the user has determined that the image processing results included too many polyps. This could happen of the image processing system miss-identified one or more polyps. After the user hits the "next" button 807, he or she may be taken to a screen such as the one shown in FIG. 8C, which shows the automatic image processing system asking the user which polyp(s) he/she does not believe should be identified as such.

Figure 8D:
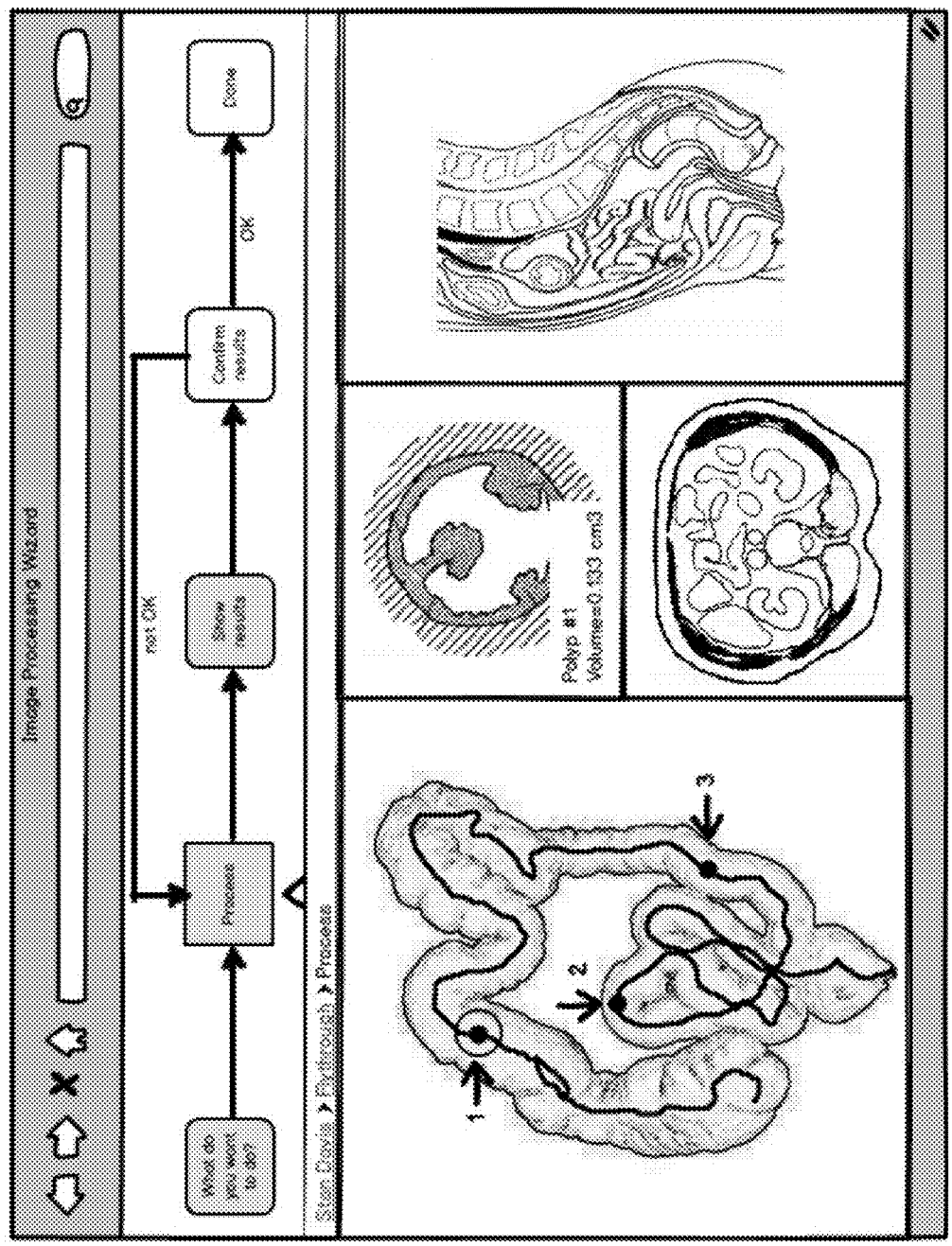
Figure 8E:
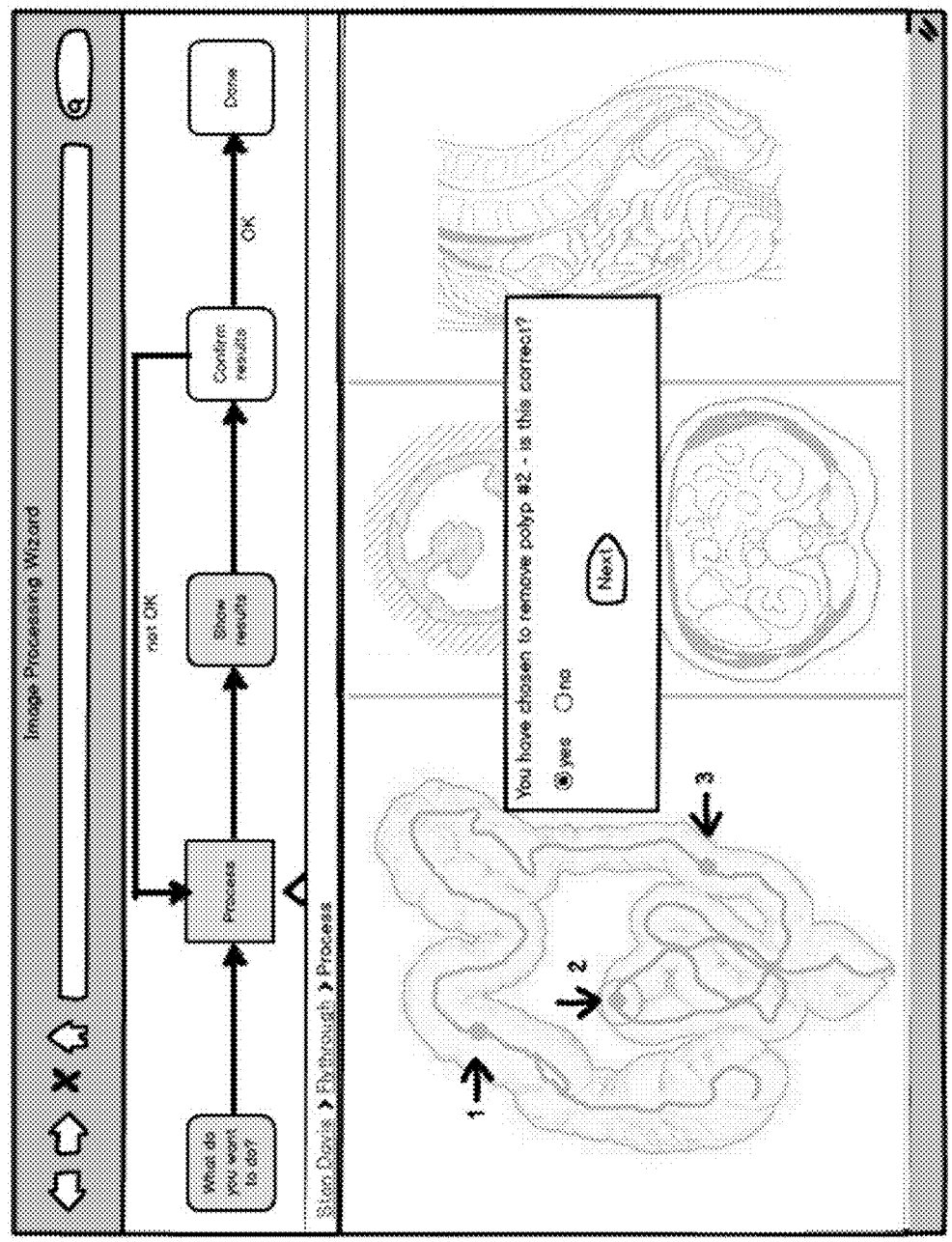

FIG. 8D shows an example of a screen that the user may see to help him/her identify the incorrectly identified polyp (s). In this example, the user can click on any one of the 3 polyps to identify it as the incorrect one, where these polyps are automatically identified by the wizard. The user can also view more detail associated with any individual polyp by highlighting the polyp. In this example, the user has highlighted polyp 1 to view more detail/views. In response, the volume of the polyp 1 is shown in a different display area, which is measured by the image processing system automatically. The user clicks on the number 2 to identify polyp 2 as the incorrectly identified polyp. After the user identifies polyp 2, he/she may be shown a screen similar to that in FIG. 8E, asking the user to confirm that he/she has chosen polyp number 2 to be removed.

Figure 8F:
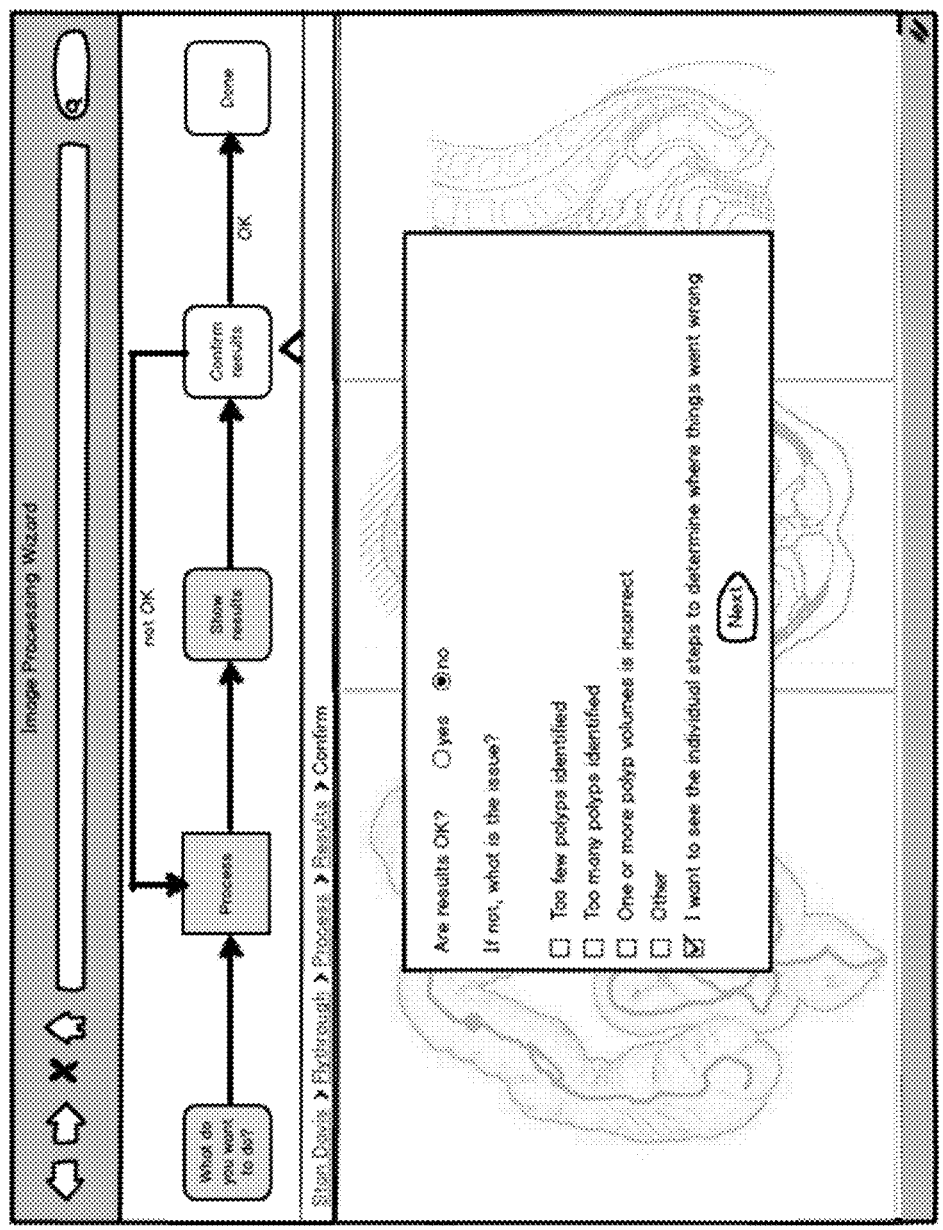

FIG. 8F shows a screenshot similar to that in FIG. 8B. Note that in this example the user is still not satisfied with the results, but has checked a different box: "I want to see the individual steps to determine where things went wrong". This option may be available to the user based on user privileges. This will take the user to a more advanced screen, such as FIG. 8G, which will allow the user to evaluate each step that the system has processed and review and make changes to any steps that require changes.

Figure 8G:
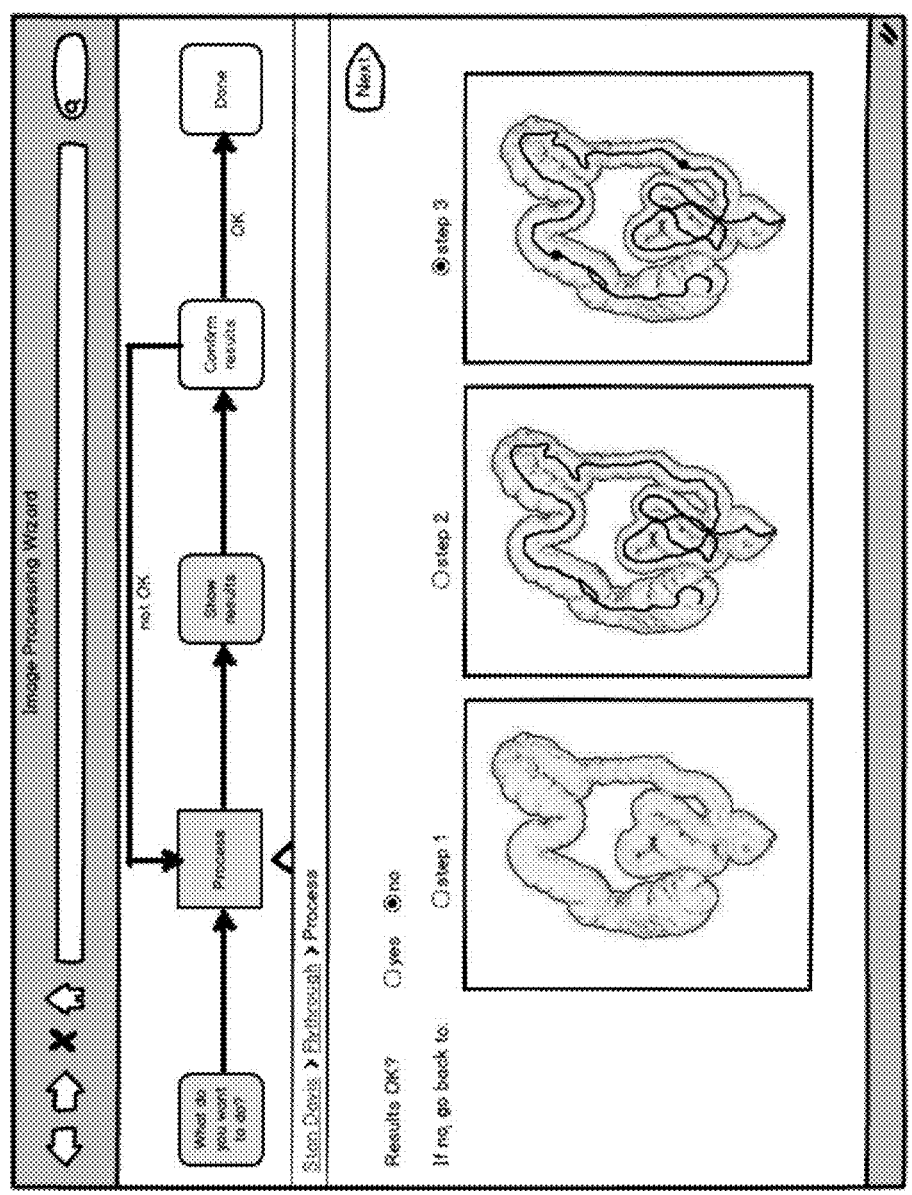
Figure 8H:
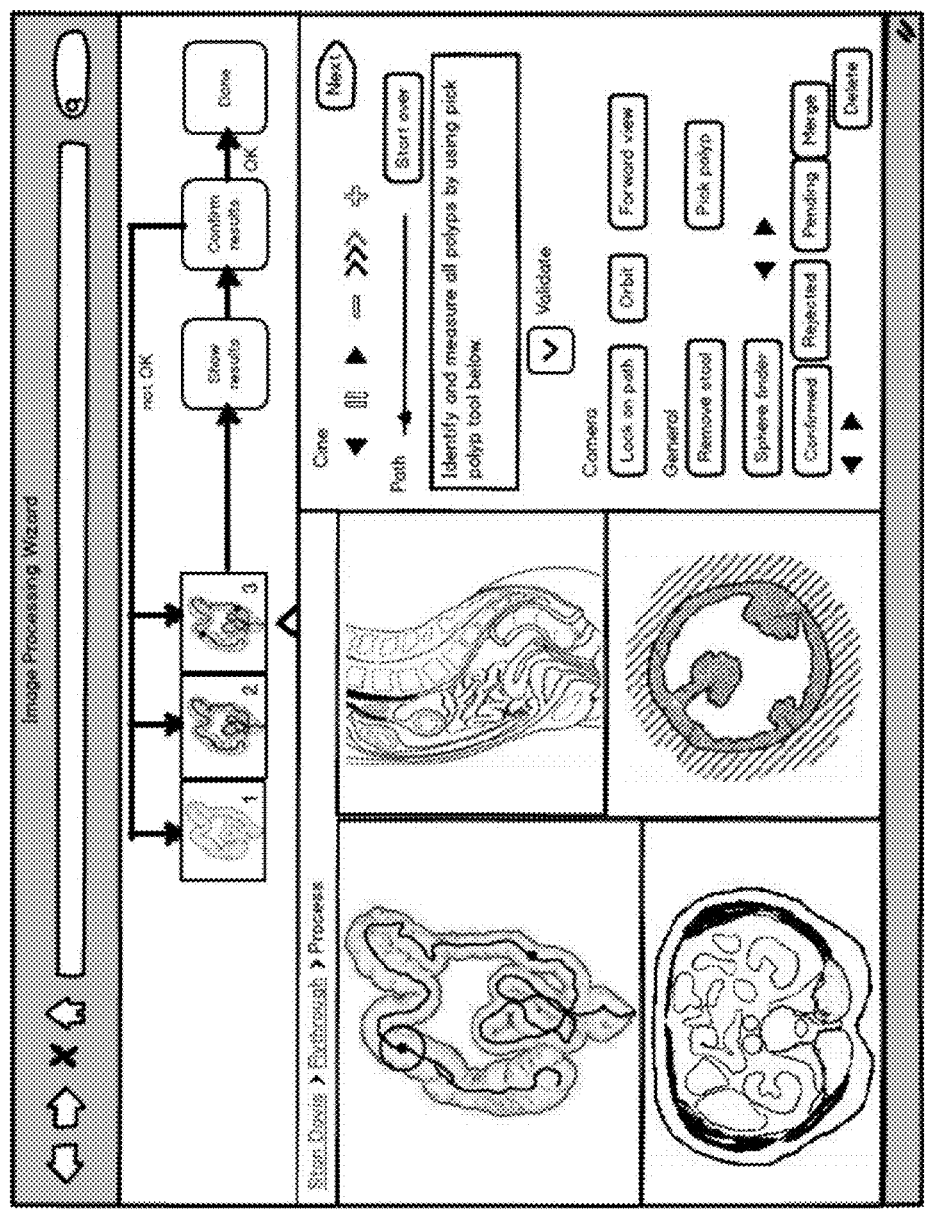

FIG. 8G shows image representations of the various steps that the image processing system has performed to obtain the image processing result. This example GUI shows three steps but there may be fewer or more steps shown. The three steps shown here depict the identification of the colon, the colon centerline, and the identification of potential polyps in the colon, which are identified automatically by the automatic image processing system. The user may click on any of these steps to change the results. If the user changes the results of one step, the changed data will be propagated through the following steps when the image data is again processed. For example, if the user were to change the colon definition in step one, by, for example, extending it or reducing its length, a different centerline and possibly different polyps would be identified in subsequent steps as a result in the changed colon length. The data is passed from a step to subsequent steps in meta-data associated with the image data. In this example, the user has chosen step 3 to analyze further.

FIG. 8H shows a more advanced screen for analyzing and possibly altering the image data. In this example, the user is reviewing step 3. The user has access to more advanced tools on this screen and can define various parameter of the polyps. According to one embodiment, access to this screen may be limited to users who have been trained to use these advanced image processing tools (e.g., certain user privileges). The user has the ability to move among different steps by clicking the thumbnails that have now appeared in the timeline at the top of the screen. Advanced tools may be presented for the different steps, although the tools may be different for each step. The availability of the tools may be determined by the image processing server based on the types of the images, or the body parts, medical procedures, medical conditions associated with the images. The user may choose to step through every step to confirm that the processing has been done accurately. Note that the GUI as shown in Figure H may be displayed by advanced image processing user system 140, which may be invoked from the automatic image processing user system 150.

Figure 8I:
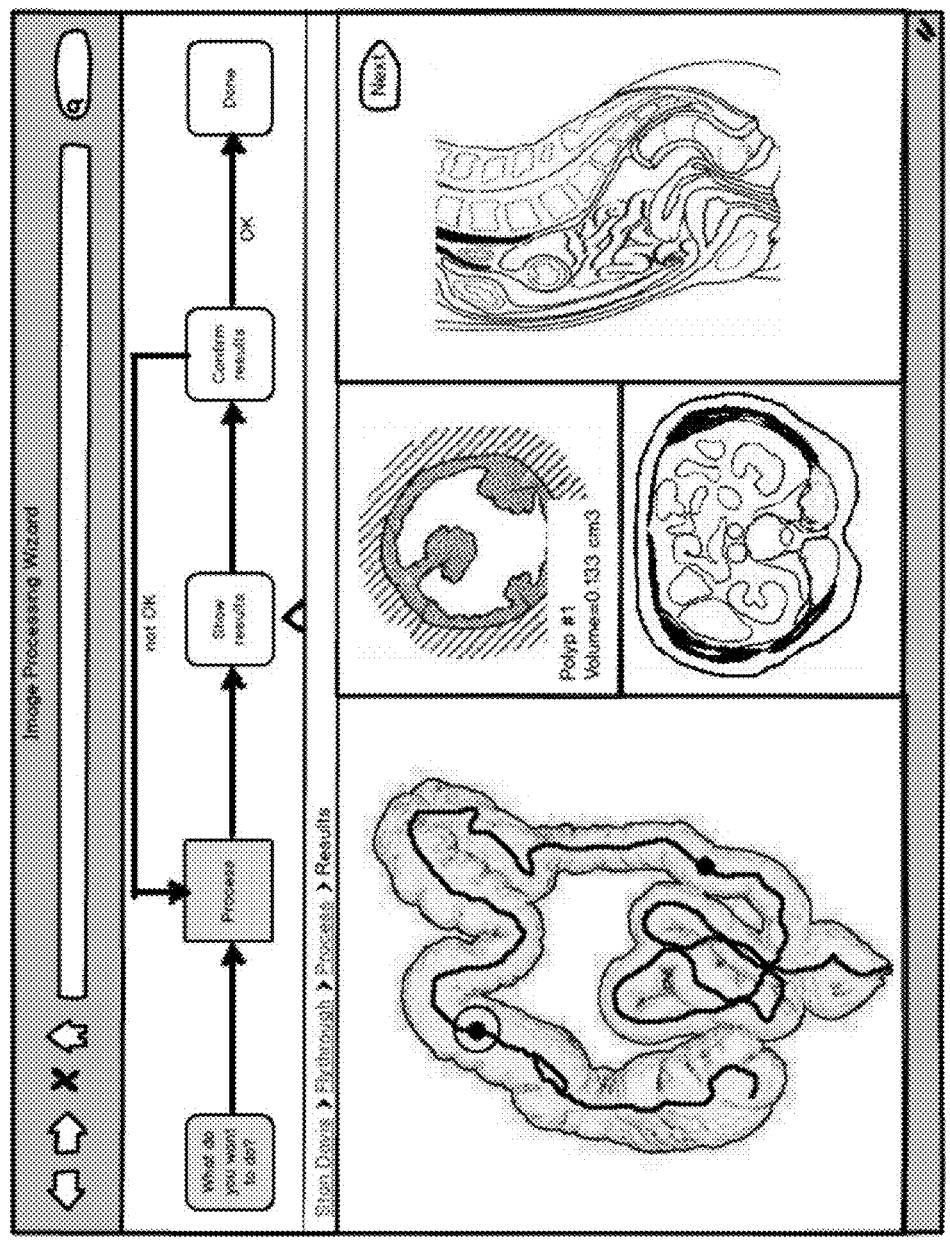
Figure 8J:
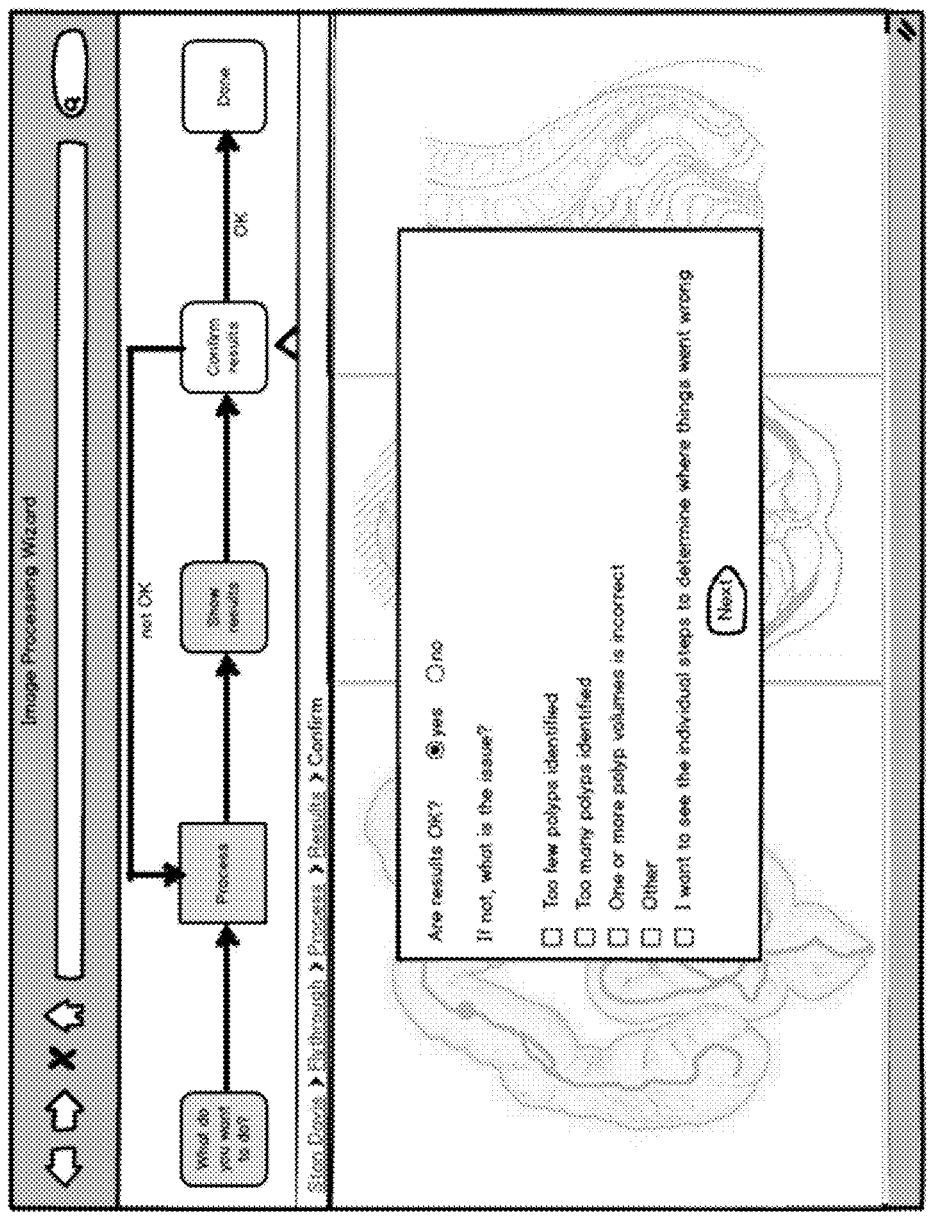
Figure 8K:
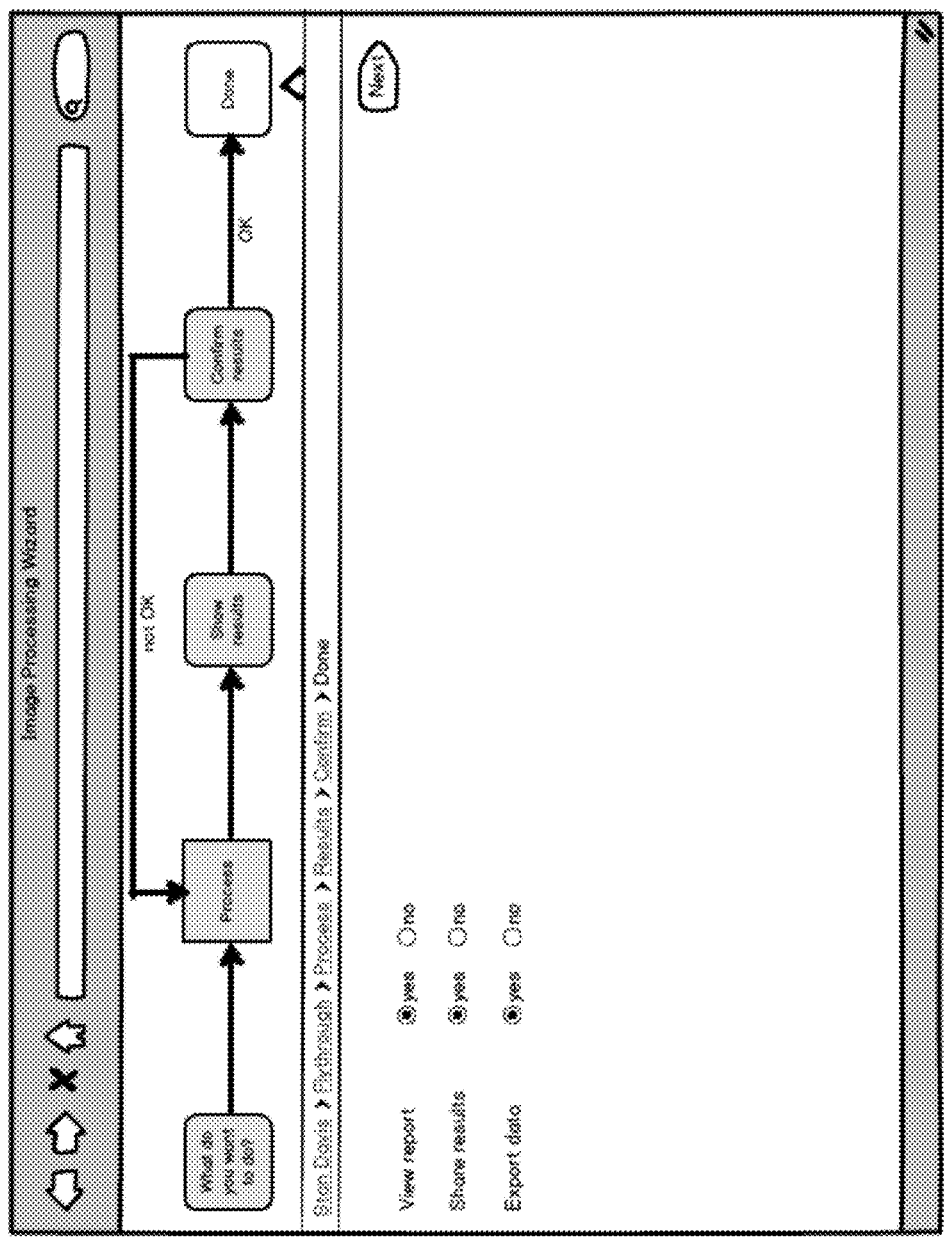

FIG. 8I shows the results of the user's changes to the various image processing steps. If no changes were made, the results will not change. FIG. 8J shows a results confirmation wizard pop-up window again. This time the user has indicated that the results are OK. FIG. 8K shows some example options available to the user after the image processing results have been confirmed. Options include report generation, sharing the results with other physicians, patients or others, and exporting the data in various formats including xml, csv, html and other formats. Other options may be available.

Figure 9A:
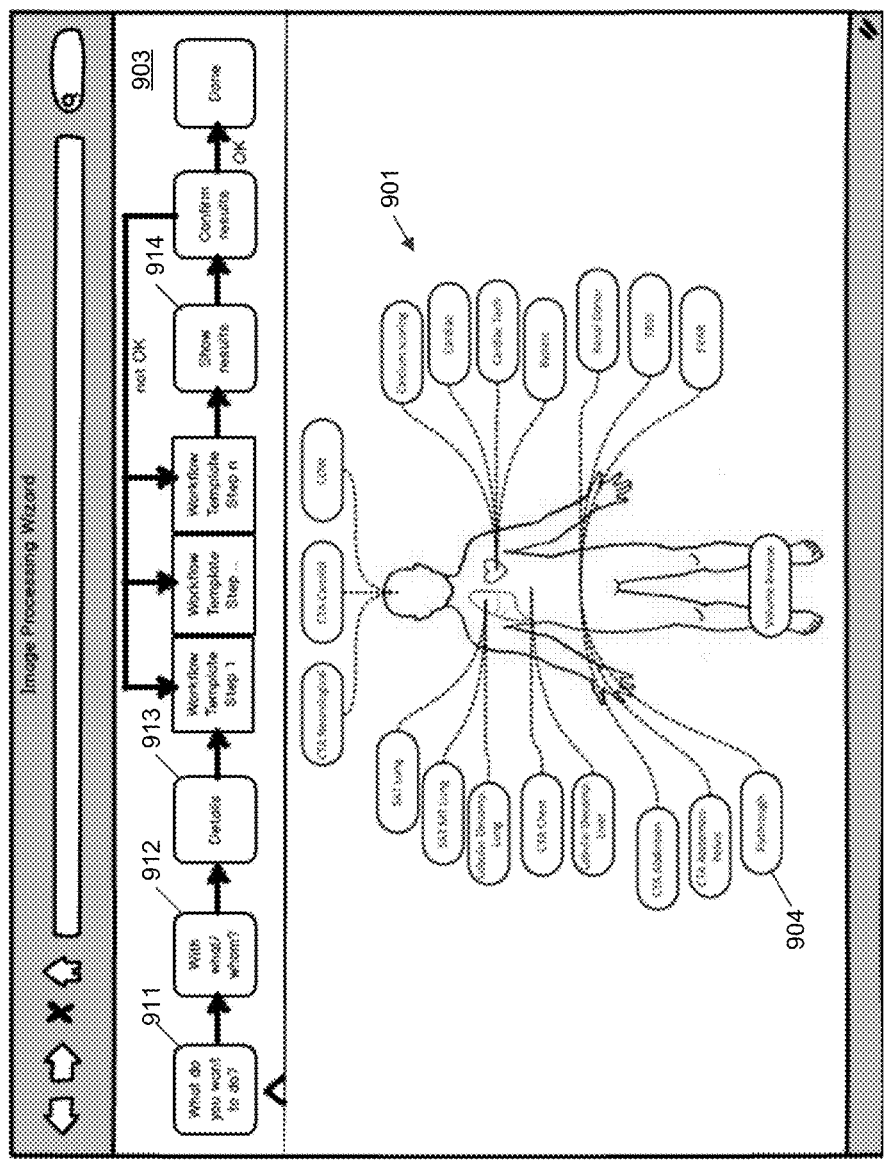
FIGS. 9A-9F are screenshots illustrating examples of graphical user interface of an automatic image processing system according certain embodiments of the invention.

FIGS. 9A-9F are screenshots illustrating examples of graphical user interface of an automatic image processing system according alternative embodiments of the invention. The GUIs as shown in FIGS. 9A-9F may be generated by image processing server 110 and received and represented at a client device. User interactions with the GUIs are captured and transmitted from the client device to image processing server 110. The user interactions are then interpreted by image processing server 110 and in response to the user interaction, image processing server 110 performs proper actions, such as, image processing operations, information retrieval operations, and data processing and/or integration operations, and returns processing results back to the client. The processing results are presented and/or integrated with the existing information at a display device of the client. FIG. 9A, shows another example of how a user may use the client 105. The method of accessing image data shown in this embodiment is by body area. A graphical representation of a human body is shown and image tags, such as SAT lung and Flythrough, are shown associated with the different body areas 901. These image tags 901 are selectable or clickable and will bring the user to another screen, which may provide a patient list relating to particular body part/procedure selected. From the patient list, the user can retrieve one or more images that are associated with a particular patient in the list, where the images are also related to the corresponding body area of the selected image tag.

Across the top of this screen is a timeline, or process line, or workflow, of the image data viewing/processing process 903, similar to timeline 703 of FIG. 7A. The user is currently at the "what do you want to do?" stage 911. At this stage, the user can choose the type of image data he/she wants to view/process, for example, by selecting one or more of the image tags displayed in display area 902. The timeline 903 shows that subsequent steps will include choosing a patient, choosing more details (e.g., detail stage 913) relating to the images/patient, processing the images, showing the results, determining whether the results are acceptable or unacceptable, and finishing the process.

Figure 9B:
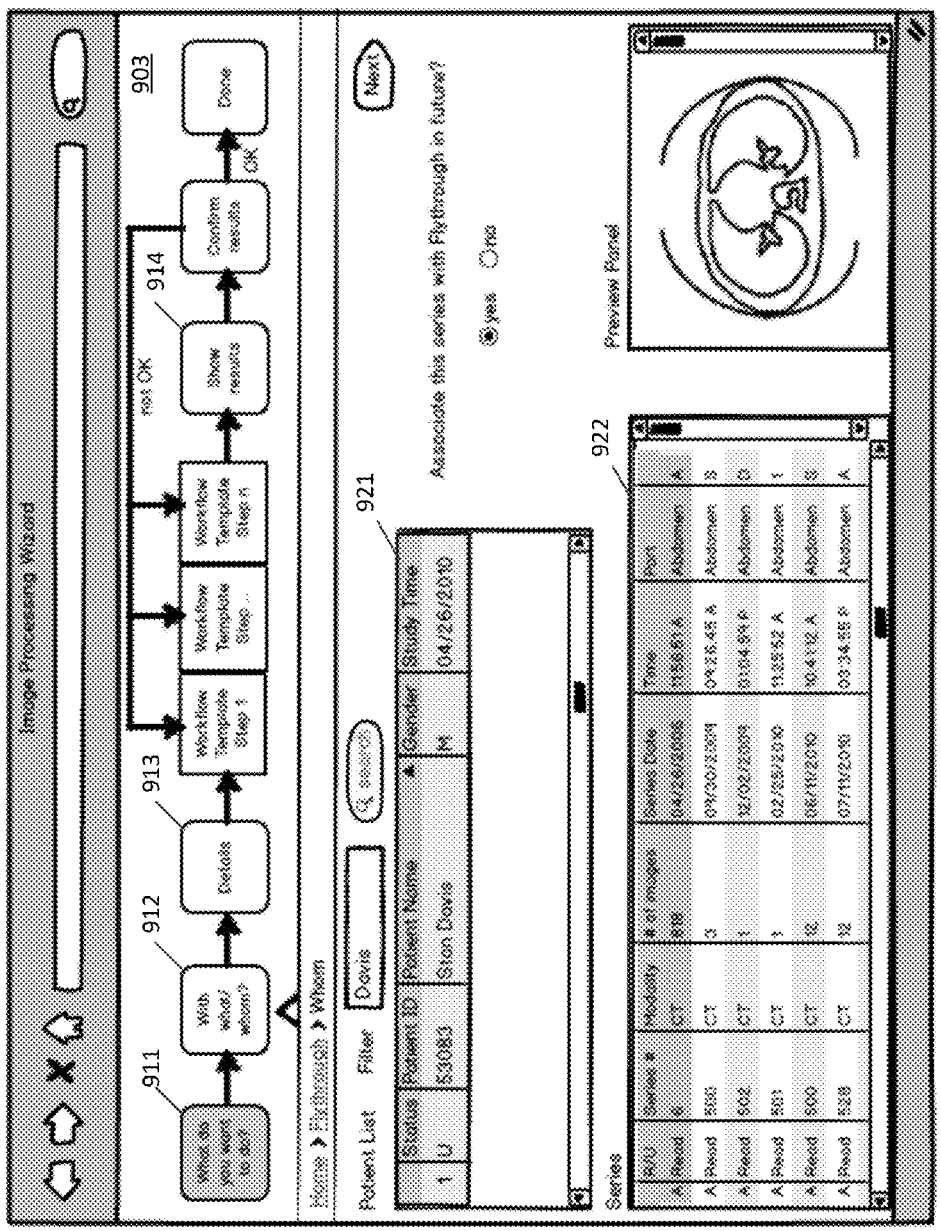

FIG. 9B shows a screen representing the "with what/whom" stage 912 in the timeline 903. For example, if the "flythrough" tag 904 of FIG. 9A is selected, an identifier identifying a flythrough procedure is transmitted from the client to the image processing server 110. In response, the image processing server 110 identifies or generates based on the identifier a list of patients who have an image associated with the flythrough procedure. The result is returned from the image processing server to the client device and the user can see a list of patients 921 who have images on records associated with a flythrough procedure. Also shown are different series of images 922 associated with a given patient, as well as a preview panel 923 showing the images associated with each series, which are also generated by the image processing server 110 and received at the client device. The user can search through the patients/series to find the patient/series he/she wants. Note that the information as shown in FIG. 9B may be retrieved by the underlying logic (e.g., components or logic 401-402 of FIG. 4) from image processing server 110 and/or medical data server 115 of FIG. 1 in response to the user inputs, without requiring the user to know the details. The relationships between patients and images of a particular body area may be stored in a database maintained by image processing server 110 and/or MRCS server 115 of FIG. 1. The user also has the option of associating certain series of images with a procedure in the future.

Figure 9C:
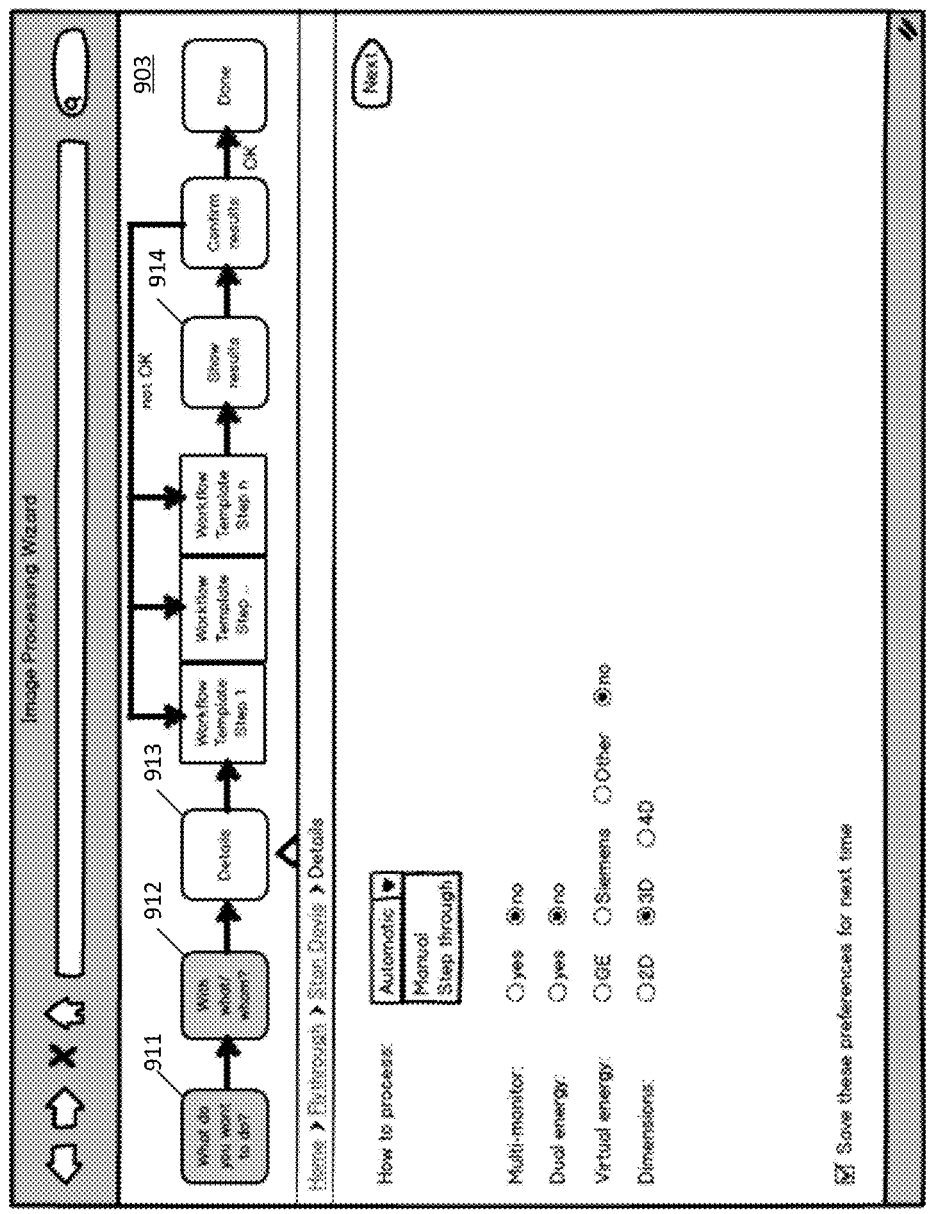

FIG. 9C shows a screen representing the "details" stage 913 in the timeline, which may be displayed in response to an activation of the "next" button from FIG. 9B. Here the user can set preferences including how to process the image(s), etc. The user can also set the preferences as defaults so that this step may be skipped in the future. The user preferences may be stored as part of user preferences 404 of FIG. 4 and transmitted back to image processing server 110 to be stored therein, for example, as part of a user account or user profile associated with the user in a persistent storage device such as a hard disk. As a result, when the user subsequently logs into the image processing server 110, for example, from the same or a different client device, the user can retrieve the user preferences from the image processing server.

Figure 9D:
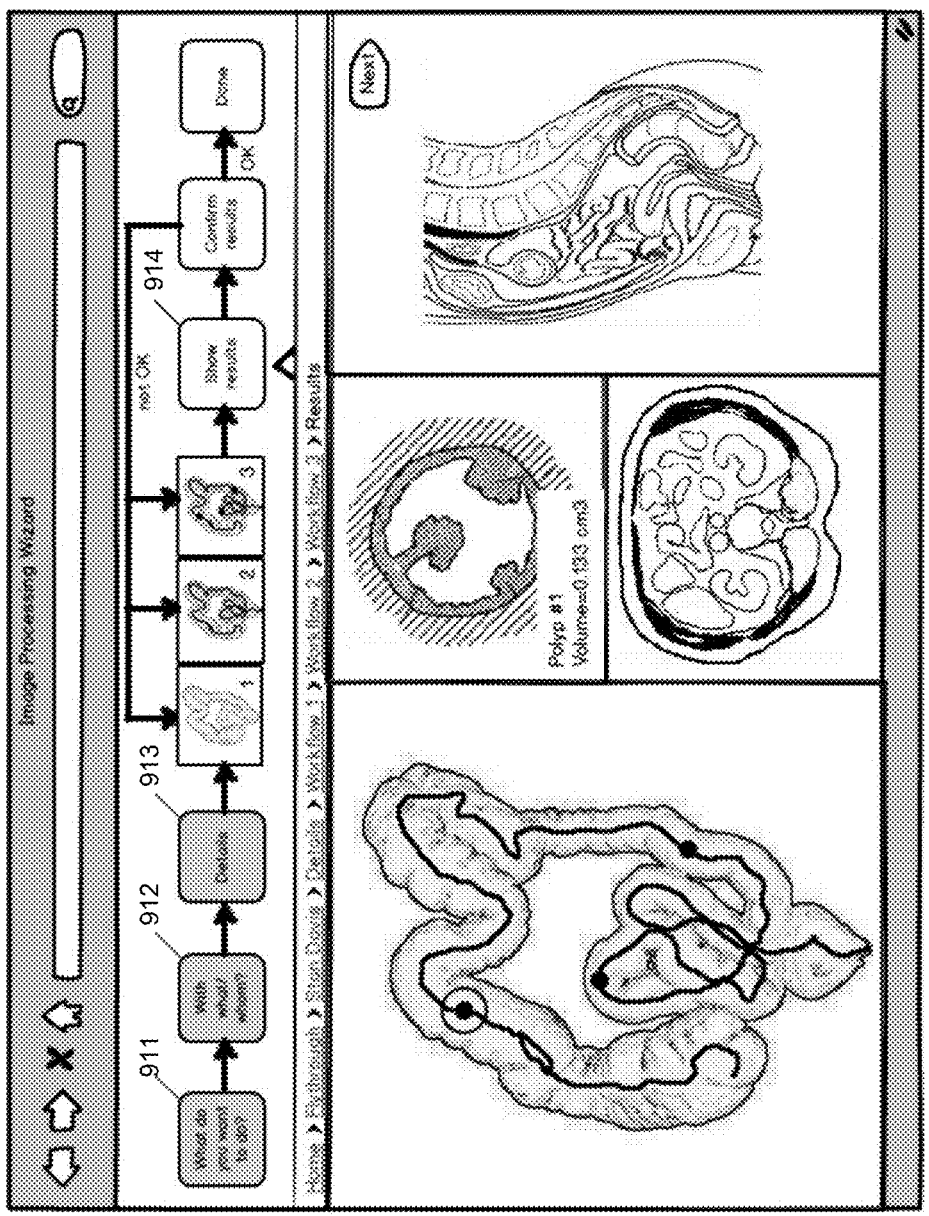

FIG. 9D shows an example of show result stage 914. In this example, the results for the flythrough show 3 identified polyps, along with several different views of the intestines and polyps, and quantitative data for the polyps, such as volume. In this example, the image processing results were performed automatically, without user intervention, by the image data processor (e.g., image processing server and/or client). If the user selects or highlights one of the polyps, he/she can see the location in the anatomy where the polyp was found from different perspectives, as well as quantitative data. In this way, the results can be fully analyzed and reviewed. Notice that the timeline 903 on the top of the screen shows where in the process the user is. Since this is the results screen 914, the timeline 903 shows that the processing has already taken place and the user is now viewing the results of the image processing. When the user is finished reviewing the results, he may click on the "next" button to go to the next step, confirm result stage.

Figure 9E:
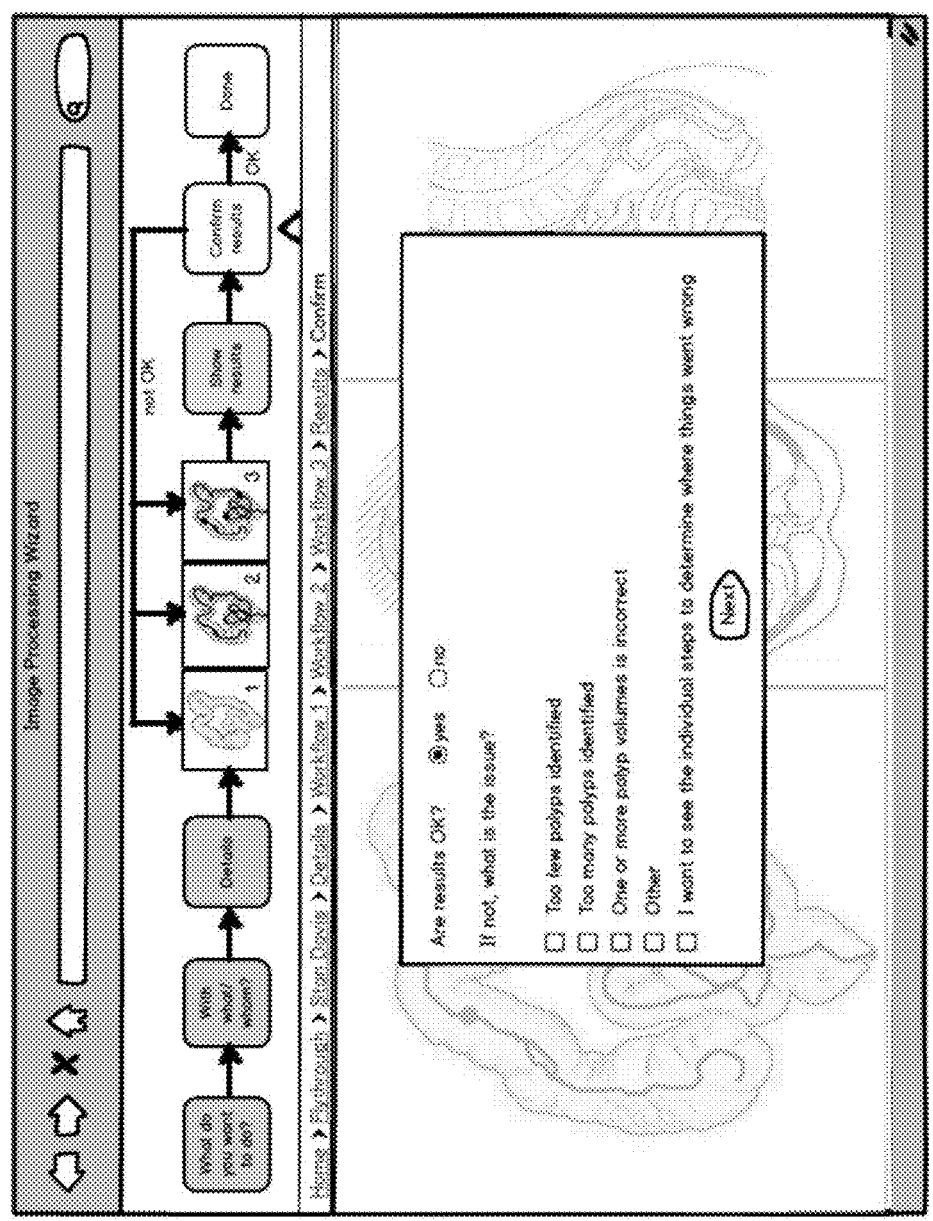
Figure 9F:
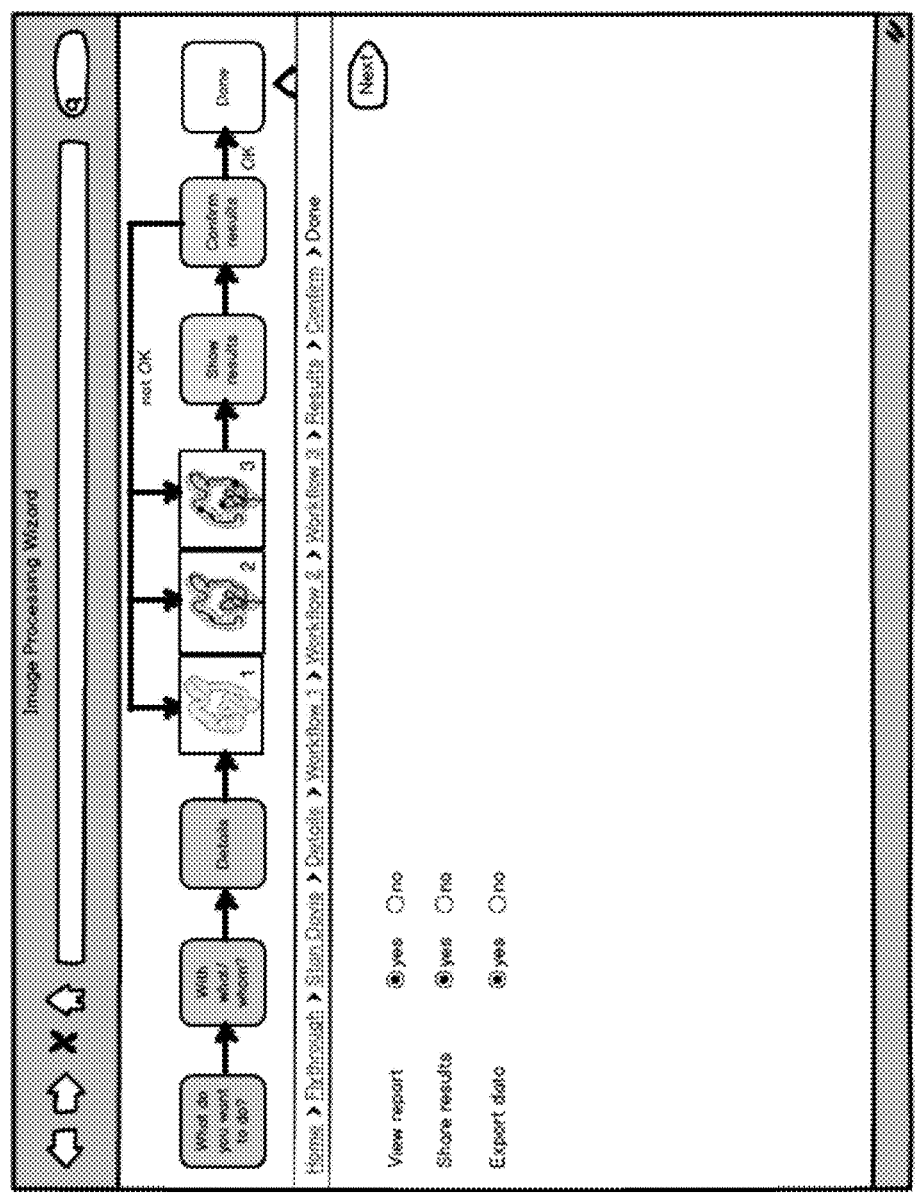

FIG. 9E shows an example of a wizard pop-up window which helps the user either confirm the image data processing results, or improve the results. In this example, the user has indicated that the image processing results are satisfied. FIG. 9F shows some example options available to the user after the image processing results have been confirmed. Options include report generation, sharing the results with other physicians, patients or others, and exporting the data in various formats including xml, csv, html and other formats. Other options may be available.

Note that the user interactions with the GUIs as shown in FIGS. 8A-8K and FIGS. 9A-9F may be captured, interpreted and analyzed by the underlying logic such as those as shown in FIG. 4. Based on the analysis, one or more commands are generated by the underlying logic and communicated with the image processing server 110 and/or MRCS server 115. A user does not have to fully understanding the underlying operations, parameters, and image processing commands. However, an advanced user can also invoke advanced image processing system 140 as needed. Automatic image processing system 150 provides an alternative way to access image processing tools based on user preferences and/or privileges.

Although GUIs for the user are generally shown here as clickable objects on a computer screen, other types of input devices may be used to interact with the GUI. For example, The user may use voice and/or motion and/or gestures to interact with the GUI. These types of input devices are particularly useful in a sterile environment such as an operating room.

FIG. 10 is a flow diagram illustrating a process performed by an automatic image processing system according to one embodiment of the invention. Process 1000 may be performed by processing logic which may include software, hardware, or a combination thereof. For example, process 1000 may be performed by automatic image processing system 150 of FIG. 1. Referring to FIG. 10, at block 1001, an image processing indicator is received at an automatic image processing system from a client device. The image processing indicator identifies at least one of a patient, a body area of a patient, a medical procedure, a medical appointment, a timeframe, and a user of the client device. At block 1002, processing logic automatically identifies a first image based on the image processing indicator, for example, based on a set of rules (e.g., rules as shown in FIG. 5). The processing logic determines one or more image operations, the associated processing parameters, and/or dimension, etc. An image processing engine is invoked to process the first image by performing the determined image processing operations based on the associated processing parameters. At block 1003, processing logic transmits a second image resulted from the image processing operations to the client device to be presented on a display of the client device. At block 1004, a request is transmitted to the client device to cause the client device to prompt the user whether the user is satisfied with the second image, optionally with one or more options for further user inputs. At block 1005, in response to a user input received from the client device indicating that the user is not satisfied with the second image, processing logic determines and transmits to the client device one or more remedial options to allow the user to select a remedial action to reprocess the first image.

As described above, a variety of image processing tools can be accessed by a user using the automatic image processing system, for example, as an image processing wizard. The following are examples of medical image processing tools that may be included as part of the image processing system described above. These examples are provided for illustrative purposes and not intended to be a limitation of the present invention.

Vessel Analysis tools may include a comprehensive vascular analysis package for CT and MR angiography capable of a broad range of vascular analysis tasks, from coronary arteries to aortic endograft planning and more general vascular review, including carotid and renal arteries. Auto-centerline extraction, straightened view, diameter and length measurements, CPR and axial renderings, and Vessel Track mode for automated thin-slab MIP may be included.

Calcium scoring tools may include Semi-automated identification of coronary calcium with Agatston, volume and mineral mass algorithms. An integrated reporting package with customization options may be included.

Time-dependent analysis tools may include time-resolved planar or volumetric 4D brain perfusion examinations acquired with CT or MR. The TDA tools may support color or mapping of various parameters such as mean enhancement time and enhancement integral, with semi-automated selection of input function and baseline, to speed analysis. TDA tools may support rapid automated processing of dynamic 4D area-detector CT examinations to ensure interpretation within minutes of acquisition.

CT/CTA (Computed tomography angiography) subtraction tools are used in the removal of non-enhancing structures (e.g. bone) from CT angiography examinations, the CT/CTA option includes automatic registration of pre- and post-contrast images, followed by a dense-voxel masking algorithm which removes high-intensity structures (like bone and surgical clips) from the CTA scan without increasing noise, aiding with the isolation of contrast-enhanced vascular structures.

Lobular decomposition tools identify tree-like structures within a volume of interest, e.g. a scan region containing a vascular bed, or an organ such as the liver. The LD tool can then identifies sub-volumes of interest based on proximity to a given branch of the tree or one of its sub-branches. Research applications include the analysis of the lobular structure of organs.

General Enhancement & Noise Treatment with Low Exposure tools may include an advanced volumetric filter architecture applying noise management techniques to improve the effectiveness of 3D, centerline, contouring and segmentation algorithms even when source image quality is not optimum.

The Spherefinder tools perform automated analysis of volumetric examinations to identify the location of structures with a high sphericity index (characteristics exhibited by many nodules and polyps). Spherefinder is often used with Lung or Colon CT scans to identify potential areas of interest.

Segmentation, analysis & tracking tools support analysis and characterization of masses and structures, such as solitary pulmonary nodules or other potential lesions. Tools may identify and segment regions of interest, and then apply measurement criteria, such as RECIST and WHO, leading to tabulated reporting of findings and follow-up comparison. Display and management of candidate markers from optional detection engines may be supported, including Spherefinder.

Time volume analysis tools may provide automated calculation of ejection fraction from a chamber in rhythmic motion, such as a cardiac ventricle. A fast and efficient workflow may be included to enable the user to identify the wall boundaries of interest (e.g. epicardium and endocardium) and, based on these user-confirmed regions of interest, to report ejection fraction, wall volume (mass) and wall thickening from multi-phasic CT data. Tabulated reporting output is included.

Maxillo-facial tools support the analysis and visualization of CT examinations of the Maxillo-facial region, these tools apply the CPR tool to generate "panoramic" projections in various planes and of various thicknesses, and cross-sectional MPR views at set increments along the defined curve plane.

Applicable to endoluminal CT or MR investigations such as colon, lungs, or blood vessels, the Flythrough tools supports side-by-side review, painting of previously-viewed areas, percent coverage tracking, and multiple screen layouts including forward, reverse, fisheye and flat volume rendered views. Tools for contrast subtraction, "Cube View", and integrated contextual reporting may be supported. Display and management of candidate markers from optional detection engines may be supported, including iNtuition's Spherefinder.

The Volumetric Histogram tools allow a volume of interest to be segmented and analyzed for composition. Research applications include the analysis of low-attenuation regions of the lungs, threshold-based division of tumors into voxel populations, investigation of thrombosed vessels or aneurysms, or other pathology.

Findings workflow tools provide a framework for tracking findings across serial examinations. A database holds measurements and key images, and provides support for structured comparisons and tabulated reporting of findings over time, such as the RECIST 1.1 approach for presenting serial comparisons. The Annotation and Image Markup (AIM) XML schema may be supported, for automated integration with voice-recognition systems or clinical databases, and Word-based reports may be derived from the database.

With these tools, any two CT, PET, MR or SPECT series, or any two-series combination thereof can be overlaid with one assigned a semi-transparent color coding and the other shown in grayscale and volume rendering for anatomical reference. Automatic registration is provided and subtraction to a temporary series or to a saved, third series is possible. Support for PET/MR visualization is included.

Certain MR examinations (for example, Breast MR) involve a series of image acquisitions taken over a period of time, where certain structures become enhanced over time relative to other structures. These tools feature the ability to subtract a pre-enhancement image from all post-enhancement images to emphasize visualization of enhancing structures (for example, vascular structures and other enhancing tissue). Time-dependent region-of-interest tools may be provided to plot time-intensity graphs of a given region.

Parametric mapping tools are an enhancement to the Multi-Phase MR tools, the parametric mapping option pre-calculates overlay maps where each pixel in an image is color-coded depending on the time-dependent behavior of the pixel intensity. As an example, this tool can be used in Breast MR to speed identification and investigation of enhancing regions.

The MultiKv tools provide support for Dual Energy and Spectral Imaging acquisitions from multiple vendors, providing standard image processing algorithms such as segmentation or contrast suppression, as well as generic toolkits for precise analysis and development of new techniques.

The embodiments described above can be applied to a variety of medical areas. For example, the techniques described above can be applied to vessel analysis (including Endovascular Aortic Repair (EVAR) and electrophysiology (EP) planning). Such vessel analysis is performed for interpretation of both coronary and general vessel analysis such as carotid and renal arteries, in addition to aortic endograft and electro-physiology planning. Tools provided as cloud services include auto-centerline extraction, straightened view, diameter and length measurements, Curved Planar Reformation (CPR) and axial renderings, as well as charting of the vessel diameter vs. distance and cross-sectional views. The vessel track tool provides a Maximum Intensity Projection (MIP) view in two orthogonal planes that travels along and rotates about the vessel centerline for ease of navigation and deep interrogation. Plaque analysis tools provide detailed delineation of non luminal structure such as soft plaque, calcified plaque and intra-mural lesions.

In addition, the techniques described above can be utilized in the area of endovascular aortic repair. According to some embodiments, vascular analysis tools provided as cloud services support definition of report templates which captures measurements for endograft sizing. Multiple centerlines can be extracted to allow for planning of EVAR procedures with multiple access points. Diameters perpendicular to the vessel may be measured along with distances along the two aorto-iliac paths. Custom workflow templates may be used to enable the major aortic endograft manufactures' measurement specifications to be made as required for stent sizing. Sac segmentation and volume determination with a "clock-face" overlay to aid with documenting the orientation and location of branch vessels for fenestrated and branch device planning, may also be used. Reports containing required measurements and data may be generated.

The techniques described above can also be applied in the left atrium analysis mode, in which semi-automated left atrium segmentation of each pulmonary vein ostium is supported with a single-click distance pair tool, provided as cloud services, for assessment of the major and minor vein diameter. Measurements are automatically detected and captured into the integrated reporting system. These capabilities can be combined with other vessel analysis tools to provide a comprehensive and customized EP planning workflow for ablation and lead approach planning.

The techniques described above can also be utilized in calcium scoring. Semi-automated identification of coronary calcium is supported with Agatston, volume and mineral mass algorithms being totaled and reported on-screen. Results may be stored in an open-format database along with various other data relating to the patient and their cardiovascular history and risk factors. A customized report can be automatically generated, as part of cloud services, based upon these data. Also includes report generation as defined by the Society of Cardiovascular Computed Tomography (SCCT) guidelines.

The techniques described above can also be utilized in a time-volume analysis (TVA), which may include fully-automated calculation of left ventricular volume, ejection fraction, myocardial volume (mass) and wall thickening from multi-phasic data. A fast and efficient workflow provided as part of cloud services allows for easy verification or adjustment of levels and contours. The results are presented within the integrated reporting function.

The techniques described above can also be utilized in the area of segmentation analysis and tracking (SAT), which includes supports analysis and characterization of masses and structures in various scans, including pulmonary CT examinations. Features include single-click segmentation of masses, manual editing tools to resolve segmentation issues, automatic reporting of dimensions and volume, graphical 3D display of selected regions, integrated automated reporting tool, support for follow-up comparisons including percent volume change and doubling time, and support for review of sphericity filter results.

The techniques described above can also be utilized in the area of flythrough which may include features of automatic segmentation and centerline extraction of the colon, with editing tools available to redefine these centerlines if necessary. 2D review includes side-by-side synchronized supine and prone data sets in either axial, coronal or sagittal views with representative synchronized endoluminal views. 3D review includes axial, coronal and sagittal MPR or MIP image display with large endoluminal view and an unfolded view that displays the entire colon. Coverage tracking is supported to ensure 100% coverage with stepwise review of unviewed sections, one-click polyp identification, bookmark and merge findings, as well as a cube view for isolating a volume of interest and an integrated contextual reporting tool. Support is provided for use of sphericity filter results.

The techniques described above can also be utilized in the area of time-dependent analysis (TDA), which provides assessment tools for analyzing the time-dependent behavior of appropriate computerized tomographic angiography (CTA) and/or MRI examinations, such as within cerebral perfusion studies. Features include support for loading multiple time-dependent series at the same time, and a procedural workflow for selecting input and output function and regions of interest. An integrated reporting tool is provided as well as the ability to export the blood flow, blood volume and transit time maps to DICOM. The tools may also be used with time-dependent MR acquisitions to calculate various time-dependent parameters.

The techniques described above can also be utilized in the area of CTA-CT subtraction, which includes automatic registration of pre- and post-contrast images, followed by subtraction or dense-voxel masking technique which removes high-intensity structures (like bone and surgical clips) from the CTA scan without increasing noise, and leaving contrast-enhanced vascular structures intact.

The techniques described above can also be utilized in dental analysis, which provides a CPR tool which can be applied for review of dental CT scans, offering the ability to generate "panoramic" projections in various planes and of various thicknesses, and cross-sectional MPR views at set increments along the defined curve plane.

The techniques described above can also be utilized in the area of multi-phase MR (basic, e.g. breast, prostate MR). Certain MR examinations (for example, breast, prostate MR) involve a series of image acquisitions taken over a period of time, where certain structures become enhanced over time relative to other structures. This module features the ability to subtract a pre-enhancement image from all post-enhancement images to emphasize visualization of enhancing structures (for example, vascular structures and other enhancing tissue). Time-dependent region-of-interest tools are provided to plot time-intensity graphs of a given region.

The techniques described above can also be utilized in parametric mapping (e.g. for multi-phase Breast MR), in which the parametric mapping module pre-calculates overlay maps where each pixel in an image is color-coded depending on the time-dependent behavior of the pixel intensity. The techniques described above can also be utilized in the area of SphereFinder (e.g. sphericity filter for lung and colon). SphereFinder pre-processes datasets as soon as they are received and applies filters to detect sphere-like structures. This is often used with lung or colon CT scans to identify potential areas of interest. The techniques described can also be utilized in fusion for CT/MR/PET/SPECT. Any two CT, PET, MR or SPECT series, or any two-series combination can be overlaid with one assigned a semi-transparent color coding and the other shown in grayscale and volume rendering for anatomical reference. Automatic registration is provided and subtraction to a temporary series or to a saved, third series is possible.

The techniques described above can also be utilized in the area of Lobular Decomposition. Lobular Decomposition is an analysis and segmentation tool that is designed with anatomical structures in mind. For any structure or organ region which is intertwined with a tree-like structure (such as an arterial and/or venous tree), the Lobular Decomposition tool allows the user to select the volume of interest, as well as the trees related to it, and to partition the volume into lobes or territories which are most proximal to the tree or any specific sub-branch thereof. This generic and flexible tool has potential research applications in analysis of the liver, lung, heart and various other organs and pathological structures.

The techniques described above can also be utilized in the area of Volumetric Histogram. Volumetric Histogram supports analysis of a given volume of interest based on partition of the constituent voxels into populations of different intensity or density ranges. This can be used, for example, to support research into disease processes such as cancer (where it is desirable to analyze the composition of tumors, in an attempt to understand the balance between active tumor, necrotic tissue, and edema), or emphysema (where the population of low-attenuation voxels in a lung CT examination may be a meaningful indicator of early disease).

The techniques described above can also be utilized in the area of Motion Analytics. Motion Analytics provides a powerful 2D representation of a 4D process, for more effective communication of findings when interactive 3D or 4D display is not available. Any dynamic volume acquisition, such as a beating heart, can be subjected to the Motion Analysis, to generate a color-coded "trail" of outlines of key boundaries, throughout the dynamic sequence, allowing a single 2D frame to capture and illustrate the motion, in a manner that can be readily reported in literature. The uniformity of the color pattern, or lack thereof, reflects the extent to which motion is harmonic, providing immediate visual feedback from a single image.

Figure 11A:
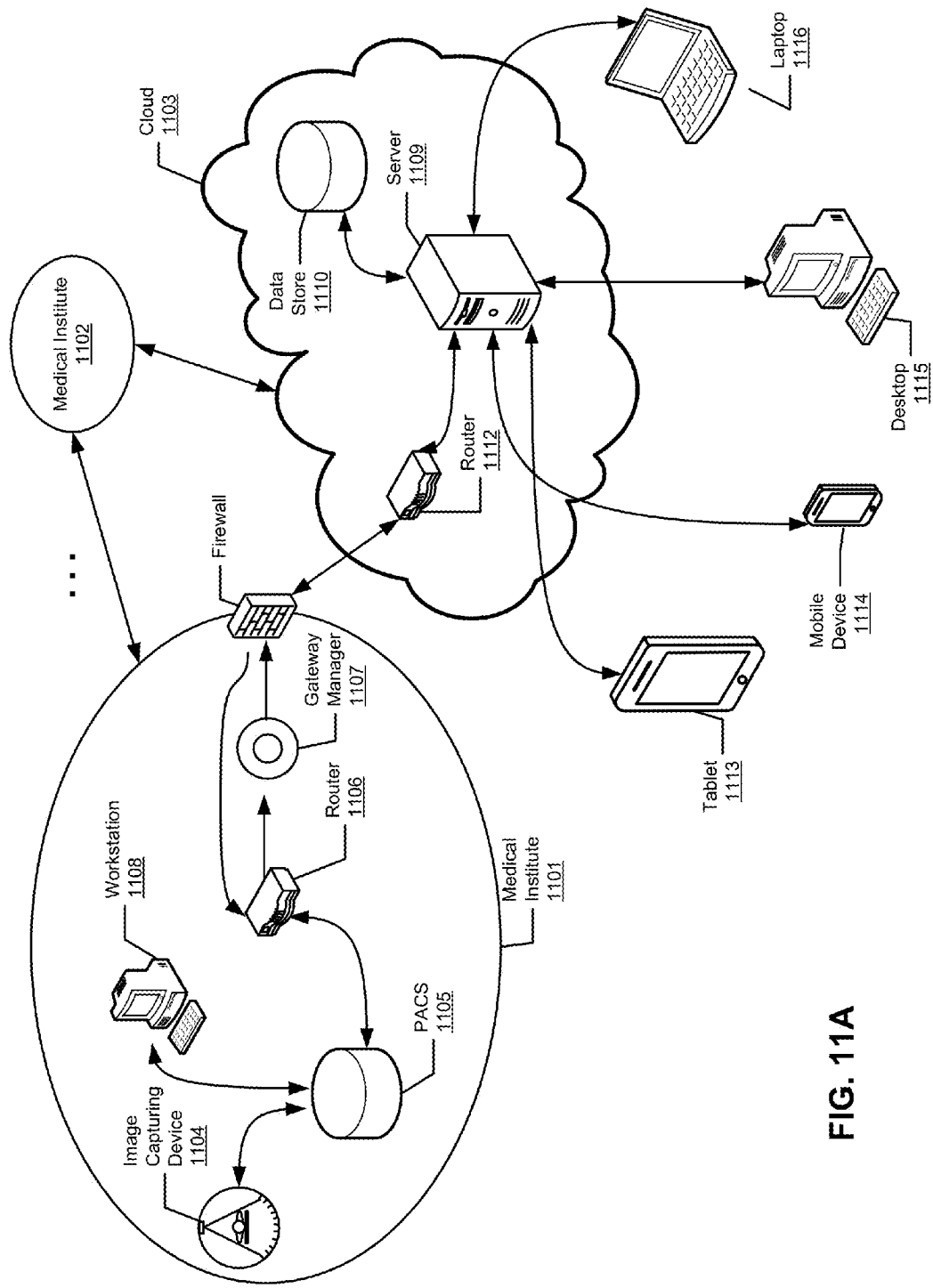
FIGS. 11A and 11B are block diagrams illustrating a cloud-based image processing system according to certain embodiments of the invention.
Figure 11B:
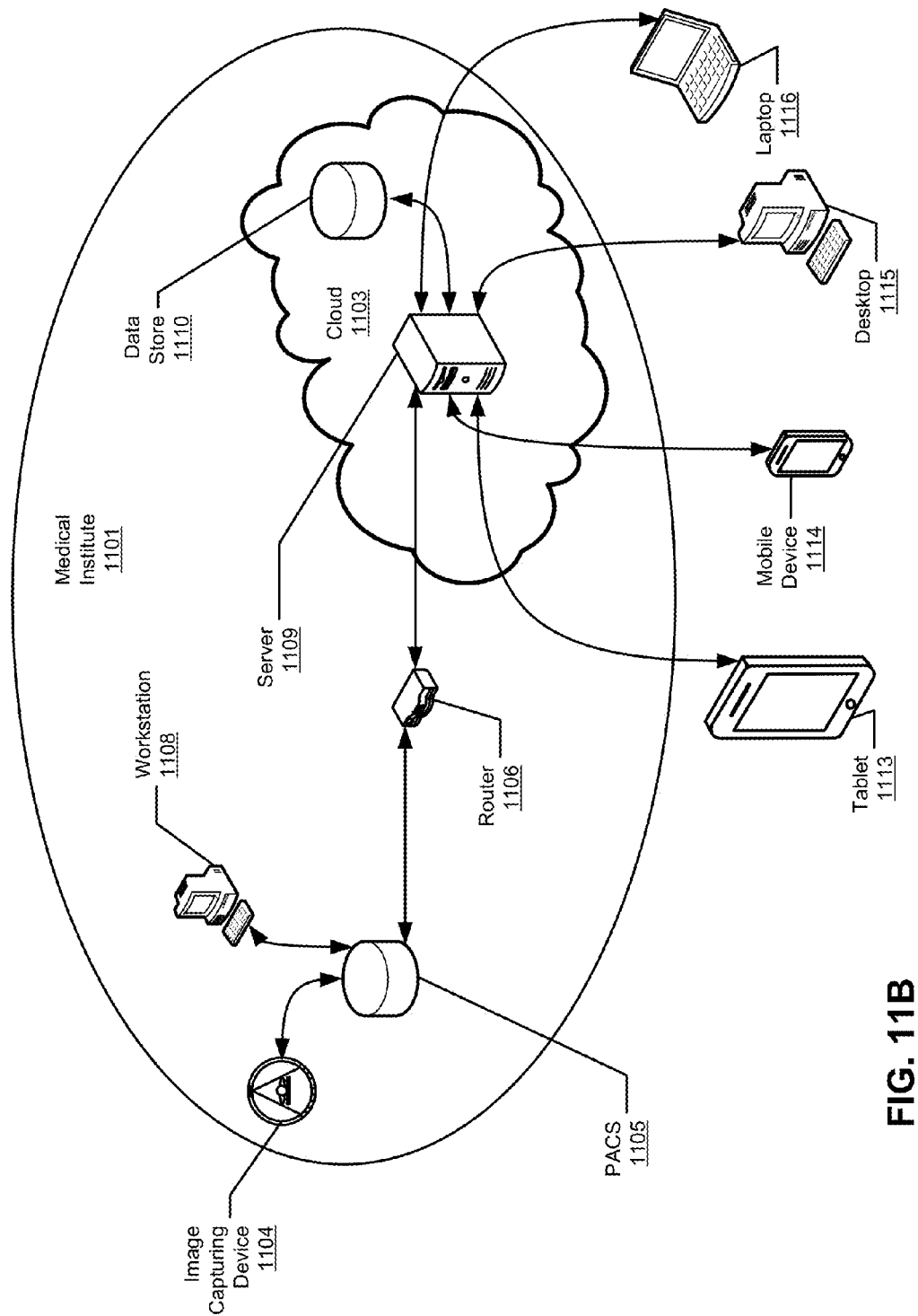

FIGS. 11A and 11B are block diagrams illustrating a cloud-based image processing system according to certain embodiments of the invention. Referring to FIG. 11A, according to one embodiment, system 1100 includes one or more entities or institutes 1101-1102 communicatively coupled to cloud 1103 over a network. Entities 1101-1102 may represent a variety of organizations such as medical institutes having a variety of facilities residing all over the world. For example, entity 1101 may include or be associated with image capturing device or devices 1104, image storage system (e.g., PACS) 1105, router 1106, and/or data gateway manager 1107. Image storage system 1105 may be maintained by a third party entity that provides archiving services to entity 1101, which may be accessed by workstation 1108 such as an administrator or user associated with entity 1101. Note that throughout this application, a medical institute is utilized as an example of an organization entity. However, it is not so limited; other organizations or entities may also be applied.

In one embodiment, cloud 1103 may represent a set of servers or clusters of servers associated with a service provider and geographically distributed over a network. For example, cloud 1103 may be associated with a medical image processing service provider such as TeraRecon of Foster City, Calif. A network may be a local area network (LAN), a metropolitan area network (MAN), a wide area network (WAN) such as the Internet or an intranet, or a combination thereof. Cloud 1103 can be made of a variety of servers and devices capable of providing application services to a variety of clients such as clients 1113-1116 over a network. In one embodiment, cloud 1103 includes one or more cloud servers 1109 to provide image processing services, one or more databases 1110 to store images and other medical data, and one or more routers 1112 to transfer data to/from other entities such as entities 1101-1102. If the cloud server consists of a server cluster, or more than one server, rules may exist which control the transfer of data between the servers in the cluster. For example, there may be reasons why data on a server in one country should not be placed on a server in another country.

Server 1109 may be an image processing server to provide medical image processing services to clients 1113-1116 over a network. For example, server 1109 may be implemented as part of a TeraRecon AquariusNET™ server and/or a Tera-Recon AquariusAPS server. Data gateway manager 1107 and/or router 1106 may be implemented as part of a TeraRecon AquariusGATE device. Medical imaging device 1104 may be an image diagnosis device, such as X-ray CT device, MRI scanning device, nuclear medicine device, ultrasound device, or any other medical imaging device. Medical imaging device 1104 collects information from multiple cross-section views of a specimen, reconstructs them, and produces medical image data for the multiple cross-section views. Medical imaging device 1104 is also referred to as a modality.

Database 1110 may be a data store to store medical data such as digital imaging and communications in medicine (DICOM) compatible data or other image data. Database 1110 may also incorporate encryption capabilities. Database 1110 may include multiple databases and/or may be maintained by a third party vendor such as storage providers. Data store 1110 may be implemented with relational database management systems (RDBMS), e.g., Oracle™ database or Microsoft® SQL Server, etc. Clients 1113-1116 may represent a variety of client devices such as a desktop, laptop, tablet, mobile phone, personal digital assistant (PDA), etc. Some of clients 1113-1116 may include a client application (e.g., thin client application) to access resources such as medical image processing tools or applications hosted by server 1109 over a network. Examples of thin clients include a web browser, a phone application and others.

According to one embodiment, server 1109 is configured to provide advanced image processing services to clients 1113-1116, which may represent physicians from medical institutes, instructors, students, agents from insurance companies, patients, medical researchers, etc. Cloud server 1109, also referred to as an image processing server, has the capability of hosting one or more medical images and data associated with the medical images to allow multiple participants such as clients 1113-1116, to participate in a discussion/processing forum of the images in a collaborated manner or conferencing environment. Different participants may participate in different stages and/or levels of a discussion session or a workflow process of the images.

According to some embodiments, data gateway manager 1107 is configured to automatically or manually transfer medical data to/from data providers (e.g., PACS systems) such as medical institutes. Such data gateway management may be performed based on a set of rules or policies, which may be configured by an administrator or authorized personnel. In one embodiment, in response to updates of medical images data during an image discussion session or image processing operations performed in the cloud, the data gateway manager is configured to transmit over a network (e.g., Internet) the updated image data or the difference between the updated image data and the original image data to a data provider such as PACS 1105 that provided the original medical image data. Similarly, data gateway manager 1107 can be configured to transmit any new images and/or image data from the data provider, where the new images may have been captured by an image capturing device such as image capturing device 1104 associated with entity 1101. In addition, data gateway manager 1107 may further transfer data amongst multiple data providers that is associated with the same entity (e.g., multiple facilities of a medical institute). Furthermore, cloud 1103 may include an advanced preprocessing system (not shown) to automatically perform certain pre-processing operations of the received images using certain advanced image processing resources provided by the cloud systems. In one embodiment, gateway manager 1107 is configured to communicate with cloud 1103 via certain Internet ports such as port 80 or 443, etc. The data being transferred may be encrypted and/or compressed using a variety of encryption and compression methods. The term "Internet port" in this context could also be an intranet port, or a private port such as port 80 or 443 etc. on an intranet.

Figure 12:
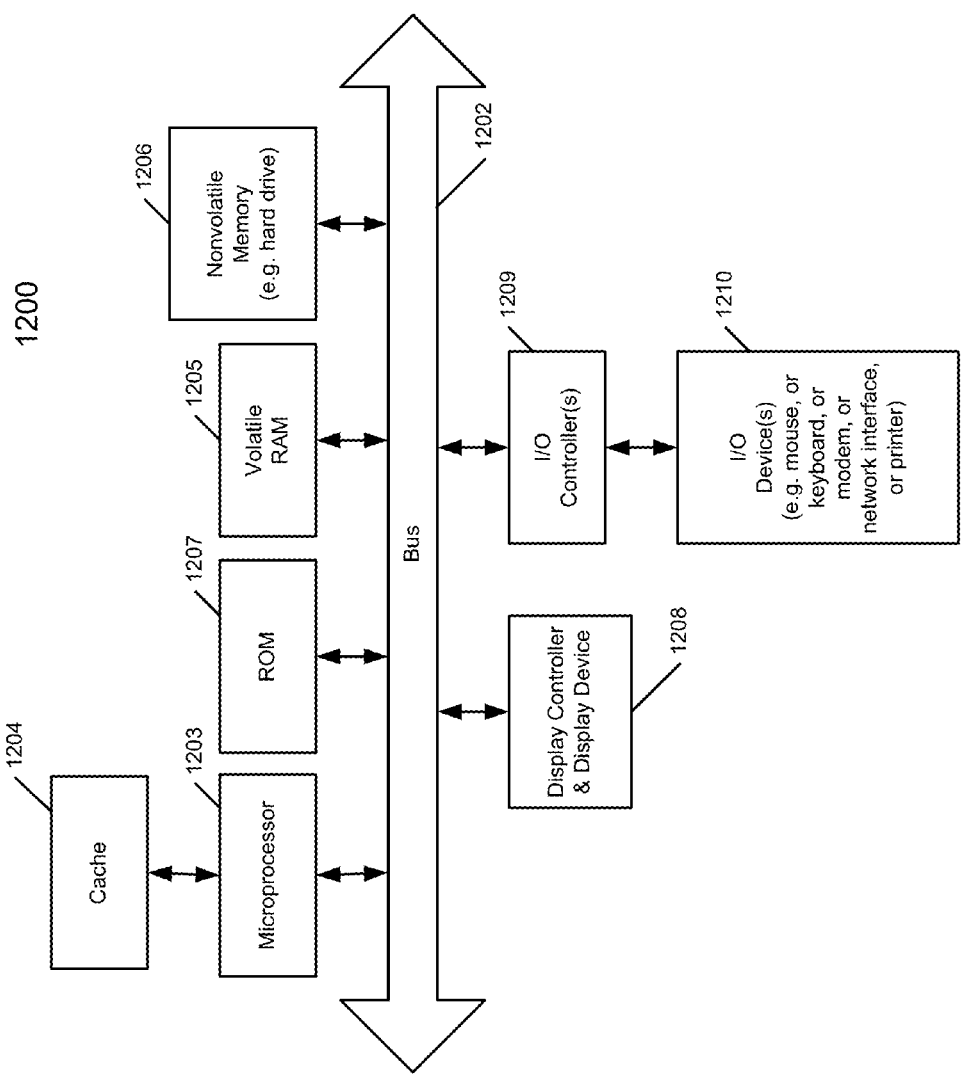
FIG. 12 is a block diagram of a data processing system, which may be used with one embodiment of the invention.

FIG. 12 is a block diagram of a data processing system, which may be used with one embodiment of the invention. For example, the system 1200 may be used as part of a server or a client as described above. For example, system 1200 may represent image processing server 110, which is communicatively coupled to a remote client device or another server via network interface 1210. Advanced image processing system 140, automatic image processing system 150, and image processing engine 104, as described above, may be hosted by system 1200. In one embodiment, advanced image processing system 140 and/or automatic image processing system 150 may be loaded in memory 1205 and executed by processor 1203 to perform various operations or processes as described above.

Note that while FIG. 12 illustrates various components of a computer system, it is not intended to represent any particular architecture or manner of interconnecting the components; as such details are not germane to the present invention. It will also be appreciated that network computers, handheld computers, cell phones and other data processing systems which have fewer components or perhaps more components may also be used with the present invention.

As shown in FIG. 12, the computer system 1200, which is a form of a data processing system, includes a bus or interconnect 1202 which is coupled to one or more microprocessors 1203 and a ROM 1207, a volatile RAM 1205, and a non-volatile memory 1206. The microprocessor 1203 is coupled to cache memory 1204. The bus 1202 interconnects these various components together and also interconnects these components 1203, 1207, 1205, and 1206 to a display controller and display device 1208, as well as to input/output (I/O) devices 1210, which may be mice, keyboards, modems, network interfaces, printers, and other devices which are well-known in the art.

Typically, the input/output devices 1210 are coupled to the system through input/output controllers 1209. The volatile RAM 1205 is typically implemented as dynamic RAM (DRAM) which requires power continuously in order to refresh or maintain the data in the memory. The non-volatile memory 1206 is typically a magnetic hard drive, a magnetic optical drive, an optical drive, or a DVD RAM or other type of memory system which maintains data even after power is removed from the system. Typically, the non-volatile memory will also be a random access memory, although this is not required.

While FIG. 12 shows that the non-volatile memory is a local device coupled directly to the rest of the components in the data processing system, the present invention may utilize a non-volatile memory which is remote from the system; such as, a network storage device which is coupled to the data processing system through a network interface such as a modem or Ethernet interface. The bus 1202 may include one or more buses connected to each other through various bridges, controllers, and/or adapters, as is well-known in the art. In one embodiment, the I/O controller 1209 includes a USB (Universal Serial Bus) adapter for controlling USB peripherals. Alternatively, I/O controller 1209 may include an IEEE-1394 adapter, also known as FireWire adapter, for controlling FireWire devices.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques shown in the figures can be implemented using code and data stored and executed on one or more electronic devices. Such electronic devices store and communicate (internally and/or with other electronic devices over a network) code and data using computer-readable media, such as non-transitory computer-readable storage media (e.g., magnetic disks; optical disks; random access memory; read only memory; flash memory devices; phase-change memory) and transitory computer-readable transmission media (e.g., electrical, optical, acoustical or other form of propagated signals—such as carrier waves, infrared signals, digital signals).

The processes or methods depicted in the preceding figures may be performed by processing logic that comprises hardware (e.g. circuitry, dedicated logic, etc.), firmware, software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

In the foregoing specification, embodiments of the invention have been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A computer-implemented method for processing medical images, the method comprising:

presenting a medical image processing interface that processes the medical images based on a plurality of image processing parameters, wherein the medical image processing interface provides an option to select either an advanced image processing system or an automatic image processing system;

in response to receiving a selection of the advanced image processing system, providing, by the advanced image processing system, an advanced medical image processing interface, the advanced medical image processing interface including a plurality of input fields that require a user to manually specify the plurality of image processing parameters; and in response to receiving a selection of the automatic image processing system, providing, by the automatic image processing system, an automatic medical image processing interface having a series of operation stages automating a plurality of user interactions to obtain the plurality of image processing parameters, wherein providing the automatic medical image processing interface comprises in response to an image processing indicator received from a client device, automatically identifying a first medical image based on the image processing indicator and determining, without user intervention, image operations including one or more image processing parameters associated with the operation stages, performing the image operations on the first medical image based on the obtained image processing parameters, generating a second medical image, transmitting the second medical image to the client device to be presented on a display of the client device, causing the client device to display a message prompting the user whether the user is satisfied with the second medical image, in response to receiving an indication that the user is unsatisfied with the second medical image, presenting one or more remedial options to reprocess the first medical image, in response to receiving a selection of a first remedial option, determining an operation stage associated with the first remedial option, and invoking the advanced image processing system to allow the user, via the advanced medical image processing interface, to manually modify one or more image processing parameters of the operation stage associated with the first remedial option, in response to receiving a selection of one of the remedial options indicating that the user wishes to examine specific steps concerning how the first medical image was processed, invoking the advanced image processing system to cause the client device to display detailed image processing parameters associated with one or more of the steps involved in processing the first medical image, and to allow the user, via the advanced medical image processing interface, to step through the steps to confirm accuracy in processing the first medical image at each of the one or more of the steps, to specify at least some of the image processing parameters and change results of at least one of the steps for reprocessing the first medical image, wherein changed data associated with the chanced results is propagated through following steps when the first medical image is reprocessed, and reprocessing the first medical image based on the modified image processing parameters obtained by the advanced image processing system.

2. The method of claim 1, wherein presenting one or more remedial options to the first medical image comprises:
in response to receiving a selection of a second remedial option, automatically modifying at least one of the image processing parameters based on the selected remedial option; and
reprocessing the first medical image based on the modified image processing parameters.

3. The method of claim 1, wherein providing an automatic medical image processing interface further comprises:
causing the client device to display a processing timeline having a plurality of processing stages, each being represented by one of a plurality of graphical representations on the processing timeline; and
visually indicating via one of the graphical representations on the processing timeline which of the processing stages is a current processing stage.

4. The method of claim 3, further comprising:
indicating via a first of the graphical representations that the current processing stage is a first processing stage, in response to a request received from a user for processing a first medical image associated with a first patient;
indicating via a second of the graphical representations that the current processing stage is a second processing stage, in response to presenting the second medical image at the client device; and
indicating via a third of the graphical representations that the current processing stage is a third processing stage, when the user is prompted to confirm whether the user is satisfied with the second medical image.

5. The method of claim 1, wherein providing an automatic medical image processing interface further comprises:
transmitting to the client device a graphical representation representing a human body of a patient having a plurality of selectable tags to be displayed therein, each selectable tag corresponding to one of a plurality of medical procedures performed on one or more body areas of the human body; and
in response to a first selection of a first of the tags corresponding to a first medical procedure, presenting a list of one or more medical images associated with the first medical procedure, including the act medical image.

6. The method of claim 5, further comprising:
automatically determining a body area identifier (ID) identifying a body area corresponding to the first tag;
determining a list of one or more medical images based on the body area ID and a patient ID identifying the patient; and
transmitting the list of medical images to the client device to be displayed therein.

7. The method of claim 6, further comprising determining a procedure ID identifying the first medical procedure, wherein the medical images are associated with the first medical procedure performed on a body area identified by the body area ID.

8. The method of claim 1, wherein providing an automatic medical image processing interface further comprises:
transmitting to the client device a list of one or more medical appointments of a patient that have been previously scheduled with one or more medical physicians;
for each of the appointments, indicating whether there is at least one medical image associated with the medical appointment; and
in response to a second selection selecting one of the medical appointments, transmitting to the client device a list of one or more medical images associated with the selected medical appointment, including the first medical image.

9. The method of claim 8, further comprising automatically determining an appointment ID identifying the selected appointment, wherein the medical images are identified further based on the appointment ID and the patient ID.

10. The method of claim 1, wherein providing an automatic medical image processing interface further comprises:
transmitting to the client device a List of medical procedures that have been performed on a patient;
for each of the medical procedures, indicating whether there is at least one medical image associated with the medical procedure; and
in response to a third selection selecting one of the medical procedures, presenting a list of one or more medical images associated with the selected medical procedure, including the first medical image.

11. The method of claim 10, further comprising automatically determining a procedure ID identifying the selected medical procedure, wherein the medical images are identified based on the procedure ID and the patient ID.

12. The method of claim 1, wherein providing an automatic medical image processing interface further comprises:
transmitting to the client device a list of one or more medical conditions of a patient;
for each of the medical conditions, indicating whether there is at least one medical image associated with the medical condition; and
in response to a fourth selection selecting one of the medical conditions, presenting a list of one or more medical images associated with the selected medical condition, including the first medical image.

13. The method of claim 12, further comprising automatically determining a medical condition ID identifying the selected medical condition, wherein the medical images are identified based on the medical condition ID and the patient ID.

14. A non-transitory machine-readable medium having instructions stored therein, which when executed by a processor, cause the processor to perform operations for processing medical images, the operations comprising:
presenting a medical image processing interface that processes the medical images based on a plurality of image processing parameters, wherein the medical image processing interface provides an option to select either an advanced image processing system or an automatic image processing system;
in response to receiving a selection of the advanced image processing system, providing, by the advanced image processing system, an advanced medical image processing interface, the advanced medical image processing interface including a plurality of input fields that require a user to manually specify the plurality of image processing parameters; and
in response to receiving a selection of the automatic image processing system, providing, by the automatic image processing system, an automatic medical image processing interface having a series of operation stages automating a plurality of user interactions to obtain the plurality of image processing parameters, wherein providing the automatic medical image processing interface comprises
in response to an image processing indicator received from a client device, automatically identifying a first medical image based on the image processing indicator and determining, without user intervention, image operations including one or more image processing parameters associated with the operation stages, performing the image operations on the first medical image based on the obtained image processing parameters, generating a second medical image, transmitting the second medical image to the client device to be presented on a display of the client device, causing the client device to display a message prompting the user whether the user is satisfied with the second medical image, in response to receiving an indication that the user is unsatisfied with the second medical image, presenting one or more remedial options to reprocess the first medical image, in response to receiving a selection of a first remedial option, determining an operation stage associated with the first remedial option, and invoking the advanced image processing system to allow the user, via the advanced medical image processing interface, to manually modify one or more image processing parameters of the operation stage associated with the first remedial option, in response to receiving a selection of one of the remedial options indicating that the user wishes to examine specific steps concerning how the first medical image was processed, invoking the advanced image processing system to cause the client device to display detailed image processing parameters associated with one or more of the steps involved in processing the first medical image, and to allow the user, via the advanced medical image processing interface, to step through the steps to confirm accuracy in processing the first medical image at each of the one or more of the steps, to specify at least some of the image processing parameters and change results of at least one of the steps for reprocessing the first medical image, wherein changed data associated with the changed results is propagated through following steps when the first medical image is reprocessed, and reprocessing the first medical image based on the modified image processing parameters obtained by the advanced image processing system.

15. The non-transitory machine-readable medium of claim 14, wherein presenting one or more remedial options to reprocess the first medical image comprises:

in response to receiving a selection of a second remedial option, automatically modifying at least one of the image processing parameters based on the selected remedial option; and reprocessing the first medical image based on the modified image processing parameters.

16. The non-transitory machine-readable medium of claim 14, wherein providing an automatic medical image processing interface further comprises:

causing the client device to display a processing timeline having a plurality of processing stages, each being represented by one of a plurality of graphical representations on the processing timeline; and visually indicating via one of the graphical representations on the processing timeline which of the processing stages is a current processing stage.

17. The non-transitory machine-readable medium of claim 16, wherein the operations further comprise:

indicating via a first of the graphical representations that the current processing stage is a first processing stage, in response to a request received from a user for processing a first medical image associated with a first patient;

indicating via a second of the graphical representations that the current processing stage is a second processing stage, in response to presenting the second medical image at the client device; and indicating via a third of the graphical representations that the current processing stage is a third processing stage, when the user is prompted to confirm whether the user is satisfied with the second medical image.

18. A system for processing medical images, comprising:

a processor;

an interface system executed by the processor to process the medical images based on a plurality of image processing parameters, wherein the medical image processing interface provides an option to select either an advanced medical image processing interface or an automatic medical image processing interface;

an advanced image processing system executed by the processor to provide the advanced medical image processing interface, the advanced medical image processing interface including a plurality of input fields that require a user to manually specify the plurality of image processing parameters; and an automatic image processing system executed by the processor to provide the automatic medical image processing interface having a series of operation stages automating a plurality of user interactions to obtain the plurality of image processing parameters, wherein providing the automatic medical image processing interface comprises in response to an image processing indicator received from a client device, automatically identifying a first medical image based on the image processing indicator and determining, without user intervention, image operations including one or more image processing parameters associated with the operation stages, performing the image operations on the first medical image based on the obtained image processing parameters, generating a second medical image, transmitting the second medical image to the client device to be presented on a display of the client device, causing the client device to display a message prompting the user whether the user is satisfied with the second medical image, in response to receiving an indication that the user is unsatisfied with the second medical image, presenting one or more remedial options to reprocess the first medical image, in response to receiving a selection of a first remedial option, determining an operation stage associated with the first remedial option, and invoking the advanced image processing system to allow the user, via the advanced medical image processing interface, to manually modify one or more image processing parameters of the operation stage associated with the first remedial option, in response to receiving a selection of one of the remedial options indicating that the user wishes to examine specific steps concerning how the first medical image was processed, invoking the advanced image processing system to cause the client device to display detailed image processing parameters associated with one or more of the steps involved in processing the first medical image, and to allow the user, via the advanced medical image processing interface, to step through the steps to confirm accuracy in processing the first medical image at each of the one or more of the steps, to specify at least some of the image processing parameters and change results of at least one of the steps for reprocessing the first medical image, wherein changed data associated with the changed results is propagated through following steps when the first medical image is reprocessed, and reprocessing the first medical image based on the modified image processing parameters obtained by the advanced image processing system.

19. The system of claim 18, wherein presenting one or more remedial options to reprocess the first medical image comprises:

in response to receiving a selection of a second remedial option, automatically modifying at least one of the image processing parameters based on the selected remedial option; and reprocessing the first medical image based on the modified image processing parameters.

20. The system of claim 18, wherein providing an automatic medical image processing interface further comprises:

causing the client device to display a processing timeline having a plurality of processing stages, each being represented by one of a plurality of graphical representations on the processing timeline; and visually indicating via one of the graphical representations on the processing timeline which of the processing stages is a current processing stage.

21. The system of claim 20, wherein the automatic image processing system is to:

indicate via a first of the graphical representations that the current processing stage is a first processing stage, in response to a request received from a user for processing a first medical image associated with a first patient;

indicate via a second of the graphical representations that the current processing stage is a second processing stage, in response to presenting the second medical image at the client device; and indicate via a third of the graphical representations that the current processing stage is a third processing stage, when the user is prompted to confirm whether the user is satisfied with the second medical image.

* * * * *